US012599608B2

(12) United States Patent
Theodoris et al.

(10) Patent No.: US 12,599,608 B2
(45) Date of Patent: Apr. 14, 2026

(54) METHODS FOR TREATING CARDIAC VALVE DISEASE

(71) Applicants: The Regents of the University of California, Oakland, CA (US); The J. David Giadstone institutes, a testamentary trust estabiished under the Will of J. David, San Francisco, CA (US)

(72) Inventors: Christina Theodoris, San Francisco, CA (US); Deepak Srivastava, San Francisco, CA (US)

(73) Assignees: The Regents of the University of California, Oakland, CA (US); The J. David Gladstone Institutes, a testamentary trust established under the Will of J. David Gladstone, San Francisco, CA (US)

(*) Notice: Subject to any disclaimer, the term of this patent is extended or adjusted under 35 U.S.C. 154(b) by 0 days.

(21) Appl. No.: 17/269,623

(22) PCT Filed: Aug. 20, 2019

(86) PCT No.: PCT/US2019/047295
§ 371 (c)(1),
(2) Date: Feb. 19, 2021

(87) PCT Pub. No.: WO2020/041333
PCT Pub. Date: Feb. 27, 2020

(65) Prior Publication Data

US 2021/0228594 A1 Jul. 29, 2021

Related U.S. Application Data

(60) Provisional application No. 62/721,389, filed on Aug. 22, 2018.

(51) Int. Cl.
*A61K 31/55* (2006.01)
*A61K 31/132* (2006.01)
(Continued)

(52) U.S. Cl.
CPC ............ *A61K 31/55* (2013.01); *A61K 31/132* (2013.01); *A61K 31/198* (2013.01);
(Continued)

(58) Field of Classification Search
CPC .... A61K 31/55; A61K 31/132; A61K 31/198; A61K 31/396; A61K 31/426;
(Continued)

(56) References Cited

U.S. PATENT DOCUMENTS

2017/0058349 A1 3/2017 Levy et al.
2017/0332686 A1 11/2017 Li et al.

FOREIGN PATENT DOCUMENTS

JP 2010520307 A 6/2010
JP 2011528322 A 11/2011
(Continued)

OTHER PUBLICATIONS

O'Brien, Kevin. Pathogenesis of Calcific Aortic Valve Disease, Arteriosclerosis, Thrombosis and Valscular Biology, vol. 26, Issue 8, Aug. 1, 2006, pp. 1721-1728. (Year: 2006).*
(Continued)

*Primary Examiner* — James H Alstrum-Acevedo
*Assistant Examiner* — Lauren Wells
(74) *Attorney, Agent, or Firm* — Schwegman Lundberg & Woessner, P.A.

(57) ABSTRACT

The present disclosure provides methods of treating cardiac valve disease, e.g., calcific aortic valve disease (CAVD), by administering to a subject in need thereof a therapeutically effective amount of a compound of any one of Formulae I-X or a pharmaceutically acceptable salt, solvate or prodrug
(Continued)

thereof. Also provided are methods of identifying a candidate compound for treatment of cardiac valve disease, e.g., CAVD.

4 Claims, 45 Drawing Sheets

(51) Int. Cl.

| | |
|---|---|
| ***A61K 31/198*** | (2006.01) |
| ***A61K 31/396*** | (2006.01) |
| ***A61K 31/426*** | (2006.01) |
| ***A61K 31/433*** | (2006.01) |
| ***A61K 31/44*** | (2006.01) |
| ***A61K 31/485*** | (2006.01) |
| ***A61K 31/506*** | (2006.01) |
| ***A61K 45/06*** | (2006.01) |

(52) U.S. Cl.
CPC .......... *A61K 31/396* (2013.01); *A61K 31/426* (2013.01); *A61K 31/433* (2013.01); *A61K 31/44* (2013.01); *A61K 31/485* (2013.01); *A61K 31/506* (2013.01); *A61K 45/06* (2013.01)

(58) Field of Classification Search
CPC .... A61K 31/433; A61K 31/44; A61K 31/485; A61K 31/506; A61K 45/06; A61K 31/4035; A61K 31/4245; A61K 31/428; A61K 31/4453; A61K 31/635; A61P 9/10
See application file for complete search history.

(56) References Cited

FOREIGN PATENT DOCUMENTS

| | | | | |
|---|---|---|---|---|
| JP | 2021534254 A | 12/2021 | | |
| JP | 7476198 | 4/2024 | | |
| WO | WO-2005072731 A1 * | 8/2005 | .......... | C07C 205/44 |
| WO | 2020041333 | 2/2020 | | |

OTHER PUBLICATIONS

Agmon et al. Aortic valve sclerosis and aortic atherosclerosis:different manifestations of the same disease?: Insights from a population-based study, Jn. Am. College of Cardio, vol. 38, Issue 3, Sep. 2001, pp. 827-834. (Year: 2001).*
Sathamurthy et al. Calcific aortic valve disease: Is it another face of atherosclerosis? Indian Heart Journal. vol. 67, Issue 5. Published Sep.-Oct. 2015. (Year: 2015).*
Teng et al. Development of Novel Cell Lines for High-Throughput Screening to Detect Estrogen-Related Receptor Alpha Modulators. SLAS Discovery. vol. 22, Issue 6. Published Jul. 1017. (Year: 2017).*
Collett et al. Dosage Regimens. Basicmedical Key. Retrieved from the internet on Nov. 27, 2023, https://basicmedicalkey.com/dosage-regimens/. Published Jun. 2, 2016. (Year: 2016).*
"International Application Serial No. PCT US2019 047295, International Search Report mailed Dec. 23, 2019", 4 pgs.
"International Application Serial No. PCT US2019 047295, Written Opinion mailed Dec. 23, 2019", 6 pgs.
"International Application Serial No. PCT US2019 047295, Invitation to Pay Additional Fees and Partial Search Report mailed Oct. 22, 2019", 3 pgs.
"International Application Serial No. PCT US2019 047295, International Preliminary Report on Patentability mailed Mar. 4, 2021", 8 pgs.
Du, "The discovery of novel, potent ERR-alpha inverse agonists for the treatment of triple negative breast cancer", European Journal of Medicinal Chemistry vol. 136, (Apr. 22, 2017), 457-467.
Himura, "Short-term effects of naloxone hemodynamics and baroreflex function in conscious dogs with pacing-induced congestive heart failure", Journal of the American College of Cardiology vol. 23, (Jan. 1994), 194-200.
Sun, "Novel endocrine therapeutic strategy in endometrial carcinoma targeting estrogen-related receptor a by XCT790 and siRNA1", Cancer Management and Research, (Aug. 10, 2018), 2521-2535.
"European Application Serial No. 19853073.5, Response to Communication pursuant to Rules 161(2) and 162 EPC filed Sep. 30, 2021", 13 pgs.
"Novel missense mutations (p. T596M and p. P1797H) in NOTCH1 in patients with bicuspid aortic valve", Biochemical and Biophysical Research Communications 345, (2006), 1460-1465.
Clark, Cynthia R, "Targeting Cadherin-11 Prevents Notch1-Mediated Calcific Aortic Valve Disease", Circulation. 135(24), (6 12017), 2448-2450.
Foffa, I, "Sequencing of NOTCH1, GATA5, TGFBR1 and TGFBR2 genes in familial cases of bicuspid aortic valve", BMC Med Genet 14:44, (2013), 8 pgs.
Garg, V, "Mutations in NOTCH1 cause aortic valve disease", Nature vol. 437 8, (2005), 6 pgs.
Hadji, F, "Altered DNA Methylation of Long Noncoding Rna H19 in Calcific Aortic Valve Disease Promotes Mineralization by Silencing NOTCH1", Circulation vol. 134 Issue 23, (2016), 1848-1862.
Theodoris, C V, "Human Disease Modeling Reveals Integrated Transcriptional and Epigenetic Mechanisms of NOTCH1 Haploinsufficiency", Cell 160(6), (2015), 1072-1086.
"European Application Serial No. 19853073.5, Extended European Search Report mailed Apr. 25, 2022", 8 pgs.
Maria, Jusus Vazquez, et al., "Discovery of GSK837149A, an inhibitor of human fatty acid synthase targeting the &bgr;-ketoacyl reductase reaction", FEBS Journal, vol. 275, No. 7, (Apr. 25, 2008), 1556-1567.
Rodgers, Joseph T, et al., "Cdc2-like Kinase 2 Is an Insulin-Regulated Suppressor of Hepatic Gluconeogenesis", Cell Metabolism, vol. 11, No. 1, (Jan. 1, 2010), 23-34.
"European Application Serial No. 19853073.5, Response filed Nov. 21, 2022 to Extended European Search Report mailed Apr. 25, 2022", 197 pgs.
"Japanese Application Serial No. 2021-533376, Notification of Reasons for Rejection mailed Jul. 18, 23", W/English Translation, 8 pgs.
"European Application Serial No. 23182183.6, Extended European Search Report mailed Jan. 9, 2024", 15 pgs.
"European Application Serial No. 23182183.6, Partial European Search Report mailed Sep. 29, 2023", 17 pgs.
Himura, Y., et al., "Short-Term Effects of Naloxone on Hemodynamics and Baroreflex Function in Conscious Dogs with Pacing-Induced Congestive Heart Failure", Journal of the American College of Cardiology, Elsevier, Amsterdam, NL, vol. 23, No. 1, (Jan. 1, 1994), 194-200.
Jeffrey, Borer S., et al., "Drug Therapy for Heart Valve Diseases", Circulation, vol. 132, No. 11, (Sep. 15, 2015), 1038-1045.
Olsen, Patrick L, et al., "Naloxone Infusion During Thoracic Endovascular Aortic Aneurysm Repair to Prevent Spinal Cord Injury", Department of Anesthesiology and Perioperative Medicine, Drexel university College of Medicine, vol. 32, No. 2, (Apr. 1, 2018).
Tomai, Fabrizio, et al., "Effects of naloxone on myocardial ischemic preconditioning in human", Journal of the American College of Cardiology, vol. 33, No. 7, (Jun. 1, 1999), 1863-1869.

* cited by examiner

FIG. 10A

| Name | Library | Candidate Selection Strategy | Validation |
|---|---|---|---|
| cytochalasin | Ding | KNN | yes |
| Fmoc-leu | Ding | KNN | yes |
| GSK837149A | Ding | KNN | yes |
| RO-4929097 | Ding | KNN | yes |
| Alprostadil | Ding | KNN | |
| Norfloxacin | Ding | KNN | |
| YC-1 | Ding | KNN | |
| CB_1954 | LOPAC | KNN | yes |
| L-741,626 | LOPAC | KNN | |
| Naloxone_benzoylhydrazone | LOPAC | KNN | |
| Tulobuterol_hydrochloride | LOPAC | KNN | |
| Biperiden_hydrochloride | LOPAC | Hierarchical_clustering | yes |
| Putrescine_dihydrochloride | LOPAC | Hierarchical_clustering | yes |
| TG003 | LOPAC | Hierarchical_clustering | yes |
| XCT790 | LOPAC | Hierarchical_clustering | yes |
| (-)-trans-(1S,2S)-U-50488_hydrochloride | LOPAC | Hierarchical_clustering | |
| (+)-Brompheniramine_maleate | LOPAC | Hierarchical_clustering | |
| (+)-Nicotine_(+)-di-p-toluoyl_tartrate | LOPAC | Hierarchical_clustering | |
| 8-Bromo-cGMP_sodium | LOPAC | Hierarchical_clustering | |
| Alprenolol_hydrochloride | LOPAC | Hierarchical_clustering | |
| Amiodarone_hydrochloride | LOPAC | Hierarchical_clustering | |
| Ancitabine_hydrochloride | LOPAC | Hierarchical_clustering | |
| BWB70C | LOPAC | Hierarchical_clustering | |
| Carbachol | LOPAC | Hierarchical_clustering | |
| Chlormethiazole_hydrochloride | LOPAC | Hierarchical_clustering | |
| DL-erythro-Dihydrosphingosine | LOPAC | Hierarchical_clustering | |
| Flumazenil | LOPAC | Hierarchical_clustering | |
| L-Aspartic_acid | LOPAC | Hierarchical_clustering | |
| Phentolamine_mesylate | LOPAC | Hierarchical_clustering | |
| Phosphonoacetic_acid | LOPAC | Hierarchical_clustering | |
| Piroxicam | LOPAC | Hierarchical_clustering | |
| Pyridostigmine_bromide | LOPAC | Hierarchical_clustering | |
| R-(-)-Desmethyldeprenyl_hydrochloride | LOPAC | Hierarchical_clustering | |
| S(-)-Willardiine | LOPAC | Hierarchical_clustering | |
| Thio-L-citrulline | LOPAC | Hierarchical_clustering | |
| TPMPA | LOPAC | Hierarchical_clustering | |
| U-101958_maleate | LOPAC | Hierarchical_clustering | |

FIG. 10B

| Name | Activity |
| --- | --- |
| cytochalasin | bind_to_actin_filaments_and_block_polymerization;_blocks_migration_and_cell_division |
| Fmoc-leu | PPARgamma_activator |
| GSK837149A | selective_inhibitor_of_human_fatty_acid_synthase |
| R04929097 | oral_γ-secretase_inhibitor |
| Alprostadil | prostaglandin_(PGE-1),_vasodilator |
| Norfloxacin | quinolone_antibiotic |
| YC-1 | MeSH_Pharm_Class:_Platelet_Aggregation_Inhibitors |
| CB_1954 | Anti-neoplastic_prodrug_activated_by_NAD(P)H_quinone_oxidoreductase-2 |
| L-741,626 | Selective_D2_dopamine_receptor_antagonist |
| Naloxone_benzoylhydrazone | kappa3_Opioid_receptor_agonist;_mixed_mu_opioid_receptor_agonist-antagonist;_inhibits_atherosclerosis_in_mice |
| Tulobuterol_hydrochloride | beta-Adrenoceptor_agonist_related_to_structurally_to_terbutaline;_bronchodilator |
| Biperiden_hydrochloride | Non-selective_muscarinic_acetylcholine_receptor_antagonist;_antiparkinsonian |
| Putrescine_dihydrochloride | Binds_to_the_polyamine_modulatory_site_of_the_NMDA_glutamate_receptor_and_potentiates_NMDA-induced_currents;_precursor_of_spermidine |
| TG003 | Potent,_specific,_and_reversible_Cdc2-like_kinase_(Clk)_inhibitor._Competes_with_ATP._Inhibits_expression_of_platelet_tissue_factor_that_initiates_thrombin_formation |
| XCT790 | Potent_and_selective_estrogen-related_receptor_alpha_(ERRalpha)_inverse_agonist. |

FIG. 10C

| Name | Activity |
| --- | --- |
| (-)-trans-(1S,2S)-U-50488_hydrochloride | Potent_kappa_opioid_receptor_agonist;_more_potent_enantiomer_of_(±)-trans-U-50488 |
| (+)-Brompheniramine_maleate | H1_Histamine_receptor_antagonist |
| (+)-Nicotine_(+)-di-p-toluoyl_tartrate | Less_active_enantiomer_of_naturally-occurring_(-)-nicotine |
| 8-Bromo-cGMP_sodium | Membrane-permeable_analog_of_cGMP |
| Alprenolol_hydrochloride | beta_Adrenoceptor_antagonist |
| Amiodarone_hydrochloride | alpha_and_beta_adrenoceptor_agonist;_inhibits_binding_of_1,4-dihydropyridine_to_L-type_Ca2+_channels;_coronary_vasodilator |
| Ancitabine_hydrochloride | Antineoplastic |
| BWB70C | Selective_inhibitor_of_5-lipoxygenase |
| Carbachol | Acetylcholine_receptor_agonist |
| Chlormethiazole_hydrochloride | GABA(A)_agonist;_glycine_receptor_modulator |
| DL-erythro-Dihydrosphingosine | Protein_kinase_C,_phospholipase_A2,_and_phospholipase_D_inhibitor |
| Flumazenil | Benzodiazepine_receptor_antagonist |
| L-Aspartic_acid | Endogenous_excitatory_amino_acid_neurotransmitter |
| Phentolamine_mesylate | ATP-sensitive_K+_channel_blocker;_alpha_adrenoceptor_antagonist |
| Phosphonoacetic_acid | DNA_Polymerase_inhibitor |
| Piroxicam | Cyclooxygenase_(COX)_inhibitor |
| Pyridostigmine_bromide | Cholinesterase_inhibitor |
| R-(-)-Desmethyldeprenyl_hydrochloride | MAO-B_inhibitor;_metabolite_of_L-deprenyl |
| S(-)-Willardiine | AMPA-kainate_glutamate_receptor_agonist |
| Thio-L-citrulline | Potent_and_selective_inhibitor_of_neuronal_and_endothelial_isoforms_of_nitric_oxide_synthase |
| TPMPA | Selective_GABA-C_receptor_antagonist |
| U-101958_maleate | Selective_D4_dopamine_receptor_antagonist |

(#Calcified: 5/15 Saline vs 2/19 Naloxone)

Putrescine + CB1954 Combination

GSK837149A (excluding echos delayed >10 days)

METHODS FOR TREATING CARDIAC VALVE DISEASE

CROSS-REFERENCE TO RELATED APPLICATION

This application claims benefit under 35 U.S.C. § 119(e) of provisional application 62/721,389, filed Aug. 22, 2018, which application is hereby incorporated by reference in its entirety.

INTRODUCTION

Determining the gene regulatory networks driving human disease allows the design of therapies targeting the underlying disease mechanism rather than mere symptomatic management. Mapping the architecture of the dysregulated network enables screening for molecules that correct the network's core regulatory elements as opposed to peripheral downstream effectors that will likely have only limited influence on the disease process. Identifying molecules that target key regulatory nodes focuses efforts on molecules that will ultimately have the broadest corrective effects on the entire network and therefore the largest impact on the disease as a whole.

Small molecules are traditionally screened for their effects on one to several outputs at most, from which their predicted efficacy on the disease as a whole is extrapolated. Whole transcriptome RNA sequencing (RNA-seq) would provide the most complete information about the effect of each small molecule on the transcriptome of the cells of interest, but its costliness prohibits its use for high-throughput drug screening. By contrast, the advent of targeted RNA-seq methods, which are significantly less costly as they focus sequencing on select transcripts of interest, permits high-throughput screening for network-correcting molecules by determining their effect on 100-200 transcripts within the disease network.

Calcific aortic valve disease (CAVD), the third leading cause of adult heart disease, is a progressive disorder that ranges from mild valve thickening without obstruction of blood flow, termed aortic sclerosis, to severe calcification with impaired leaflet motion, termed aortic stenosis. Neurogenic locus notch homolog protein 1 (NOTCH1) (N1) is a human membrane-bound transcription factor, and N1 haploinsufficiency ($N1^{+/-}$), in which a single functional copy of the N1 gene is present, has been identified as a cause of CAVD. The only current treatment for CAVD is valve transplant, necessitating over 100,000 valve transplants annually in the United States alone. Given that valve calcification progresses over time, there is an opportunity to intervene with a preventative medical therapy if one were elucidated. The present disclosure addresses the above issues and provides related advantages.

SUMMARY OF THE INVENTION

The present disclosure provides methods of treating cardiac valve disease, e.g., calcific aortic valve disease (CAVD), by administering to a subject in need thereof a therapeutically effective amount of a compound of any one of Formulae I-X or a pharmaceutically acceptable salt, solvate or prodrug thereof. Also provided are methods of identifying a candidate compound for treatment of cardiac valve disease, e.g., CAVD.

BRIEF DESCRIPTION OF THE DRAWINGS

FIG. 10A depicts 37 network-correcting molecule candidates identified by KNN and hierarchical clustering algorithms.

FIG. 10B depicts the activity of 15 of 37 network-correcting molecule candidates identified by KNN and hierarchical clustering algorithms.

FIG. 10C depicts the activity of 22 of 37 network-correcting molecule candidates identified by KNN and hierarchical clustering algorithms.

FIG. 11C (right/bottom) depicts the percentage of the AV calcified by Alizarin red staining in $N1^{+/-}/mTR^{G2}$ mice treated with Fmoc-leu or DMSO for a small initial cohort.

DEFINITIONS

Figure 1A:
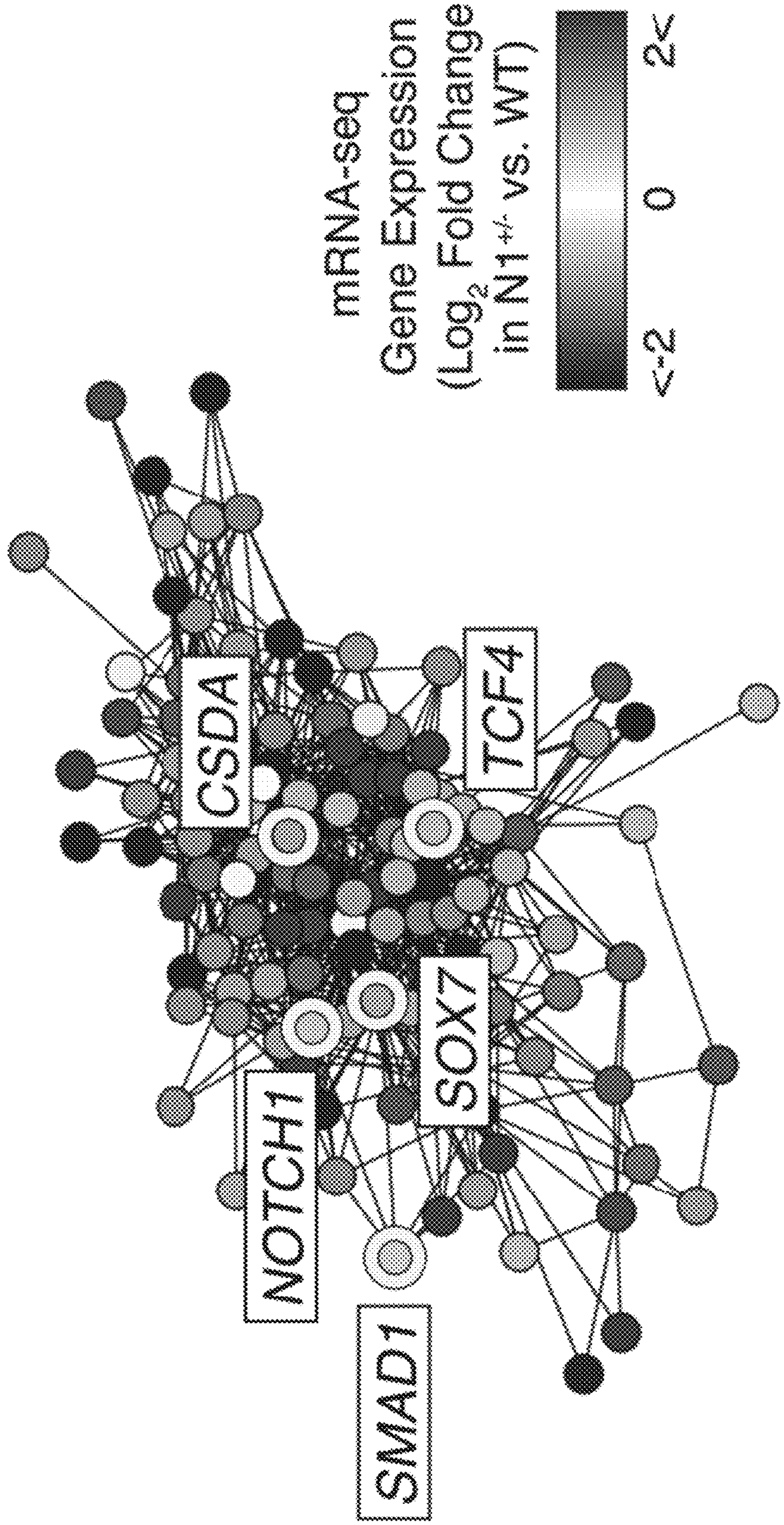
FIG. 1A depicts a map of gene network dysregulation by N1 haploinsufficiency (from targeted RNA-seq).
Figure 1B:
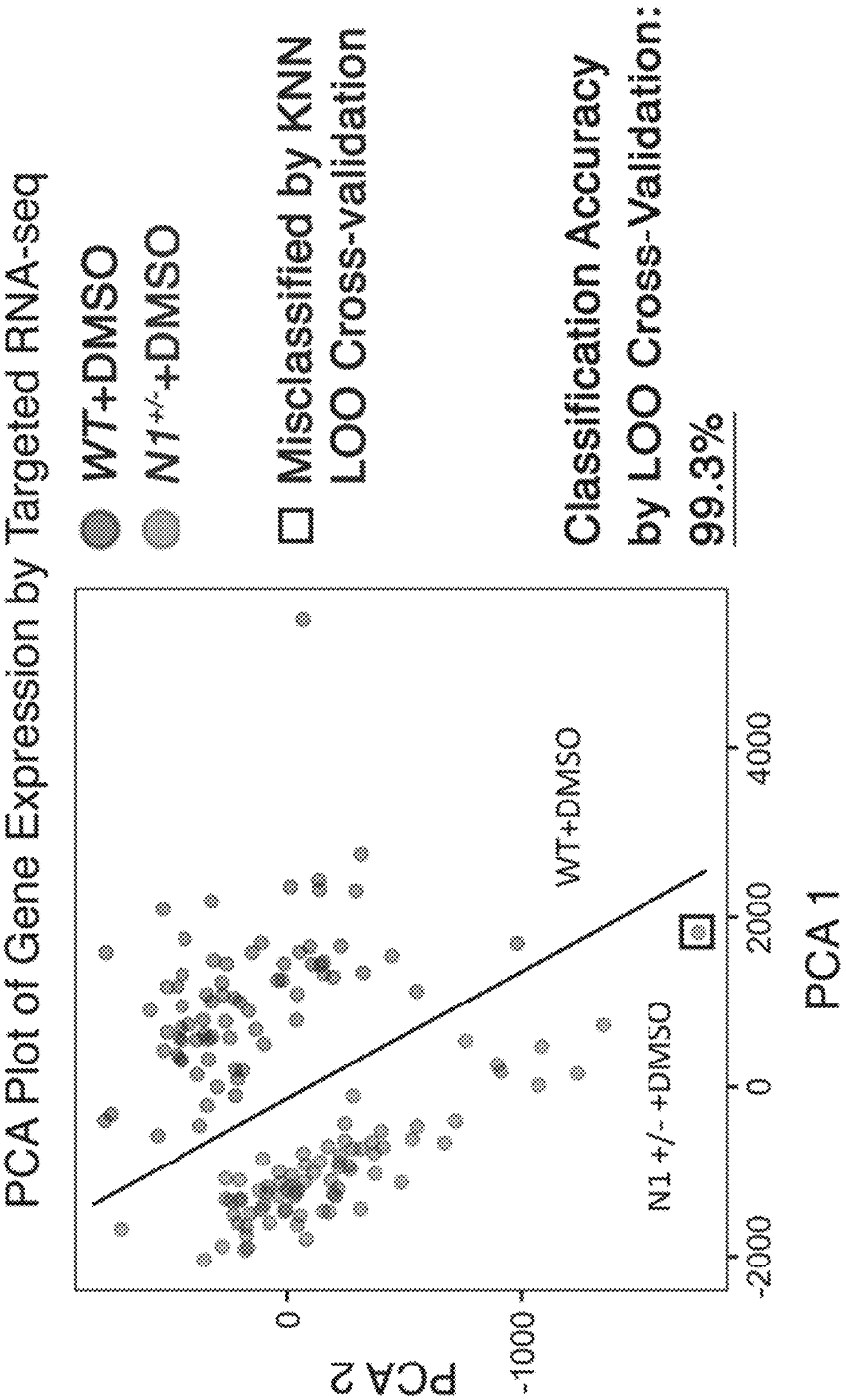
FIG. 1B depicts a principle components analysis (PCA) plot of gene expression in WT or $N1^{+/-}$ ECs (from targeted RNA-seq). The line through the graph divides WT+DMSO data points on the right and $N1^{+/-}$+DMSO data points on the left.
Figure 1C:
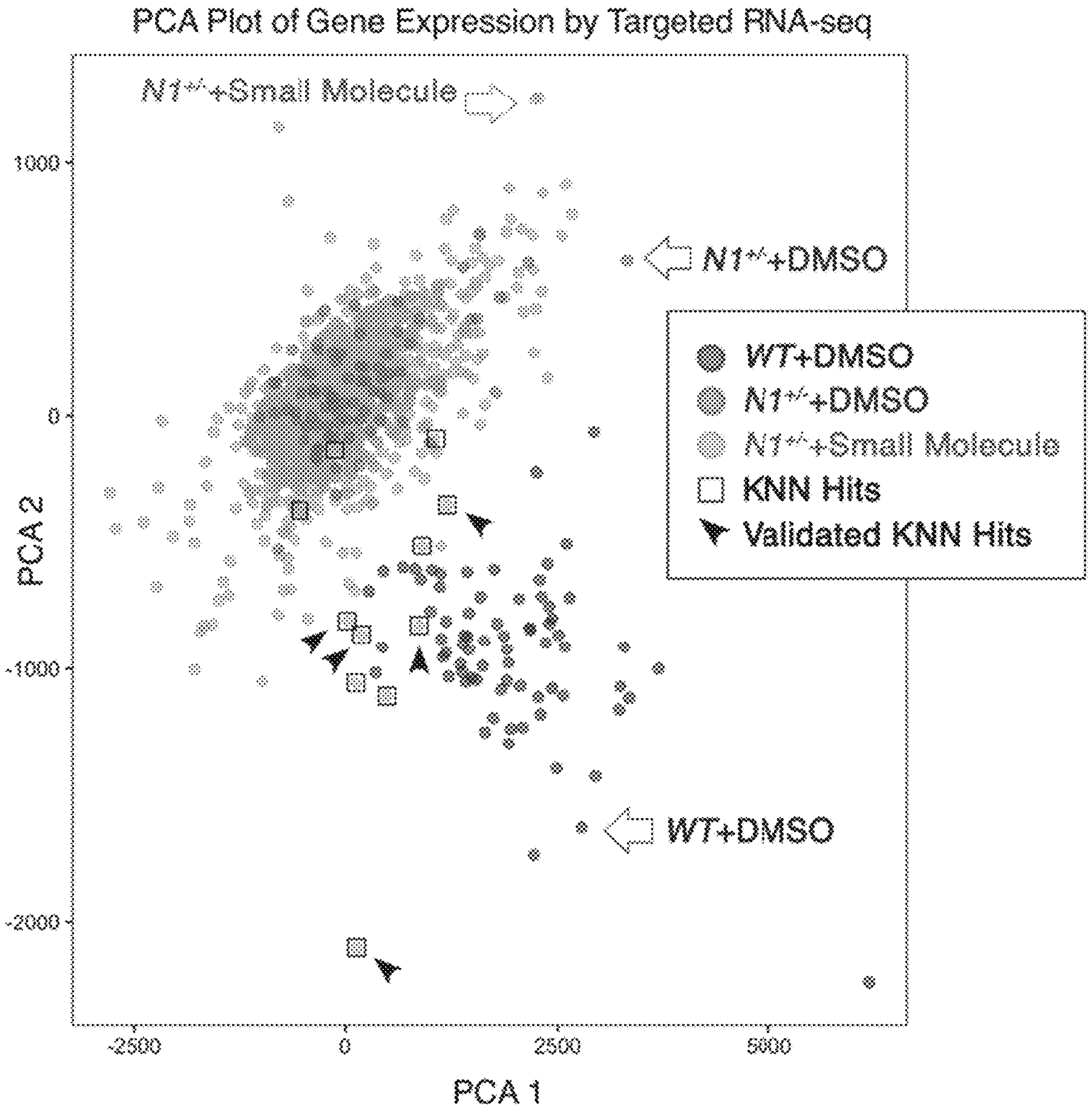
FIG. 1C depicts a PCA plot of gene expression in $N1^{+/-}$ ECs treated with one of 1595 small molecules compared to $N1^{+/-}$ or WT ECs exposed to DMSO (from targeted RNA-seq). Squares indicate molecule-treated $N1^{+/-}$ whose network transcription was corrected sufficiently to classify as WT by the KNN algorithm.
Figure 1D:
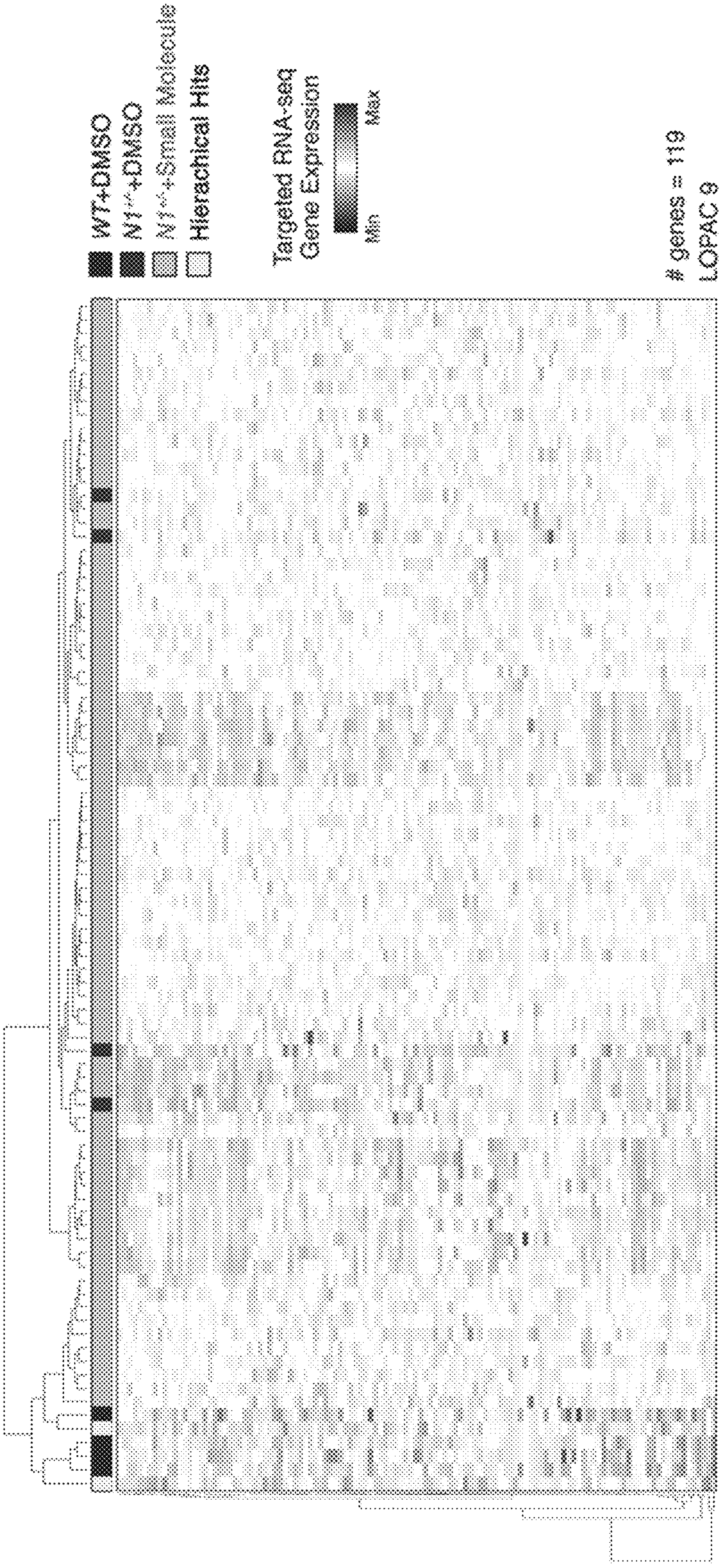
FIG. 1D depicts a hierarchical clustering of transcriptional profiles of $N1^{+/-}$ ECs treated with each of the small molecules (from LOPAC library plate 9 of 16) compared to $N1^{+/-}$ or WT ECs exposed to DMSO (from targeted RNA-seq).
Figure 1E:
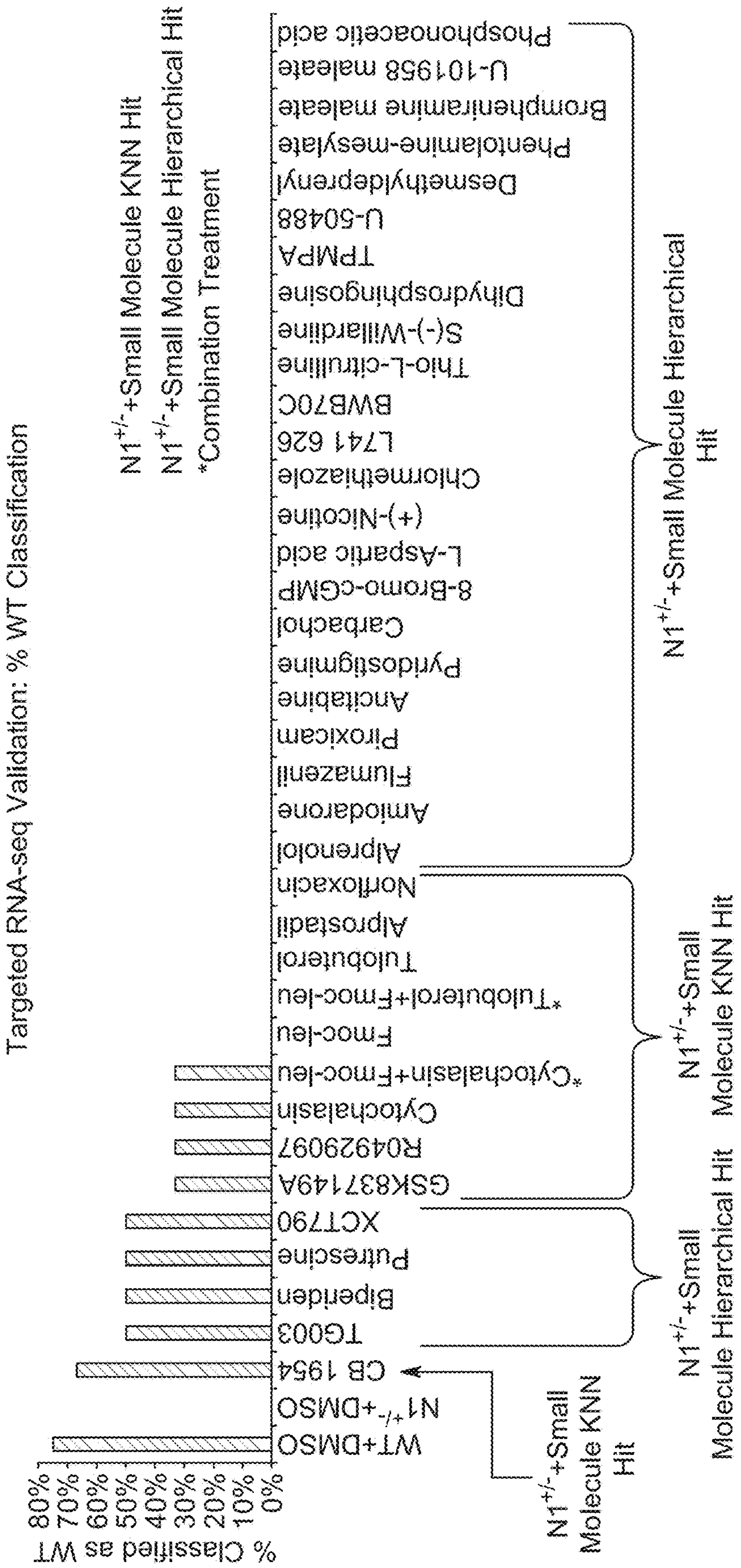
FIG. 1E depicts percent of targeted RNA-seq validation replicates that classified as WT with true identities of DMSO-exposed WT, DMSO-exposed $N1^{+/-}$, or small molecule-treated $N1^{+/-}$ (from targeted RNA-seq).

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc.

A "therapeutically effective amount" or "efficacious amount" means the amount of a compound that, when administered to a mammal or other subject for treating a disease, is sufficient to effect such treatment for the disease. The "therapeutically effective amount" may vary depending on the compound, the disease and its severity and the age, weight, etc., of the subject to be treated.

As used herein, the term "stem cell" refers to an undifferentiated cell that can be induced to proliferate. The stem cell is capable of self-maintenance, meaning that with each cell division, one daughter cell will also be a stem cell. Stem cells can be obtained from embryonic, post-natal, juvenile or adult tissue. The term "progenitor cell", as used herein, refers to an undifferentiated cell derived from a stem cell, and is not itself a stem cell. Some progenitor cells can produce progeny that are capable of differentiating into more than one cell type.

The term "induced pluripotent stem cell" (or "iPS cell"), as used herein, refers to a pluripotent stem cell induced from a somatic cell, e.g., a differentiated somatic cell. iPS cells are capable of self-renewal and differentiation into cell fate-committed stem cells, including neural stem cells, as well as various types of mature cells.

Definition of Select Chemical Terminology

The nomenclature of certain compounds or substituents are used in their conventional sense, such as described in chemistry literature including but not limited to Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

As used herein, the term "alkyl" by itself or as part of another substituent refers to a saturated branched or straight-chain monovalent hydrocarbon radical derived by the removal of one hydrogen atom from a single carbon atom of a parent alkane. Typical alkyl groups include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms, such as from 1 to 4 carbon atoms.

"Alkanyl" by itself or as part of another substituent refers to a saturated branched, straight-chain or cyclic alkyl radical derived by the removal of one hydrogen atom from a single carbon atom of an alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkylene" refers to a branched or unbranched saturated hydrocarbon chain, usually having from 1 to 40 carbon atoms, more usually 1 to 10 carbon atoms and even more usually 1 to 6 carbon atoms. This term is exemplified by groups such as methylene ($—CH_2—$), ethylene ($—CH_2CH_2—$), the propylene isomers (e.g., $—CH_2CH_2CH_2—$ and $—CH(CH_3)CH_2—$) and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of an alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of an alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical $—C(O)R^{30}$, where $R^{30}$ is hydrogen, alkyl, cycloalkyl, cycloheteroalkyl, aryl, arylalkyl, heteroalkyl, heteroaryl, heteroarylalkyl as defined herein and substituted versions thereof. Representative examples include, but are not limited to formyl, acetyl, cyclohexylcarbonyl, cyclohexylmethylcarbonyl, benzoyl, benzylcarbonyl, piperonyl, succinyl, and malonyl, and the like.

The term "aminoacyl" refers to the group $—C(O)NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Alkoxy" by itself or as part of another substituent refers to a radical $—OR^{31}$ where $R^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —C(O)OR$^{31}$ where R$^{31}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of an aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group comprises from 6 to 20 carbon atoms. In certain embodiments, an aryl group comprises from 6 to 12 carbon atoms. Examples of an aryl group are phenyl and naphthyl.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In certain embodiments, an arylalkyl group is ($C_7$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$). In certain embodiments, an arylalkyl group is ($C_7$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Arylaryl" by itself or as part of another substituent, refers to a monovalent hydrocarbon group derived by the removal of one hydrogen atom from a single carbon atom of a ring system in which two or more identical or non-identical aromatic ring systems are joined directly together by a single bond, where the number of such direct ring junctions is one less than the number of aromatic ring systems involved. Typical arylaryl groups include, but are not limited to, biphenyl, triphenyl, phenyl-napthyl, binaphthyl, biphenyl-napthyl, and the like. When the number of carbon atoms in an arylaryl group are specified, the numbers refer to the carbon atoms comprising each aromatic ring. For example, ($C_5$-$C_{14}$) arylaryl is an arylaryl group in which each aromatic ring comprises from 5 to 14 carbons, e.g., biphenyl, triphenyl, binaphthyl, phenylnapthyl, etc. In certain embodiments, each aromatic ring system of an arylaryl group is independently a ($C_5$-$C_{14}$) aromatic. In certain embodiments, each aromatic ring system of an arylaryl group is independently a ($C_5$-$C_{10}$) aromatic. In certain embodiments, each aromatic ring system is identical, e.g., biphenyl, triphenyl, binaphthyl, trinaphthyl, etc.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. In certain embodiments, the cycloalkyl group is ($C_3$-$C_{10}$) cycloalkyl. In certain embodiments, the cycloalkyl group is ($C_3$-$C_7$) cycloalkyl.

"Cycloheteroalkyl" or "heterocyclyl" by itself or as part of another substituent, refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —S—S—, —O—S—, —NR$^{37}$R$^{38}$—, =N—N=, —N=N—, —N=N—NR$^{39}$R$^{40}$, —PR$^{41}$—, —P(O)$_2$—, —POR$^{42}$—, —O—P(O)$_2$—, —S—O—, —S—(O)—, —SO$_2$—, —SnR$^{43}$R$^{44}$— and the like, where R$^{37}$, R$^{38}$, R$^{39}$, R$^{40}$, R$^{41}$, R$^{42}$, R$^{43}$ and R$^{44}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In certain embodiments, the heteroarylalkyl group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Aromatic Ring System" by itself or as part of another substituent, refers to an unsaturated cyclic or polycyclic ring system having a conjugated 71 electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent, refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, 3-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Substituted" refers to a group in which one or more hydrogen atoms are independently replaced with the same or different substituent(s). Typical substituents include, but are not limited to, alkylenedioxy (such as methylenedioxy), -M, $—R^{60}$, —O—, =O, $—OR^{60}$, $—SR^{60}$, $—S^-$, =S, $—NR^{60}R^{61}$, $=NR^{60}$, $—CF_3$, —CN, —OCN, —SCN, —NO, $—NO_2$, $=N_2$, $—N_3$, $—S(O)_2O^-$, $—S(O)_2OH$, $—S(O)_2R^{60}$, $—OS(O)_2O^-$, $—OS(O)_2R^{60}$, $—P(O)(O^-)_2$, $—P(O)(OR^{60})(O^-)$, $—OP(O)(OR^{60})(OR^{61})$, $—C(O)R^{60}$, $—C(S)R^{60}$, $—C(O)OR^{60}$, $—C(O)NR^{60}R^{61}$, $—C(O)O^-$, $—C(S)OR^{60}$, $—NR^{62}C(O)NR^{60}R^{61}$, $—NR^{62}C(S)NR^{60}R^{61}$, $—NR^{62}C(NR^{63})NR^{60}R^{61}$ and $—C(NR^{62})NR^{60}R^{61}$ where M is halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring.

In certain embodiments, substituents include -M, $—R^{60}$, =O, $—OR^{60}$, $—SR^{60}$, $—S^-$, =S, $—NR^{60}R^{61}$, $=NR^{6}$, $—CF_3$, —CN, —OCN, —SCN, —NO, $—NO_2$, $=N_2$, $—N_3$, $—S(O)_2R^{60}$, $—OS(O)_2O^-$, $—OS(O)_2R^{60}$, $—P(O)(O^-)_2$, $—P(O)(OR^{60})(O^-)$, $—OP(O)(OR^{60})(OR^{61})$, $—C(O)R^{60}$, $—C(S)R^{60}$, $—C(O)OR^{60}$, $—C(O)NR^{60}R^{61}$, $—C(O)O^-$, $—NR^{62}C(O)NR^{60}R^{61}$. In certain embodiments, substituents include -M, $—R^{60}$, =O, $—OR^{6}$, $—SR^{60}$, $—NR^{60}R^{61}$, $—CF_3$, —CN, $—NO_2$, $—S(O)_2R^{60}$, $—P(O)(OR^{60})(O^-)$, $—OP(O)(OR^{60})(OR^{61})$, $—C(O)R^{60}$, $—C(O)OR^{60}$, $—C(O)NR^{60}R^{61}$, $—C(O)O^-$. In certain embodiments, substituents include -M, $—R^{60}$, =O, $—OR^{60}$, $—SR^{60}$, $—NR^{60}R^{61}$, $—CF_3$, —CN, $—NO_2$, $—S(O)_2R^{60}$, $—OP(O)(OR^{60})(OR^{61})$, $—C(O)R^{60}$, $—C(O)OR^{60}$, $—C(O)O^-$, where $R^{60}$, $R^{61}$ and $R^{62}$ are as defined above. For example, a substituted group may bear a methylenedioxy substituent or one, two, or three substituents selected from a halogen atom, a (1-4C)alkyl group and a (1-4C)alkoxy group.

The compounds described herein can contain one or more chiral centers and/or double bonds and therefore, can exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein.

Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^{2}H$, $^{3}H$, $^{11}C$, $^{13}C$, $^{14}C$, $^{15}N$, $^{18}O$, $^{17}O$, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

Before aspects of the present disclosure are further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. It is further noted that the claims may be drafted to exclude any recited element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication. Further, the dates of publication provided may be different from the actual publication dates which may need to be independently confirmed.

DETAILED DESCRIPTION

Whereas molecules discovered in animal models do not always translate to humans, induced pluripotent stem cell (iPSC) technology allows drug discovery in human iPSC-derived cells generated directly from patients affected by the disease.

A network-based drug screen was performed to identify small molecules that corrected the gene network dysregulated by N1 haploinsufficiency in human iPSC-derived endothelial cells (ECs) from patients affected by CAVD. Molecules targeting atherosclerotic and osteogenic pathways had the largest corrective impact on the network. Their effects mimicked that of siRNA inhibition of SOX7 and TCF4, two key regulatory nodes upregulated in N1 haploinsufficient ECs. Select compounds reduced N1-dependent cardiac valve disease in vivo in mice. In sum, network-based screening distinguishes molecules with broadly restorative effects on gene networks dysregulated in human disease that may thus represent promising candidates for treating the disease as a whole.

The present disclosure provides methods of treating cardiac valve disease, e.g., CAVD, by administering to a subject in need thereof a therapeutically effective amount of a compound of any one of Formulae I-X or a pharmaceutically acceptable salt, solvate or prodrug thereof. Also provided are methods of identifying a candidate compound for treatment of cardiac valve disease, e.g., CAVD.

Methods of Treating Cardiac Valve Disease

The present disclosure provides methods for treating cardiac valve disease, e.g., CAVD, by administering to a subject in need thereof a therapeutically effective amount of a compound of any one of Formulas I-X or a pharmaceutically acceptable salt, solvate or prodrug thereof. Methods for treating cardiac valve disease, e.g., CAVD, by administering a combination of compounds selected from Formulas I-X are also contemplated.

Compounds for Treating Cardiac Valve Disease and Pharmaceutically Acceptable Salts and Derivatives Thereof

Compounds of Formula I

Compositions which find use in the methods of the present disclosure can include compounds of Formula I, shown below, which formula encompasses XCT-790 (2E-3-(4-{[2,4-bis(trifluoromethyl)benzyl]oxy}-3-methoxyphenyl)-2-cyano-N-[5-(trifluoromethyl)-1,3,4-thiadiazol-2-yl] acrylamide) and pharmaceutically acceptable salts and derivatives thereof.

In one aspect, the disclosed methods include administration of a compound of Formula I.

(I)

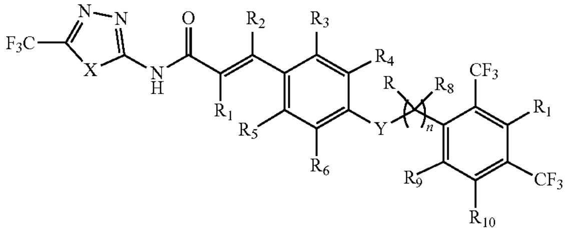

or a pharmaceutically acceptable salt, solvate or prodrug thereof, wherein:

n is an integer from 1 to 8;

X is O or S;

Y is O or S; and each of $R^1$, $R^2$, $R^3$, $R^4$, $R^5$, $R^6$, $R^7$, $R^8$, $R^9$, $R^{10}$ and $R^{11}$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, $—COR^{12}$, $—C(O)OR^{12}$, $—C(O)NR^{12}R^{13}$, $—C{=}NR^{12}$, $—OR^{12}$, $—OC(O)R^{12}$, $—S(O)_t—R^7$, $—NR^{12}R^{13}$, $—NR^{12}C(O)R^{13}$, $—N{=}CR^{12}R^{13}$, wherein t is 0, 1, 2 or 3 and $R^{12}$ and $R^{13}$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen.

In some embodiments, n is 1. In other embodiments, n is 2. In other embodiments, n is 3. In other embodiments, n is 4. In other embodiments, n is 5. In other embodiments, n is 6. In other embodiments, n is 7. In other embodiments, n is 8.

In some embodiments, X is O. In other embodiments, X is S. In some embodiments, Y is O. In other embodiments, Y is S. In some instances, X is O and Y is O. In other instances, X is O and Y is S. In other embodiments, X is S and Y is O. In other embodiments, X is S and Y is S.

In some embodiments, $R^1$ is cyano. In some embodiments, $R^1$ is hydrogen. In other embodiments, $R^1$ is alkyl or substituted alkyl. In other embodiments, $R^1$ is aryl or substituted aryl. In other embodiments, $R^1$ is heterocycloalkyl or substituted heterocycloalkyl. In other embodiments, $R^1$ is heteroaryl or substituted heteroaryl. In other embodiments, $R^1$ is hydroxyl, alkoxyl or substituted alkoxyl. In other embodiments, $R^1$ is acyloxy or substituted acyloxy. In other embodiments, $R^1$ is alkoxylcarbonyl or substituted alkoxycarbonyl. In other embodiments, $R^1$ is acyl or substituted acyl. In other embodiments, $R^1$ is thiol. In other embodiments, $R^1$ is amino or substituted amino. In other embodiments, $R^1$ is aminoacyl or substituted aminoacyl. In other embodiments, $R^1$ is azido. In other embodiments, $R^1$ is carboxyl, substituted carboxyl, carboxyalkyl or substituted carboxyalkyl. In other embodiments, $R^1$ is a halogen, such as —F, —Cl, —Br and —I. In other embodiments, $R^1$ is nitro. In certain embodiments, $R^1$ is naphthyl.

In some embodiments, $R^2$ is hydrogen. In other embodiments, $R^2$ is alkyl or substituted alkyl. In other embodiments, $R^2$ is aryl or substituted aryl. In other embodiments, $R^2$ is heterocycloalkyl or substituted heterocycloalkyl. In other embodiments, $R^2$ is heteroaryl or substituted heteroaryl. In other embodiments, $R^2$ is hydroxyl, alkoxyl or substituted alkoxyl. In other embodiments, $R^2$ is acyloxy or substituted acyloxy. In other embodiments, $R^2$ is alkoxylcarbonyl or substituted alkoxycarbonyl. In other embodiments, $R^2$ is acyl or substituted acyl. In other embodiments, $R^2$ is thiol. In other embodiments, $R^2$ is amino or substituted amino. In other embodiments, $R^2$ is aminoacyl or substituted aminoacyl. In other embodiments, $R^2$ is azido. In other embodiments, $R^2$ is carboxyl, substituted carboxyl, carboxyalkyl or substituted carboxyalkyl. In other embodiments, $R^2$ is cyano. In other embodiments, $R^2$ is a halogen, such as —F, —Cl, —Br and —I. In other embodiments, $R^2$ is nitro.

In some embodiments, $R^3$ is hydrogen. In other embodiments, $R^3$ is alkyl or substituted alkyl. In other embodiments, $R^3$ is aryl or substituted aryl. In other embodiments, $R^3$ is heterocycloalkyl or substituted heterocycloalkyl. In other embodiments, $R^3$ is heteroaryl or substituted heteroaryl. In other embodiments, $R^3$ is hydroxyl, alkoxyl or substituted alkoxyl. In other embodiments, $R^3$ is acyloxy or substituted acyloxy. In other embodiments, $R^3$ is alkoxylcarbonyl or substituted alkoxycarbonyl. In other embodiments, $R^3$ is acyl or substituted acyl. In other embodiments, $R^3$ is thiol. In other embodiments, $R^3$ is amino or substituted amino. In other embodiments, $R^3$ is aminoacyl or substituted aminoacyl. In other embodiments, $R^3$ is azido. In other embodiments, $R^3$ is carboxyl, substituted carboxyl, carboxyalkyl or substituted carboxyalkyl. In other embodiments, $R^3$ is cyano. In other embodiments, $R^3$ is a halogen, such as —F, —Cl, —Br and —I. In other embodiments, $R^3$ is chloro.

In some embodiments, $R^4$ is hydrogen. In other embodiments, $R^4$ is alkyl or substituted alkyl. In other embodiments, $R^4$ is aryl or substituted aryl. In other embodiments, $R^4$ is heterocycloalkyl or substituted heterocycloalkyl. In other embodiments, $R^4$ is heteroaryl or substituted heteroaryl. In other embodiments, $R^4$ is hydroxyl, alkoxyl or substituted alkoxyl. In other embodiments, $R^4$ is acyloxy or substituted acyloxy. In other embodiments, $R^4$ is alkoxylcarbonyl or substituted alkoxycarbonyl. In other embodiments, $R^4$ is acyl or substituted acyl. In other embodiments, $R^4$ is thiol. In other embodiments, $R^4$ is amino or substituted amino. In other embodiments, $R^4$ is aminoacyl or substituted aminoacyl. In other embodiments, $R^4$ is azido. In other embodiments, $R^4$ is carboxyl, substituted carboxyl, carboxyalkyl or substituted carboxyalkyl. In other embodiments, $R^4$ is cyano. In other embodiments, $R^4$ is a halogen, such as —F, —Cl, —Br and —I. In other embodiments, $R^4$ is nitro.

In some embodiments, $R^5$ is hydrogen. In other embodiments, $R^5$ is alkyl or substituted alkyl. In other embodiments, $R^5$ is aryl or substituted aryl. In other embodiments, $R^5$ is heterocycloalkyl or substituted heterocycloalkyl. In other embodiments, $R^5$ is heteroaryl or substituted heteroaryl. In other embodiments, $R^5$ is hydroxyl, alkoxyl or substituted alkoxyl. In other embodiments, $R^5$ is acyloxy or substituted acyloxy. In other embodiments, $R^5$ is alkoxylcarbonyl or substituted alkoxycarbonyl. In other embodiments, $R^5$ is acyl or substituted acyl. In other embodiments, $R^5$ is thiol. In other embodiments, $R^5$ is amino or substituted amino. In other embodiments, $R^5$ is aminoacyl or substituted aminoacyl. In other embodiments, $R^5$ is azido. In other embodiments, $R^5$ is carboxyl, substituted carboxyl, carboxyalkyl or substituted carboxyalkyl. In other embodiments, $R^5$ is cyano. In other embodiments, $R^5$ is a halogen, such as —F, —Cl, —Br and —I. In other embodiments, $R^5$ is nitro.

In some embodiments, $R^6$ is alkoxy, such as methoxy or ethoxy. In other embodiments, $R^6$ is hydrogen. In other embodiments, $R^6$ is alkyl or substituted alkyl. In other embodiments, $R^6$ is aryl or substituted aryl. In other embodiments, $R^6$ is heterocycloalkyl or substituted heterocycloalkyl. In other embodiments, $R^6$ is heteroaryl or substituted heteroaryl. In other embodiments, $R^6$ is hydroxyl, alkoxyl or substituted alkoxyl. In other embodiments, $R^6$ is acyloxy or substituted acyloxy. In other embodiments, $R^6$ is alkoxylcarbonyl or substituted alkoxycarbonyl. In other embodiments, $R^6$ is acyl or substituted acyl. In other embodiments, $R^6$ is thiol. In other embodiments, $R^6$ is amino or substituted amino. In other embodiments, $R^6$ is aminoacyl or substituted aminoacyl. In other embodiments, $R^6$ is azido. In other embodiments, $R^6$ is carboxyl, substituted carboxyl, carboxyalkyl or substituted carboxyalkyl. In other embodiments, $R^6$ is cyano. In other embodiments, $R^6$ is a halogen, such as —F, —Cl, —Br and —I. In other embodiments, $R^6$ is nitro. In certain embodiments, $R^6$ is alkoxylcarbonyl, such as ethoxycarbonyl.

In some embodiments, $R^7$ is hydrogen. In other embodiments, $R^7$ is alkyl or substituted alkyl. In other embodiments, $R^7$ is aryl or substituted aryl. In other embodiments, $R^7$ is heterocycloalkyl or substituted heterocycloalkyl. In other embodiments, $R^7$ is heteroaryl or substituted heteroaryl. In other embodiments, $R^7$ is hydroxyl, alkoxyl or substituted alkoxyl. In other embodiments, $R^7$ is acyloxy or substituted acyloxy. In other embodiments, $R^7$ is alkoxylcarbonyl or substituted alkoxycarbonyl. In other embodiments, $R^7$ is acyl or substituted acyl. In other embodiments, $R^7$ is thiol. In other embodiments, $R^7$ is amino or substituted amino. In other embodiments, $R^7$ is aminoacyl or substituted aminoacyl. In other embodiments, $R^7$ is azido. In other embodiments, $R^7$ is carboxyl, substituted carboxyl, carboxyalkyl or substituted carboxyalkyl. In other embodiments, $R^7$ is cyano. In other embodiments, $R^7$ is a halogen, such as —F, —Cl, —Br and —I. In other embodiments, $R^7$ is nitro. In certain embodiments, $R^7$ is amino.

In some embodiments, $R^8$ is hydrogen. In other embodiments, $R^8$ is alkyl or substituted alkyl. In other embodiments, $R^8$ is aryl or substituted aryl. In other embodiments, $R^8$ is heterocycloalkyl or substituted heterocycloalkyl. In other embodiments, $R^8$ is heteroaryl or substituted heteroaryl. In other embodiments, $R^8$ is hydroxyl, alkoxyl or substituted alkoxyl. In other embodiments, $R^8$ is acyloxy or substituted acyloxy. In other embodiments, $R^8$ is alkoxylcarbonyl or substituted alkoxycarbonyl. In other embodiments, $R^8$ is acyl or substituted acyl. In other embodiments, $R^8$ is thiol. In other embodiments, $R^8$ is amino or substituted amino. In other embodiments, $R^8$ is aminoacyl or substituted aminoacyl. In other embodiments, $R^8$ is azido. In other embodiments, $R^8$ is carboxyl, substituted carboxyl, carboxyalkyl or substituted carboxyalkyl. In other embodiments, $R^8$ is cyano. In other embodiments, $R^8$ is a halogen, such as —F, —Cl, —Br and —I. In other embodiments, $R^8$ is nitro. In certain embodiments, $R^8$ is amino.

In some embodiments, $R^9$ is hydrogen. In other embodiments, $R^9$ is alkyl or substituted alkyl. In other embodiments, $R^9$ is aryl or substituted aryl. In other embodiments, $R^9$ is heterocycloalkyl or substituted heterocycloalkyl. In other embodiments, $R^9$ is heteroaryl or substituted heteroaryl. In other embodiments, $R^9$ is hydroxyl, alkoxyl or substituted alkoxyl. In other embodiments, $R^9$ is acyloxy or substituted acyloxy. In other embodiments, $R^9$ is alkoxylcarbonyl or substituted alkoxycarbonyl. In other embodiments, $R^9$ is acyl or substituted acyl. In other embodiments, $R^9$ is thiol. In other embodiments, $R^9$ is amino or substituted amino. In other embodiments, $R^9$ is aminoacyl or substituted aminoacyl. In other embodiments, $R^9$ is azido. In other embodiments, $R^9$ is carboxyl, substituted carboxyl, carboxyalkyl or substituted carboxyalkyl. In other embodiments, $R^9$ is cyano. In other embodiments, $R^9$ is a halogen, such as —F, —Cl, —Br and —I. In other embodiments, $R^9$ is nitro. In certain embodiments, $R^7$ is amino.

In some embodiments, $R^{10}$ is hydrogen. In other embodiments, $R^{10}$ is alkyl or substituted alkyl. In other embodiments, $R^{10}$ is aryl or substituted aryl. In other embodiments, $R^{10}$ is heterocycloalkyl or substituted heterocycloalkyl. In other embodiments, $R^{10}$ is heteroaryl or substituted heteroaryl. In other embodiments, $R^{10}$ is hydroxyl, alkoxyl or substituted alkoxyl. In other embodiments, $R^{10}$ is acyloxy or substituted acyloxy. In other embodiments, $R^{10}$ is alkoxylcarbonyl or substituted alkoxycarbonyl. In other embodiments, $R^{10}$ is acyl or substituted acyl. In other embodiments, $R^{10}$ is thiol. In other embodiments, $R^{10}$ is amino or substituted amino. In other embodiments, $R^{10}$ is aminoacyl or substituted aminoacyl. In other embodiments, $R^{10}$ is azido. In other embodiments, $R^{10}$ is carboxyl, substituted carboxyl, carboxyalkyl or substituted carboxyalkyl. In other embodiments, $R^{10}$ is cyano. In other embodiments, $R^{10}$ is a halogen, such as —F, —Cl, —Br and —I. In other embodiments, $R^{10}$ is nitro. In certain embodiments, $R^{10}$ is amino.

In some embodiments, $R^{11}$ is hydrogen. In other embodiments, $R^{11}$ is alkyl or substituted alkyl. In other embodiments, $R^{11}$ is aryl or substituted aryl. In other embodiments, $R^{11}$ is heterocycloalkyl or substituted heterocycloalkyl. In other embodiments, $R^{11}$ is heteroaryl or substituted heteroaryl. In other embodiments, $R^{11}$ is hydroxyl, alkoxyl or substituted alkoxyl. In other embodiments, $R^{11}$ is acyloxy or substituted acyloxy. In other embodiments, $R^{11}$ is alkoxylcarbonyl or substituted alkoxycarbonyl. In other embodiments, $R^{11}$ is acyl or substituted acyl. In other embodiments, $R^{11}$ is thiol. In other embodiments, $R^{11}$ is amino or substituted amino. In other embodiments, $R^{11}$ is aminoacyl or substituted aminoacyl. In other embodiments, $R^{11}$ is azido. In other embodiments, $R^{11}$ is carboxyl, substituted carboxyl, carboxyalkyl or substituted carboxyalkyl. In other embodiments, $R^{11}$ is cyano. In other embodiments, $R^{11}$ is a halogen, such as —F, —Cl, —Br and —I. In other embodiments, $R^{11}$ is nitro. In certain embodiments, $R^{11}$ is amino.

In certain embodiments, a compound of interest and salts or solvates or stereoisomers thereof, include:

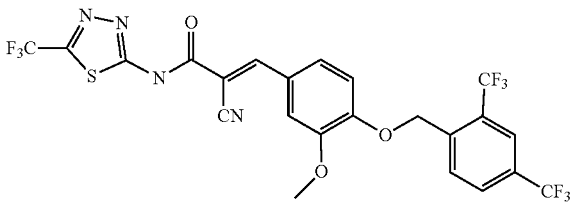

("XCT-790") (2E-3-(4-{[2,4-bis(trifluoromethyl)benzyl]oxy}-3-methoxyphenyl)-2-cyano-N-[5-(trifluoromethyl)-1,3,4-thiadiazol-2-yl]acrylamide).

Compounds of Formula H

Compositions which find use in the methods of the present disclosure can include compounds of Formula II, shown below, which formula encompasses TG-003 ((Z)-1-(3-ethyl-5-methoxy-2,3-dihydrobenzothiazol-2-ylidene) propan-2-one) and pharmaceutically acceptable salts and derivatives thereof.

In one aspect, the disclosed methods include administration of a compound of Formula II:

(II)

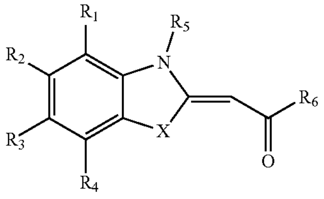

or a pharmaceutically acceptable salt, solvate or prodrug thereof, wherein:

X is O or S;

each of $R^1$, $R^2$, $R^3$, $R^4$, $R^5$ and $R^6$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, $—COR^{12}$, $—C(O)OR^{12}$, $—C(O)NR^{12}R^{13}$, $—C{=}NR^{12}$, $—OR^{12}$, $—OC(O)R^{12}$, $—S(O)_t—R^7$, $—NR^{12}R^{13}$, $—NR^{12}C(O)R^{13}$, $—N{=}CR^{12}R^{13}$, wherein t is 0, 1, 2 or 3 and $R^{12}$ and $R^{13}$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen.

In some embodiments, X is O. In other embodiments, X is S.

In some embodiments, $R^1$ is hydrogen. In some embodiments, $R^1$ is cyano. In other embodiments, $R^1$ is alkyl or substituted alkyl. In other embodiments, $R^1$ is aryl or substituted aryl. In other embodiments, $R^1$ is heterocycloalkyl or substituted heterocycloalkyl. In other embodiments, $R^1$ is heteroaryl or substituted heteroaryl. In other embodiments, $R^1$ is hydroxyl, alkoxyl or substituted alkoxyl. In other embodiments, $R^1$ is acyloxy or substituted acyloxy. In other embodiments, $R^1$ is alkoxylcarbonyl or substituted alkoxycarbonyl. In other embodiments, $R^1$ is acyl or substituted acyl. In other embodiments, $R^1$ is thiol. In other embodiments, $R^1$ is amino or substituted amino. In other embodiments, $R^1$ is aminoacyl or substituted aminoacyl. In other embodiments, $R^1$ is azido. In other embodiments, $R^1$ is carboxyl, substituted carboxyl, carboxyalkyl or substituted carboxyalkyl. In other embodiments, $R^1$ is a halogen, such as —F, —Cl, —Br and —I. In other embodiments, $R^1$ is nitro. In certain embodiments, $R^1$ is naphthyl.

In some embodiments, $R^2$ is alkoxy, such as methoxy or ethoxy. In other embodiments, $R^2$ is hydrogen. In other embodiments, $R^2$ is alkyl or substituted alkyl. In other embodiments, $R^2$ is aryl or substituted aryl. In other embodiments, $R^2$ is heterocycloalkyl or substituted heterocycloalkyl. In other embodiments, $R^2$ is heteroaryl or substituted heteroaryl. In other embodiments, $R^2$ is hydroxyl, alkoxyl or substituted alkoxyl. In other embodiments, $R^2$ is acyloxy or substituted acyloxy. In other embodiments, $R^2$ is alkoxylcarbonyl or substituted alkoxycarbonyl. In other embodiments, $R^2$ is acyl or substituted acyl. In other embodiments, $R^2$ is thiol. In other embodiments, $R^2$ is amino or substituted amino. In other embodiments, $R^2$ is aminoacyl or substituted aminoacyl. In other embodiments, $R^2$ is azido. In other embodiments, $R^2$ is carboxyl, substituted carboxyl, carboxyalkyl or substituted carboxyalkyl. In other embodiments, $R^2$ is cyano. In other embodiments, $R^2$ is a halogen, such as —F, —Cl, —Br and —I. In other embodiments, $R^2$ is nitro.

In some embodiments, $R^3$ is hydrogen. In other embodiments, $R^3$ is alkyl or substituted alkyl. In other embodiments, $R^3$ is aryl or substituted aryl. In other embodiments, $R^3$ is heterocycloalkyl or substituted heterocycloalkyl. In other embodiments, $R^3$ is heteroaryl or substituted heteroaryl. In other embodiments, $R^3$ is hydroxyl, alkoxyl or substituted alkoxyl. In other embodiments, $R^3$ is acyloxy or substituted acyloxy. In other embodiments, $R^3$ is alkoxylcarbonyl or substituted alkoxycarbonyl. In other embodiments, $R^3$ is acyl or substituted acyl. In other embodiments, $R^3$ is thiol. In other embodiments, $R^3$ is amino or substituted amino. In other embodiments, $R^3$ is aminoacyl or substituted aminoacyl. In other embodiments, $R^3$ is azido. In other embodiments, $R^3$ is carboxyl, substituted carboxyl, carboxyalkyl or substituted carboxyalkyl. In other embodiments, $R^3$ is cyano. In other embodiments, $R^3$ is a halogen, such as —F, —Cl, —Br and —I. In other embodiments, $R^3$ is chloro.

In some embodiments, $R^4$ is hydrogen. In other embodiments, $R^4$ is alkyl or substituted alkyl. In other embodiments, $R^4$ is aryl or substituted aryl. In other embodiments, $R^4$ is heterocycloalkyl or substituted heterocycloalkyl. In other embodiments, $R^4$ is heteroaryl or substituted heteroaryl. In other embodiments, $R^4$ is hydroxyl, alkoxyl or substituted alkoxyl. In other embodiments, $R^4$ is acyloxy or substituted acyloxy. In other embodiments, $R^4$ is alkoxylcarbonyl or substituted alkoxycarbonyl. In other embodiments, $R^4$ is acyl or substituted acyl. In other embodiments, $R^4$ is thiol. In other embodiments, $R^4$ is amino or substituted amino. In other embodiments, $R^4$ is aminoacyl or substituted aminoacyl. In other embodiments, $R^4$ is azido. In other embodiments, $R^4$ is carboxyl, substituted carboxyl, carboxyalkyl or substituted carboxyalkyl. In other embodiments, $R^4$ is cyano. In other embodiments, $R^4$ is a halogen, such as —F, —Cl, —Br and —I. In other embodiments, $R^4$ is nitro.

In some embodiments, $R^5$ is alkyl or substituted alkyl, such as methyl, ethyl or propyl. In certain instances, $R^5$ is ethyl. In other embodiments, $R^5$ is hydrogen. In other embodiments, In other embodiments, $R^5$ is aryl or substituted aryl. In other embodiments, $R^5$ is heterocycloalkyl or substituted heterocycloalkyl. In other embodiments, $R^5$ is heteroaryl or substituted heteroaryl. In other embodiments, $R^5$ is hydroxyl, alkoxyl or substituted alkoxyl. In other embodiments, $R^5$ is acyloxy or substituted acyloxy. In other embodiments, $R^5$ is alkoxylcarbonyl or substituted alkoxycarbonyl. In other embodiments, $R^5$ is acyl or substituted acyl. In other embodiments, $R^5$ is thiol. In other embodiments, $R^5$ is amino or substituted amino. In other embodiments, $R^5$ is aminoacyl or substituted aminoacyl. In other embodiments, $R^5$ is azido. In other embodiments, $R^5$ is carboxyl, substituted carboxyl, carboxyalkyl or substituted carboxyalkyl. In other embodiments, $R^5$ is cyano. In other embodiments, $R^5$ is a halogen, such as —F, —Cl, —Br and —I. In other embodiments, $R^5$ is nitro.

In some embodiments, $R^6$ is alkyl or substituted alkyl, such as methyl, ethyl or propyl. In certain instances, $R^6$ is methyl. In other embodiments, $R^6$ is hydrogen. In other embodiments, In other embodiments, $R^6$ is aryl or substituted aryl. In other embodiments, $R^6$ is heterocycloalkyl or substituted heterocycloalkyl. In other embodiments, $R^6$ is heteroaryl or substituted heteroaryl. In other embodiments, $R^6$ is hydroxyl, alkoxyl or substituted alkoxyl. In other embodiments, $R^6$ is acyloxy or substituted acyloxy. In other embodiments, $R^6$ is alkoxylcarbonyl or substituted alkoxycarbonyl. In other embodiments, $R^6$ is acyl or substituted acyl. In other embodiments, $R^6$ is thiol. In other embodiments, $R^6$ is amino or substituted amino. In other embodiments, $R^6$ is aminoacyl or substituted aminoacyl. In other embodiments, $R^6$ is azido. In other embodiments, $R^6$ is carboxyl, substituted carboxyl, carboxyalkyl or substituted carboxyalkyl. In other embodiments, $R^6$ is cyano. In other embodiments, $R^6$ is a halogen, such as —F, —Cl, —Br and —I. In other embodiments, $R^6$ is nitro.

In certain embodiments, a compound of interest and salts or solvates or stereoisomers thereof, include:

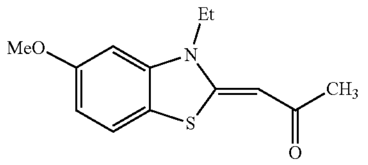 [SMILES: CCN1/C(=C/C(C)=O)Sc2ccc(OC)cc21]

("TG-003") ((Z)-1-(3-ethyl-5-methoxy-2,3-dihydrobenzothiazol-2-ylidene)propan-2-one)

Compounds of Formula III

Compositions which find use in the methods of the present disclosure can include compounds of Formula III, shown below, which formula encompasses GSK-837149A (4,4'-(carbonyldiimino)bis[N-(4-methyl-2-pyrimidinyl)-benzenesulfonamide) and pharmaceutically acceptable salts and derivatives thereof.

In one aspect, the disclosed methods include administration of a compound of Formula III:

(III)

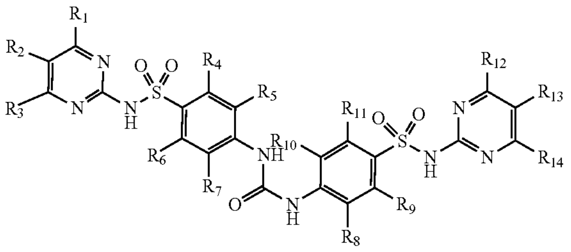

or a pharmaceutically acceptable salt, solvate or prodrug thereof, wherein:

each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —$COR^{15}$, —$C(O)OR^{15}$, —$C(O)NR^{15}R^{16}$, —$C{=}NR^{15}$, —$OR^{15}$, —$OC(O)R^{15}$, —$S(O)_t$—$R^{15}$, —$NR^{15}R^{16}$, —$NR^{15}C(O)R^{16}$, —$N{=}CR^{15}R^{16}$, wherein t is 0, 1, 2 or 3 and $R^{15}$ and $R^{15}$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen.

In some embodiments, $R^1$ is hydrogen. In other embodiments, $R^1$ is alkyl or substituted alkyl. In other embodiments, $R^1$ is aryl or substituted aryl. In other embodiments, $R^1$ is heterocycloalkyl or substituted heterocycloalkyl. In other embodiments, $R^1$ is heteroaryl or substituted heteroaryl. In other embodiments, $R^1$ is hydroxyl, alkoxyl or substituted alkoxyl. In other embodiments, $R^1$ is acyloxy or substituted acyloxy. In other embodiments, $R^1$ is alkoxylcarbonyl or substituted alkoxycarbonyl. In other embodiments, $R^1$ is acyl or substituted acyl. In other embodiments, $R^1$ is thiol. In other embodiments, $R^1$ is amino or substituted amino. In other embodiments, $R^1$ is aminoacyl or substituted aminoacyl. In other embodiments, $R^1$ is azido. In other embodiments, $R^1$ is carboxyl, substituted carboxyl, carboxyalkyl or substituted carboxyalkyl. In other embodiments, $R^1$ is a halogen, such as —F, —Cl, —Br and —I. In other embodiments, $R^1$ is nitro. In certain embodiments, $R^1$ is naphthyl.

In some embodiments, $R^2$ is hydrogen. In other embodiments, $R^2$ is alkyl or substituted alkyl. In other embodiments, $R^2$ is aryl or substituted aryl. In other embodiments, $R^2$ is heterocycloalkyl or substituted heterocycloalkyl. In other embodiments, $R^2$ is heteroaryl or substituted heteroaryl. In other embodiments, $R^2$ is hydroxyl, alkoxyl or substituted alkoxyl. In other embodiments, $R^2$ is acyloxy or substituted acyloxy. In other embodiments, $R^2$ is alkoxylcarbonyl or substituted alkoxycarbonyl. In other embodiments, $R^2$ is acyl or substituted acyl. In other embodiments, $R^2$ is thiol. In other embodiments, $R^2$ is amino or substituted amino. In other embodiments, $R^2$ is aminoacyl or substituted aminoacyl. In other embodiments, $R^2$ is azido. In other embodiments, $R^2$ is carboxyl, substituted carboxyl, carboxyalkyl or substituted carboxyalkyl. In other embodiments, $R^2$ is cyano. In other embodiments, $R^2$ is a halogen, such as —F, —Cl, —Br and —I. In other embodiments, $R^2$ is nitro.

In some embodiments, $R^3$ is alkyl or substituted alkyl, such as methyl, ethyl or propyl. In certain instances, $R^3$ is methyl. In other embodiments, $R^3$ is hydrogen. In other embodiments, $R^3$ is aryl or substituted aryl. In other embodiments, $R^3$ is heterocycloalkyl or substituted heterocycloalkyl. In other embodiments, $R^3$ is heteroaryl or substituted heteroaryl. In other embodiments, $R^3$ is hydroxyl, alkoxyl or substituted alkoxyl. In other embodiments, $R^3$ is acyloxy or substituted acyloxy. In other embodiments, $R^3$ is alkoxylcarbonyl or substituted alkoxycarbonyl. In other embodiments, $R^3$ is acyl or substituted acyl. In other embodiments, $R^3$ is thiol. In other embodiments, $R^3$ is amino or substituted amino. In other embodiments, $R^3$ is aminoacyl or substituted aminoacyl. In other embodiments, $R^3$ is azido. In other embodiments, $R^3$ is carboxyl, substituted carboxyl, carboxyalkyl or substituted carboxyalkyl. In other embodiments, $R^3$ is cyano. In other embodiments, $R^3$ is a halogen, such as —F, —Cl, —Br and —I. In other embodiments, $R^3$ is chloro.

In some embodiments, $R^4$ is hydrogen. In other embodiments, $R^4$ is alkyl or substituted alkyl. In other embodiments, $R^4$ is aryl or substituted aryl. In other embodiments, $R^4$ is heterocycloalkyl or substituted heterocycloalkyl. In other embodiments, $R^4$ is heteroaryl or substituted heteroaryl. In other embodiments, $R^4$ is hydroxyl, alkoxyl or substituted alkoxyl. In other embodiments, $R^4$ is acyloxy or substituted acyloxy. In other embodiments, $R^4$ is alkoxylcarbonyl or substituted alkoxycarbonyl. In other embodiments, $R^4$ is acyl or substituted acyl. In other embodiments, $R^4$ is thiol. In other embodiments, $R^4$ is amino or substituted amino. In other embodiments, $R^4$ is aminoacyl or substituted aminoacyl. In other embodiments, $R^4$ is azido. In other embodiments, $R^4$ is carboxyl, substituted carboxyl, carboxyalkyl or substituted carboxyalkyl. In other embodiments, $R^4$ is cyano. In other embodiments, $R^4$ is a halogen, such as —F, —Cl, —Br and —I. In other embodiments, $R^4$ is nitro.

In some embodiments, $R^5$ is hydrogen. In other embodiments, $R^5$ is alkyl or substituted alkyl. In other embodiments, $R^5$ is aryl or substituted aryl. In other embodiments, $R^5$ is heterocycloalkyl or substituted heterocycloalkyl. In other embodiments, $R^5$ is heteroaryl or substituted heteroaryl. In other embodiments, $R^5$ is hydroxyl, alkoxyl or substituted alkoxyl. In other embodiments, $R^5$ is acyloxy or substituted acyloxy. In other embodiments, $R^5$ is alkoxylcarbonyl or substituted alkoxycarbonyl. In other embodiments, $R^5$ is acyl or substituted acyl. In other embodiments, $R^5$ is thiol. In other embodiments, $R^5$ is amino or substituted amino. In other embodiments, $R^5$ is aminoacyl or substituted aminoacyl. In other embodiments, $R^5$ is azido. In other embodiments, $R^5$ is carboxyl, substituted carboxyl, carboxyalkyl or substituted carboxyalkyl. In other embodiments, $R^5$ is cyano. In other embodiments, $R^5$ is a halogen, such as —F, —Cl, —Br and —I. In other embodiments, $R^5$ is nitro.

In some embodiments, $R^6$ is alkoxy, such as methoxy or ethoxy. In other embodiments, $R^6$ is hydrogen. In other embodiments, $R^6$ is alkyl or substituted alkyl. In other embodiments, $R^6$ is aryl or substituted aryl. In other embodiments, $R^6$ is heterocycloalkyl or substituted heterocycloalkyl. In other embodiments, $R^6$ is heteroaryl or substituted heteroaryl. In other embodiments, $R^6$ is hydroxyl, alkoxyl or substituted alkoxyl. In other embodiments, $R^6$ is acyloxy or substituted acyloxy. In other embodiments, $R^6$ is alkoxylcarbonyl or substituted alkoxycarbonyl. In other embodiments, $R^6$ is acyl or substituted acyl. In other embodiments, $R^6$ is thiol. In other embodiments, $R^6$ is amino or substituted amino. In other embodiments, $R^6$ is aminoacyl or substituted aminoacyl. In other embodiments, $R^6$ is azido. In other embodiments, $R^6$ is carboxyl, substituted carboxyl, carboxyalkyl or substituted carboxyalkyl. In other embodiments, $R^6$ is cyano. In other embodiments, $R^6$ is a halogen, such as —F, —Cl, —Br and —I. In other embodiments, $R^6$ is nitro. In certain embodiments, $R^6$ is alkoxylcarbonyl, such as ethoxycarbonyl.

In some embodiments, $R^7$ is hydrogen. In other embodiments, $R^7$ is alkyl or substituted alkyl. In other embodiments, $R^7$ is aryl or substituted aryl. In other embodiments, $R^7$ is heterocycloalkyl or substituted heterocycloalkyl. In other embodiments, $R^7$ is heteroaryl or substituted heteroaryl. In other embodiments, $R^7$ is hydroxyl, alkoxyl or substituted alkoxyl. In other embodiments, $R^7$ is acyloxy or substituted acyloxy. In other embodiments, $R^7$ is alkoxylcarbonyl or substituted alkoxycarbonyl. In other embodiments, $R^7$ is acyl or substituted acyl. In other embodiments, $R^7$ is thiol. In other embodiments, $R^7$ is amino or substituted amino. In other embodiments, $R^7$ is aminoacyl or substituted aminoacyl. In other embodiments, $R^7$ is azido. In other embodiments, $R^7$ is carboxyl, substituted carboxyl, carboxyalkyl or substituted carboxyalkyl. In other embodiments, $R^7$ is cyano. In other embodiments, $R^7$ is a halogen, such as —F, —Cl, —Br and —I. In other embodiments, $R^7$ is nitro. In certain embodiments, $R^7$ is amino.

In some embodiments, $R^8$ is hydrogen. In other embodiments, $R^8$ is alkyl or substituted alkyl. In other embodiments, $R^8$ is aryl or substituted aryl. In other embodiments, $R^8$ is heterocycloalkyl or substituted heterocycloalkyl. In other embodiments, $R^8$ is heteroaryl or substituted heteroaryl. In other embodiments, $R^8$ is hydroxyl, alkoxyl or substituted alkoxyl. In other embodiments, $R^8$ is acyloxy or substituted acyloxy. In other embodiments, $R^8$ is alkoxylcarbonyl or substituted alkoxycarbonyl. In other embodiments, $R^8$ is acyl or substituted acyl. In other embodiments, $R^8$ is thiol. In other embodiments, $R^8$ is amino or substituted amino. In other embodiments, $R^8$ is aminoacyl or substituted aminoacyl. In other embodiments, $R^8$ is azido. In other embodiments, $R^8$ is carboxyl, substituted carboxyl, carboxyalkyl or substituted carboxyalkyl. In other embodiments, $R^8$ is cyano. In other embodiments, $R^8$ is a halogen, such as —F, —Cl, —Br and —I. In other embodiments, $R^8$ is nitro. In certain embodiments, $R^8$ is amino.

In some embodiments, $R^9$ is hydrogen. In other embodiments, $R^9$ is alkyl or substituted alkyl. In other embodiments, $R^9$ is aryl or substituted aryl. In other embodiments, $R^9$ is heterocycloalkyl or substituted heterocycloalkyl. In other embodiments, $R^9$ is heteroaryl or substituted heteroaryl. In other embodiments, $R^9$ is hydroxyl, alkoxyl or substituted alkoxyl. In other embodiments, $R^9$ is acyloxy or substituted acyloxy. In other embodiments, $R^9$ is alkoxylcarbonyl or substituted alkoxycarbonyl. In other embodiments, $R^9$ is acyl or substituted acyl. In other embodiments, $R^9$ is thiol. In other embodiments, $R^9$ is amino or substituted amino. In other embodiments, $R^9$ is aminoacyl or substituted aminoacyl. In other embodiments, $R^9$ is azido. In other embodiments, $R^9$ is carboxyl, substituted carboxyl, carboxyalkyl or substituted carboxyalkyl. In other embodiments, $R^9$ is cyano. In other embodiments, $R^9$ is a halogen, such as —F, —Cl, —Br and —I. In other embodiments, $R^9$ is nitro. In certain embodiments, $R^7$ is amino.

In some embodiments, $R^{10}$ is hydrogen. In other embodiments, $R^{10}$ is alkyl or substituted alkyl. In other embodiments, $R^{10}$ is aryl or substituted aryl. In other embodiments, $R^{10}$ is heterocycloalkyl or substituted heterocycloalkyl. In other embodiments, $R^{10}$ is heteroaryl or substituted heteroaryl. In other embodiments, $R^{10}$ is hydroxyl, alkoxyl or substituted alkoxyl. In other embodiments, $R^{10}$ is acyloxy or substituted acyloxy. In other embodiments, $R^{10}$ is alkoxylcarbonyl or substituted alkoxycarbonyl. In other embodiments, $R^{10}$ is acyl or substituted acyl. In other embodiments, $R^{10}$ is thiol. In other embodiments, $R^{10}$ is amino or substituted amino. In other embodiments, $R^{10}$ is aminoacyl or substituted aminoacyl. In other embodiments, $R^{10}$ is azido. In other embodiments, $R^{10}$ is carboxyl, substituted carboxyl, carboxyalkyl or substituted carboxyalkyl. In other embodiments, $R^{10}$ is cyano. In other embodiments, $R^{10}$ is a halogen, such as —F, —Cl, —Br and —I. In other embodiments, $R^{10}$ is nitro. In certain embodiments, $R^{10}$ is amino.

In some embodiments, $R^{11}$ is hydrogen. In other embodiments, $R^{11}$ is alkyl or substituted alkyl. In other embodiments, $R^{11}$ is aryl or substituted aryl. In other embodiments, $R^{11}$ is heterocycloalkyl or substituted heterocycloalkyl. In other embodiments, $R^{11}$ is heteroaryl or substituted heteroaryl. In other embodiments, $R^{11}$ is hydroxyl, alkoxyl or substituted alkoxyl. In other embodiments, $R^{11}$ is acyloxy or substituted acyloxy. In other embodiments, $R^{11}$ is alkoxylcarbonyl or substituted alkoxycarbonyl. In other embodiments, $R^{11}$ is acyl or substituted acyl. In other embodiments, $R^{11}$ is thiol. In other embodiments, $R^{11}$ is amino or substituted amino. In other embodiments, $R^{11}$ is aminoacyl or substituted aminoacyl. In other embodiments, $R^{11}$ is azido. In other embodiments, $R^{11}$ is carboxyl, substituted carboxyl, carboxyalkyl or substituted carboxyalkyl. In other embodiments, $R^{11}$ is cyano. In other embodiments, $R^{11}$ is a halogen, such as —F, —Cl, —Br and —I. In other embodiments, $R^{11}$ is nitro. In certain embodiments, $R^{11}$ is amino.

In some embodiments, $R^{12}$ is alkyl or substituted alkyl, such as methyl, ethyl or propyl. In certain instances, $R^{12}$ is methyl. In other embodiments, $R^{12}$ is hydrogen. In other embodiments, $R^{12}$ is aryl or substituted aryl. In other embodiments, $R^{12}$ is heterocycloalkyl or substituted heterocycloalkyl. In other embodiments, $R^{12}$ is heteroaryl or substituted heteroaryl. In other embodiments, $R^{12}$ is hydroxyl, alkoxyl or substituted alkoxyl. In other embodiments, $R^{12}$ is acyloxy or substituted acyloxy. In other embodiments, $R^{12}$ is alkoxylcarbonyl or substituted alkoxycarbonyl. In other embodiments, $R^{12}$ is acyl or substituted acyl. In other embodiments, $R^{12}$ is thiol. In other embodiments, $R^{12}$ is amino or substituted amino. In other embodiments, $R^{12}$ is aminoacyl or substituted aminoacyl. In other embodiments, $R^{12}$ is azido. In other embodiments, $R^{12}$ is carboxyl, substituted carboxyl, carboxyalkyl or substituted carboxyalkyl. In other embodiments, $R^{12}$ is cyano. In other embodiments, $R^{12}$ is a halogen, such as —F, —Cl, —Br and —I. In other embodiments, $R^{12}$ is chloro.

In some embodiments, $R^{13}$ is hydrogen. In other embodiments, $R^{13}$ is alkyl or substituted alkyl. In other embodiments, $R^{13}$ is aryl or substituted aryl. In other embodiments, $R^{13}$ is heterocycloalkyl or substituted heterocycloalkyl. In other embodiments, $R^{13}$ is heteroaryl or substituted heteroaryl. In other embodiments, $R^{13}$ is hydroxyl, alkoxyl or substituted alkoxyl. In other embodiments, $R^{13}$ is acyloxy or substituted acyloxy. In other embodiments, $R^{13}$ is alkoxylcarbonyl or substituted alkoxycarbonyl. In other embodiments, $R^{13}$ is acyl or substituted acyl. In other embodiments, $R^{13}$ is thiol. In other embodiments, $R^{13}$ is amino or substituted amino. In other embodiments, $R^{13}$ is aminoacyl or substituted aminoacyl. In other embodiments, $R^{13}$ is azido. In other embodiments, $R^{13}$ is carboxyl, substituted carboxyl, carboxyalkyl or substituted carboxyalkyl. In other embodiments, $R^{13}$ is cyano. In other embodiments, $R^{13}$ is a halogen, such as —F, —Cl, —Br and —I. In other embodiments, $R^{13}$ is nitro. In certain embodiments, $R^{13}$ is amino.

In some embodiments, $R^{14}$ is hydrogen. In other embodiments, $R^{14}$ is alkyl or substituted alkyl. In other embodiments, $R^{14}$ is aryl or substituted aryl. In other embodiments, $R^{14}$ is heterocycloalkyl or substituted heterocycloalkyl. In other embodiments, $R^{14}$ is heteroaryl or substituted heteroaryl. In other embodiments, $R^{14}$ is hydroxyl, alkoxyl or substituted alkoxyl. In other embodiments, $R^{14}$ is acyloxy or substituted acyloxy. In other embodiments, $R^{14}$ is alkoxylcarbonyl or substituted alkoxycarbonyl. In other embodiments, $R^{14}$ is acyl or substituted acyl. In other embodiments, $R^{14}$ is thiol. In other embodiments, $R^{14}$ is amino or substituted amino. In other embodiments, $R^{14}$ is aminoacyl or substituted aminoacyl. In other embodiments, $R^{14}$ is azido. In other embodiments, $R^{14}$ is carboxyl, substituted carboxyl, carboxyalkyl or substituted carboxyalkyl. In other embodiments, $R^{14}$ is cyano. In other embodiments, $R^{14}$ is a halogen, such as —F, —Cl, —Br and —I. In other embodiments, $R^{14}$ is nitro. In certain embodiments, $R^{14}$ is amino.

In certain embodiments, a compound of interest and salts or solvates or stereoisomers thereof, include:

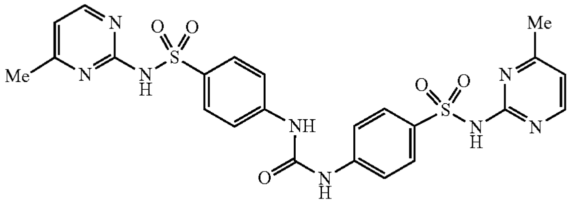 [SMILES: Cc1ccnc(NS(=O)(=O)c2ccc(NC(=O)Nc3ccc(S(=O)(=O)Nc4nccc(C)n4)cc3)cc2)n1]

("GSK-837149A") (4,4'-(carbonyldiimino)bis[N-(4-methyl-2-pyrimidinyl)-benzenesulfonamide)

Compounds of Formula IV

Compositions which find use in the methods of the present disclosure can include compounds of Formula IV, shown below, which formula encompasses Naloxone ((4R,4aS,7aR,12bS)-4a,9-dihydroxy-3-prop-2-enyl-2,4,5,6,7a,13-hexahydro-1H-4,12-methanobenzofuro[3,2-e]isoquinoline-7-one) and pharmaceutically acceptable salts and derivatives thereof.

In one aspect, the disclosed methods include administration of a compound of Formula IV:

(IV)

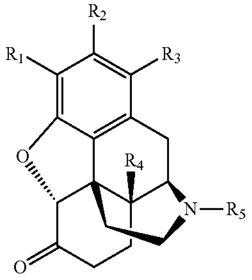

or a pharmaceutically acceptable salt, solvate or prodrug thereof, wherein:

each of $R^1$, $R^2$, $R^3$, $R^4$ and $R^5$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, $—COR^{15}$, $—C(O)OR^{15}$, $—C(O)NR^{15}R^{16}$, $—C{=}NR^{15}$, $—OR^{15}$, $—OC(O)R^{15}$, $—S(O)_t—R^{15}$, $—NR^{15}R^{16}$, $—NR^{15}C(O)R^{16}$, $—N{=}CR^{15}R^{16}$, wherein t is 0, 1, 2 or 3 and $R^{15}$ and $R^{15}$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen.

In some embodiments, $R^1$ is hydroxyl. In other embodiments, $R^1$ is hydrogen. In other embodiments, $R^1$ is alkyl or substituted alkyl. In other embodiments, $R^1$ is aryl or substituted aryl. In other embodiments, $R^1$ is heterocycloalkyl or substituted heterocycloalkyl. In other embodiments, $R^1$ is heteroaryl or substituted heteroaryl. In other embodiments, $R^1$ is alkoxyl or substituted alkoxyl. In other embodiments, $R^1$ is acyloxy or substituted acyloxy. In other embodiments, $R^1$ is alkoxylcarbonyl or substituted alkoxycarbonyl. In other embodiments, $R^1$ is acyl or substituted acyl. In other embodiments, $R^1$ is thiol. In other embodiments, $R^1$ is amino or substituted amino. In other embodiments, $R^1$ is aminoacyl or substituted aminoacyl. In other embodiments, $R^1$ is azido. In other embodiments, $R^1$ is carboxyl, substituted carboxyl, carboxyalkyl or substituted carboxyalkyl. In other embodiments, $R^1$ is a halogen, such as —F, —Cl, —Br and —I. In other embodiments, $R^1$ is nitro. In certain embodiments, $R^1$ is naphthyl.

In some embodiments, $R^2$ is hydrogen. In other embodiments, $R^2$ is alkyl or substituted alkyl. In other embodiments, $R^2$ is aryl or substituted aryl. In other embodiments, $R^2$ is heterocycloalkyl or substituted heterocycloalkyl. In other embodiments, $R^2$ is heteroaryl or substituted heteroaryl. In other embodiments, $R^2$ is hydroxyl, alkoxyl or substituted alkoxyl. In other embodiments, $R^2$ is acyloxy or substituted acyloxy. In other embodiments, $R^2$ is alkoxylcarbonyl or substituted alkoxycarbonyl. In other embodiments, $R^2$ is acyl or substituted acyl. In other embodiments, $R^2$ is thiol. In other embodiments, $R^2$ is amino or substituted amino. In other embodiments, $R^2$ is aminoacyl or substituted aminoacyl. In other embodiments, $R^2$ is azido. In other embodiments, $R^2$ is carboxyl, substituted carboxyl, carboxyalkyl or substituted carboxyalkyl. In other embodiments, $R^2$ is cyano. In other embodiments, $R^2$ is a halogen, such as —F, —Cl, —Br and —I. In other embodiments, $R^2$ is nitro.

In some embodiments, $R^3$ is alkyl or substituted alkyl, such as methyl, ethyl or propyl. In certain instances, $R^3$ is methyl. In other embodiments, $R^3$ is hydrogen. In other embodiments, $R^3$ is aryl or substituted aryl. In other embodiments, $R^3$ is heterocycloalkyl or substituted heterocycloalkyl. In other embodiments, $R^3$ is heteroaryl or substituted heteroaryl. In other embodiments, $R^3$ is hydroxyl, alkoxyl or substituted alkoxyl. In other embodiments, $R^3$ is acyloxy or substituted acyloxy. In other embodiments, $R^3$ is alkoxylcarbonyl or substituted alkoxycarbonyl. In other embodiments, $R^3$ is acyl or substituted acyl. In other embodiments, $R^3$ is thiol. In other embodiments, $R^3$ is amino or substituted amino. In other embodiments, $R^3$ is aminoacyl or substituted aminoacyl. In other embodiments, $R^3$ is azido. In other embodiments, $R^3$ is carboxyl, substituted carboxyl, carboxyalkyl or substituted carboxyalkyl. In other embodiments, $R^3$ is cyano. In other embodiments, $R^3$ is a halogen, such as —F, —Cl, —Br and —I. In other embodiments, $R^3$ is chloro.

In some embodiments, $R^4$ is hydrogen. In other embodiments, $R^4$ is hydroxyl. In other embodiments, $R^4$ is alkyl or substituted alkyl. In other embodiments, $R^4$ is aryl or substituted aryl. In other embodiments, $R^4$ is heterocycloalkyl or substituted heterocycloalkyl. In other embodiments, $R^4$ is heteroaryl or substituted heteroaryl. In other embodiments, $R^4$ is alkoxyl or substituted alkoxyl. In other embodiments, $R^4$ is acyloxy or substituted acyloxy. In other embodiments, $R^4$ is alkoxylcarbonyl or substituted alkoxycarbonyl. In other embodiments, $R^4$ is acyl or substituted acyl. In other embodiments, $R^4$ is thiol. In other embodiments, $R^4$ is amino or substituted amino. In other embodiments, $R^4$ is aminoacyl or substituted aminoacyl. In other embodiments, $R^4$ is azido. In other embodiments, $R^4$ is carboxyl, substituted carboxyl, carboxyalkyl or substituted carboxyalkyl. In other embodiments, $R^4$ is cyano. In other embodiments, $R^4$ is a halogen, such as —F, —Cl, —Br and —I. In other embodiments, $R^4$ is nitro.

In some embodiments, $R^5$ is hydrogen. In other embodiments, $R^5$ is alkyl or substituted alkyl. In other embodiments, $R^5$ is allyl. In other embodiments, $R^5$ is aryl or substituted aryl. In other embodiments, $R^5$ is heterocycloalkyl or substituted heterocycloalkyl. In other embodiments, $R^5$ is heteroaryl or substituted heteroaryl. In other embodiments, $R^5$ is hydroxyl, alkoxyl or substituted alkoxyl. In other embodiments, $R^5$ is acyloxy or substituted acyloxy. In other embodiments, $R^5$ is alkoxylcarbonyl or substituted alkoxycarbonyl. In other embodiments, $R^5$ is acyl or substituted acyl. In other embodiments, $R^5$ is thiol. In other embodiments, $R^5$ is amino or substituted amino. In other embodiments, $R^5$ is aminoacyl or substituted aminoacyl. In other embodiments, $R^5$ is azido. In other embodiments, $R^5$ is carboxyl, substituted carboxyl, carboxyalkyl or substituted carboxyalkyl. In other embodiments, $R^5$ is cyano. In other embodiments, $R^5$ is a halogen, such as —F, —Cl, —Br and —I. In other embodiments, $R^5$ is nitro.

In certain embodiments, a compound of interest and salts or solvates or stereoisomers thereof, include:

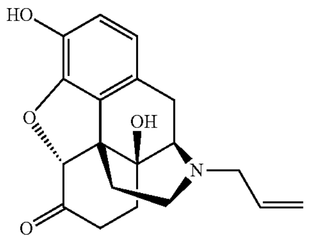

("Naloxone") ((4R,4aS,7aR,12bS)-4a,9-dihydroxy-3-prop-2-enyl-2,4,5,6,7a,13-hexahydro-1H-4,12-methanobenzofuro[3,2-e]isoquinoline-7-one)

Compounds of Formula V

Compositions which find use in the methods of the present disclosure can include compounds of Formula V, shown below, which formula encompasses Cytochalasin and pharmaceutically acceptable salts and derivatives thereof.

In one aspect, the disclosed methods include administration of a compound of Formula V:

(V)

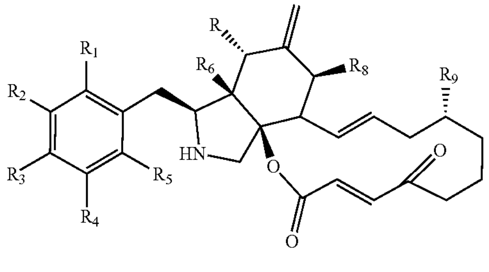

or a pharmaceutically acceptable salt, solvate or prodrug thereof, wherein:

each of $R^1$, $R^2$, $R^3$, $R^4$, $R^5$, $R^6$, $R^7$, $R^8$ and $R^9$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, $—COR^{10}$, $—C(O)OR^{10}$, $—C(O)NR^{10}R^{11}$, $—C{=}NR^{10}$, $—OR^{10}$, $—OC(O)R^{10}$, $—S(O)_t—R^{10}$, $—NR^{10}R^{11}$, $—NR^{10}C(O)R^{11}$, $—N{=}CR^{10}R^{11}$, wherein t is 0, 1, 2 or 3 and $R^{10}$ and $R^{11}$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen.

In some embodiments, $R^1$ is hydrogen. In other embodiments, $R^1$ is alkyl or substituted alkyl. In other embodiments, $R^1$ is aryl or substituted aryl. In other embodiments, $R^1$ is heterocycloalkyl or substituted heterocycloalkyl. In other embodiments, $R^1$ is heteroaryl or substituted heteroaryl. In other embodiments, $R^1$ is hydroxyl, alkoxyl or substituted alkoxyl. In other embodiments, $R^1$ is acyloxy or substituted acyloxy. In other embodiments, $R^1$ is alkoxylcarbonyl or substituted alkoxycarbonyl. In other embodiments, $R^1$ is acyl or substituted acyl. In other embodiments, $R^1$ is thiol. In other embodiments, $R^1$ is amino or substituted amino. In other embodiments, $R^1$ is aminoacyl or substituted aminoacyl. In other embodiments, $R^1$ is azido. In other embodiments, $R^1$ is carboxyl, substituted carboxyl, carboxyalkyl or substituted carboxyalkyl. In other embodiments, $R^1$ is a halogen, such as —F, —Cl, —Br and —I. In other embodiments, $R^1$ is nitro. In certain embodiments, $R^1$ is naphthyl.

In some embodiments, $R^2$ is hydrogen. In other embodiments, $R^2$ is alkyl or substituted alkyl. In other embodiments, $R^2$ is aryl or substituted aryl. In other embodiments, $R^2$ is heterocycloalkyl or substituted heterocycloalkyl. In other embodiments, $R^2$ is heteroaryl or substituted heteroaryl. In other embodiments, $R^2$ is hydroxyl, alkoxyl or substituted alkoxyl. In other embodiments, $R^2$ is acyloxy or substituted acyloxy. In other embodiments, $R^2$ is alkoxylcarbonyl or substituted alkoxycarbonyl. In other embodiments, $R^2$ is acyl or substituted acyl. In other embodiments, $R^2$ is thiol. In other embodiments, $R^2$ is amino or substituted amino. In other embodiments, $R^2$ is aminoacyl or substituted aminoacyl. In other embodiments, $R^2$ is azido. In other embodiments, $R^2$ is carboxyl, substituted carboxyl, carboxyalkyl or substituted carboxyalkyl. In other embodiments, $R^2$ is cyano. In other embodiments, $R^2$ is a halogen, such as —F, —Cl, —Br and —I. In other embodiments, $R^2$ is nitro.

In some embodiments, $R^3$ is alkyl or substituted alkyl, such as methyl, ethyl or propyl. In certain instances, $R^3$ is methyl. In other embodiments, $R^3$ is hydrogen. In other embodiments, $R^3$ is aryl or substituted aryl. In other embodiments, $R^3$ is heterocycloalkyl or substituted heterocycloalkyl. In other embodiments, $R^3$ is heteroaryl or substituted heteroaryl. In other embodiments, $R^3$ is hydroxyl, alkoxyl or substituted alkoxyl. In other embodiments, $R^3$ is acyloxy or substituted acyloxy. In other embodiments, $R^3$ is alkoxylcarbonyl or substituted alkoxycarbonyl. In other embodiments, $R^3$ is acyl or substituted acyl. In other embodiments, $R^3$ is thiol. In other embodiments, $R^3$ is amino or substituted amino. In other embodiments, $R^3$ is aminoacyl or substituted aminoacyl. In other embodiments, $R^3$ is azido. In other embodiments, $R^3$ is carboxyl, substituted carboxyl, carboxyalkyl or substituted carboxyalkyl. In other embodiments, $R^3$ is cyano. In other embodiments, $R^3$ is a halogen, such as —F, —Cl, —Br and —I. In other embodiments, $R^3$ is chloro.

In some embodiments, $R^4$ is hydrogen. In other embodiments, $R^4$ is alkyl or substituted alkyl. In other embodiments, $R^4$ is aryl or substituted aryl. In other embodiments, $R^4$ is heterocycloalkyl or substituted heterocycloalkyl. In other embodiments, $R^4$ is heteroaryl or substituted heteroaryl. In other embodiments, $R^4$ is hydroxyl, alkoxyl or substituted alkoxyl. In other embodiments, $R^4$ is acyloxy or substituted acyloxy. In other embodiments, $R^4$ is alkoxylcarbonyl or substituted alkoxycarbonyl. In other embodiments, $R^4$ is acyl or substituted acyl. In other embodiments, $R^4$ is thiol. In other embodiments, $R^4$ is amino or substituted amino. In other embodiments, $R^4$ is aminoacyl or substituted aminoacyl. In other embodiments, $R^4$ is azido. In other embodiments, $R^4$ is carboxyl, substituted carboxyl, carboxyalkyl or substituted carboxyalkyl. In other embodiments, $R^4$ is cyano. In other embodiments, $R^4$ is a halogen, such as —F, —Cl, —Br and —I. In other embodiments, $R^4$ is nitro.

In some embodiments, $R^5$ is hydrogen. In other embodiments, $R^5$ is alkyl or substituted alkyl. In other embodiments, $R^5$ is aryl or substituted aryl. In other embodiments, $R^5$ is heterocycloalkyl or substituted heterocycloalkyl. In other embodiments, $R^5$ is heteroaryl or substituted heteroaryl. In other embodiments, $R^5$ is hydroxyl, alkoxyl or substituted alkoxyl. In other embodiments, $R^5$ is acyloxy or substituted acyloxy. In other embodiments, $R^5$ is alkoxylcarbonyl or substituted alkoxycarbonyl. In other embodiments, $R^5$ is acyl or substituted acyl. In other embodiments, $R^5$ is thiol. In other embodiments, $R^5$ is amino or substituted amino. In other embodiments, $R^5$ is aminoacyl or substituted aminoacyl. In other embodiments, $R^5$ is azido. In other embodiments, $R^5$ is carboxyl, substituted carboxyl, carboxyalkyl or substituted carboxyalkyl. In other embodiments, $R^5$ is cyano. In other embodiments, $R^5$ is a halogen, such as —F, —Cl, —Br and —I. In other embodiments, $R^5$ is nitro.

In some embodiments, $R^6$ is hydrogen. In other embodiments, $R^6$ is alkoxy, such as methoxy or ethoxy. In other embodiments, $R^6$ is alkyl or substituted alkyl. In other embodiments, $R^6$ is aryl or substituted aryl. In other embodiments, $R^6$ is heterocycloalkyl or substituted heterocycloalkyl. In other embodiments, $R^6$ is heteroaryl or substituted heteroaryl. In other embodiments, $R^6$ is hydroxyl, alkoxyl or substituted alkoxyl. In other embodiments, $R^6$ is acyloxy or substituted acyloxy. In other embodiments, $R^6$ is alkoxylcarbonyl or substituted alkoxycarbonyl. In other embodiments, $R^6$ is acyl or substituted acyl. In other embodiments, $R^6$ is thiol. In other embodiments, $R^6$ is amino or substituted amino. In other embodiments, $R^6$ is aminoacyl or substituted aminoacyl. In other embodiments, $R^6$ is azido. In other embodiments, $R^6$ is carboxyl, substituted carboxyl, carboxyalkyl or substituted carboxyalkyl. In other embodiments, $R^6$ is cyano. In other embodiments, $R^6$ is a halogen, such as —F, —Cl, —Br and —I. In other embodiments, $R^6$ is nitro. In certain embodiments, $R^6$ is alkoxylcarbonyl, such as ethoxycarbonyl.

In some embodiments, $R^7$ is alkyl or substituted alkyl, such as methyl, ethyl or propyl. In certain instances, $R^7$ is methyl. In other embodiments, $R^7$ is hydrogen. In other embodiments, $R^7$ is aryl or substituted aryl. In other embodiments, $R^7$ is heterocycloalkyl or substituted heterocycloalkyl. In other embodiments, $R^7$ is heteroaryl or substituted heteroaryl. In other embodiments, $R^7$ is hydroxyl, alkoxyl or substituted alkoxyl. In other embodiments, $R^7$ is acyloxy or substituted acyloxy. In other embodiments, $R^7$ is alkoxylcarbonyl or substituted alkoxycarbonyl. In other embodiments, $R^7$ is acyl or substituted acyl. In other embodiments, $R^7$ is thiol. In other embodiments, $R^7$ is amino or substituted amino. In other embodiments, $R^7$ is aminoacyl or substituted aminoacyl. In other embodiments, $R^7$ is azido. In other embodiments, $R^7$ is carboxyl, substituted carboxyl, carboxyalkyl or substituted carboxyalkyl. In other embodiments, $R^7$ is cyano. In other embodiments, $R^7$ is a halogen, such as —F, —Cl, —Br and —I. In other embodiments, $R^7$ is nitro. In certain embodiments, $R^7$ is amino.

In some embodiments, $R^8$ is hydrogen. In other embodiments, $R^8$ is alkyl or substituted alkyl. In other embodiments, $R^8$ is aryl or substituted aryl. In other embodiments, $R^8$ is heterocycloalkyl or substituted heterocycloalkyl. In other embodiments, $R^8$ is heteroaryl or substituted heteroaryl. In other embodiments, $R^8$ is hydroxyl, alkoxyl or substituted alkoxyl. In other embodiments, $R^8$ is acyloxy or substituted acyloxy. In other embodiments, $R^8$ is alkoxylcarbonyl or substituted alkoxycarbonyl. In other embodiments, $R^8$ is acyl or substituted acyl. In other embodiments, $R^8$ is thiol. In other embodiments, $R^8$ is amino or substituted amino. In other embodiments, $R^8$ is aminoacyl or substituted aminoacyl. In other embodiments, $R^8$ is azido. In other embodiments, $R^8$ is carboxyl, substituted carboxyl, carboxyalkyl or substituted carboxyalkyl. In other embodiments, $R^8$ is cyano. In other embodiments, $R^8$ is a halogen, such as —F, —Cl, —Br and —I. In other embodiments, $R^8$ is nitro. In certain embodiments, $R^8$ is amino.

In some embodiments, $R^9$ is alkyl or substituted alkyl, such as methyl, ethyl or propyl. In certain instances, $R^9$ is methyl. In other embodiments, $R^9$ is hydrogen. In other embodiments, $R^9$ is aryl or substituted aryl. In other embodiments, $R^9$ is heterocycloalkyl or substituted heterocycloalkyl. In other embodiments, $R^9$ is heteroaryl or substituted heteroaryl. In other embodiments, $R^9$ is hydroxyl, alkoxyl or substituted alkoxyl. In other embodiments, $R^9$ is acyloxy or substituted acyloxy. In other embodiments, $R^9$ is alkoxylcarbonyl or substituted alkoxycarbonyl. In other embodiments, $R^9$ is acyl or substituted acyl. In other embodiments, $R^9$ is thiol. In other embodiments, $R^9$ is amino or substituted amino. In other embodiments, $R^9$ is aminoacyl or substituted aminoacyl. In other embodiments, $R^9$ is azido. In other embodiments, $R^9$ is carboxyl, substituted carboxyl, carboxyalkyl or substituted carboxyalkyl. In other embodiments, $R^9$ is cyano. In other embodiments, $R^9$ is a halogen, such as —F, —Cl, —Br and —I. In other embodiments, $R^9$ is nitro. In certain embodiments, $R^7$ is amino.

In certain embodiments, a compound of interest and salts or solvates or stereoisomers thereof, include:

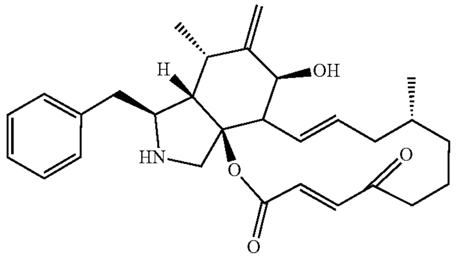 [SMILES: C=C1[C@@H](O)C2/C=C/C[C@H](C)CCCC(=O)/C=C/C(=O)O[C@]23CN[C@@H](Cc2ccccc2)[C@@H]3[C@@H]1C]

("Cytochalasin")

Compounds of Formula VI

Compositions which find use in the methods of the present disclosure can include compounds of Formula VI, shown below, which formula encompasses Putrescine (butane-1,4-diamine) and pharmaceutically acceptable salts and derivatives thereof.

In one aspect, the disclosed methods include administration of a compound of Formula VI:

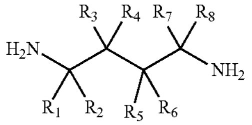

(VI)

or a pharmaceutically acceptable salt, solvate or prodrug thereof, wherein:

each of $R^1$, $R^2$, $R^3$, $R^4$, $R^5$, $R^6$, $R^7$ and $R^8$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, $—COR^9$, $—C(O)OR^9$, $—C(O)NR^9R^{10}$, $—C{=}NR^9$, $—OR^9$, $—OC(O)R^9$, $—S(O)_t—R^9$, $—NR^9R^{10}$, $—NR^9C(O)R^{10}$, $—N{=}CR^9R^{10}$, wherein t is 0, 1, 2 or 3 and $R^9$ and $R^{10}$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen.

In some embodiments, $R^1$ is hydrogen. In other embodiments, $R^1$ is alkyl or substituted alkyl. In other embodiments, $R^1$ is aryl or substituted aryl. In other embodiments, $R^1$ is heterocycloalkyl or substituted heterocycloalkyl. In other embodiments, $R^1$ is heteroaryl or substituted heteroaryl. In other embodiments, $R^1$ is hydroxyl, alkoxyl or substituted alkoxyl. In other embodiments, $R^1$ is acyloxy or substituted acyloxy. In other embodiments, $R^1$ is alkoxylcarbonyl or substituted alkoxycarbonyl. In other embodiments, $R^1$ is acyl or substituted acyl. In other embodiments, $R^1$ is thiol. In other embodiments, $R^1$ is amino or substituted amino. In other embodiments, $R^1$ is aminoacyl or substituted aminoacyl. In other embodiments, $R^1$ is azido. In other embodiments, $R^1$ is carboxyl, substituted carboxyl, carboxyalkyl or substituted carboxyalkyl. In other embodiments, $R^1$ is a halogen, such as —F, —Cl, —Br and —I. In other embodiments, $R^1$ is nitro. In certain embodiments, $R^1$ is naphthyl.

In some embodiments, $R^2$ is hydrogen. In other embodiments, $R^2$ is alkyl or substituted alkyl. In other embodiments, $R^2$ is aryl or substituted aryl. In other embodiments, $R^2$ is heterocycloalkyl or substituted heterocycloalkyl. In other embodiments, $R^2$ is heteroaryl or substituted heteroaryl. In other embodiments, $R^2$ is hydroxyl, alkoxyl or substituted alkoxyl. In other embodiments, $R^2$ is acyloxy or substituted acyloxy. In other embodiments, $R^2$ is alkoxylcarbonyl or substituted alkoxycarbonyl. In other embodiments, $R^2$ is acyl or substituted acyl. In other embodiments, $R^2$ is thiol. In other embodiments, $R^2$ is amino or substituted amino. In other embodiments, $R^2$ is aminoacyl or substituted aminoacyl. In other embodiments, $R^2$ is azido. In other embodiments, $R^2$ is carboxyl, substituted carboxyl, carboxyalkyl or substituted carboxyalkyl. In other embodiments, $R^2$ is cyano. In other embodiments, $R^2$ is a halogen, such as —F, —Cl, —Br and —I. In other embodiments, $R^2$ is nitro.

In some embodiments, $R^3$ is hydrogen. In certain instances, $R^3$ is methyl. In other embodiments, $R^3$ is alkyl or substituted alkyl, such as methyl, ethyl or propyl. In other embodiments, $R^3$ is aryl or substituted aryl. In other embodiments, $R^3$ is heterocycloalkyl or substituted heterocycloalkyl. In other embodiments, $R^3$ is heteroaryl or substituted heteroaryl. In other embodiments, $R^3$ is hydroxyl, alkoxyl or substituted alkoxyl. In other embodiments, $R^3$ is acyloxy or substituted acyloxy. In other embodiments, $R^3$ is alkoxylcarbonyl or substituted alkoxycarbonyl. In other embodiments, $R^3$ is acyl or substituted acyl. In other embodiments, $R^3$ is thiol. In other embodiments, $R^3$ is amino or substituted amino. In other embodiments, $R^3$ is aminoacyl or substituted aminoacyl. In other embodiments, $R^3$ is azido. In other embodiments, $R^3$ is carboxyl, substituted carboxyl, carboxyalkyl or substituted carboxyalkyl. In other embodiments, $R^3$ is cyano. In other embodiments, $R^3$ is a halogen, such as —F, —Cl, —Br and —I. In other embodiments, $R^3$ is chloro.

In some embodiments, $R^4$ is hydrogen. In other embodiments, $R^4$ is alkyl or substituted alkyl. In other embodiments, $R^4$ is aryl or substituted aryl. In other embodiments, $R^4$ is heterocycloalkyl or substituted heterocycloalkyl. In other embodiments, $R^4$ is heteroaryl or substituted heteroaryl. In other embodiments, $R^4$ is hydroxyl, alkoxyl or substituted alkoxyl. In other embodiments, $R^4$ is acyloxy or substituted acyloxy. In other embodiments, $R^4$ is alkoxylcarbonyl or substituted alkoxycarbonyl. In other embodiments, $R^4$ is acyl or substituted acyl. In other embodiments, $R^4$ is thiol. In other embodiments, $R^4$ is amino or substituted amino. In other embodiments, $R^4$ is aminoacyl or substituted aminoacyl. In other embodiments, $R^4$ is azido. In other embodiments, $R^4$ is carboxyl, substituted carboxyl, carboxyalkyl or substituted carboxyalkyl. In other embodiments, $R^4$ is cyano. In other embodiments, $R^4$ is a halogen, such as —F, —Cl, —Br and —I. In other embodiments, $R^4$ is nitro.

In some embodiments, $R^5$ is hydrogen. In other embodiments, $R^5$ is alkyl or substituted alkyl. In other embodiments, $R^5$ is aryl or substituted aryl. In other embodiments, $R^5$ is heterocycloalkyl or substituted heterocycloalkyl. In other embodiments, $R^5$ is heteroaryl or substituted heteroaryl. In other embodiments, $R^5$ is hydroxyl, alkoxyl or substituted alkoxyl. In other embodiments, $R^5$ is acyloxy or substituted acyloxy. In other embodiments, $R^5$ is alkoxylcarbonyl or substituted alkoxycarbonyl. In other embodiments, $R^5$ is acyl or substituted acyl. In other embodiments, $R^5$ is thiol. In other embodiments, $R^5$ is amino or substituted amino. In other embodiments, $R^5$ is aminoacyl or substituted aminoacyl. In other embodiments, $R^5$ is azido. In other embodiments, $R^5$ is carboxyl, substituted carboxyl, carboxyalkyl or substituted carboxyalkyl. In other embodiments, $R^5$ is cyano. In other embodiments, $R^5$ is a halogen, such as —F, —Cl, —Br and —I. In other embodiments, $R^5$ is nitro.

In some embodiments, $R^6$ is hydrogen. In other embodiments, $R^6$ is alkoxy, such as methoxy or ethoxy. In other embodiments, $R^6$ is alkyl or substituted alkyl. In other embodiments, $R^6$ is aryl or substituted aryl. In other embodiments, $R^6$ is heterocycloalkyl or substituted heterocycloalkyl. In other embodiments, $R^6$ is heteroaryl or substituted heteroaryl. In other embodiments, $R^6$ is hydroxyl, alkoxyl or substituted alkoxyl. In other embodiments, $R^6$ is acyloxy or substituted acyloxy. In other embodiments, $R^6$ is alkoxylcarbonyl or substituted alkoxycarbonyl. In other embodiments, $R^6$ is acyl or substituted acyl. In other embodiments, $R^6$ is thiol. In other embodiments, $R^6$ is amino or substituted amino. In other embodiments, $R^6$ is aminoacyl or substituted aminoacyl. In other embodiments, $R^6$ is azido. In other embodiments, $R^6$ is carboxyl, substituted carboxyl, carboxyalkyl or substituted carboxyalkyl. In other embodiments, $R^6$ is cyano. In other embodiments, $R^6$ is a halogen, such as —F, —Cl, —Br and —I. In other embodiments, $R^6$ is nitro. In certain embodiments, $R^6$ is alkoxylcarbonyl, such as ethoxycarbonyl.

In some embodiments, $R^7$ is hydrogen. In other embodiments, $R^7$ is alkyl or substituted alkyl, such as methyl, ethyl or propyl. In certain instances, $R^7$ is methyl. In other embodiments, $R^7$ is aryl or substituted aryl. In other embodiments, $R^7$ is heterocycloalkyl or substituted heterocycloalkyl. In other embodiments, $R^7$ is heteroaryl or substituted heteroaryl. In other embodiments, $R^7$ is hydroxyl, alkoxyl or substituted alkoxyl. In other embodiments, $R^7$ is acyloxy or substituted acyloxy. In other embodiments, $R^7$ is alkoxylcarbonyl or substituted alkoxycarbonyl. In other embodiments, $R^7$ is acyl or substituted acyl. In other embodiments, $R^7$ is thiol. In other embodiments, $R^7$ is amino or substituted amino. In other embodiments, $R^7$ is aminoacyl or substituted aminoacyl. In other embodiments, $R^7$ is azido. In other embodiments, $R^7$ is carboxyl, substituted carboxyl, carboxyalkyl or substituted carboxyalkyl. In other embodiments, $R^7$ is cyano. In other embodiments, $R^7$ is a halogen, such as —F, —Cl, —Br and —I. In other embodiments, $R^7$ is nitro. In certain embodiments, $R^7$ is amino.

In some embodiments, $R^8$ is hydrogen. In other embodiments, $R^8$ is alkyl or substituted alkyl. In other embodiments, $R^8$ is aryl or substituted aryl. In other embodiments, $R^8$ is heterocycloalkyl or substituted heterocycloalkyl. In other embodiments, $R^8$ is heteroaryl or substituted heteroaryl. In other embodiments, $R^8$ is hydroxyl, alkoxyl or substituted alkoxyl. In other embodiments, $R^8$ is acyloxy or substituted acyloxy. In other embodiments, $R^8$ is alkoxylcarbonyl or substituted alkoxycarbonyl. In other embodiments, $R^8$ is acyl or substituted acyl. In other embodiments, $R^8$ is thiol. In other embodiments, $R^8$ is amino or substituted amino. In other embodiments, $R^8$ is aminoacyl or substituted aminoacyl. In other embodiments, $R^8$ is azido. In other embodiments, $R^8$ is carboxyl, substituted carboxyl, carboxyalkyl or substituted carboxyalkyl. In other embodiments, $R^8$ is cyano. In other embodiments, $R^8$ is a halogen, such as —F, —Cl, —Br and —I. In other embodiments, $R^8$ is nitro. In certain embodiments, $R^8$ is amino.

In certain embodiments, a compound of interest and salts or solvates or stereoisomers thereof, include:

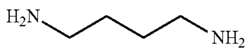

("Putrescine") ("Butane-1,4-diamine")

Compounds of Formula VII

Compositions which find use in the methods of the present disclosure can include compounds of Formula VII, shown below, which formula encompasses CB-1954 (5-(1-aziridinyl)-2,4-dinitrobenzamide) and pharmaceutically acceptable salts and derivatives thereof.

In one aspect, the disclosed methods include administration of a compound of Formula VII:

(VII)

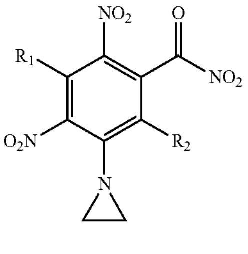

or a pharmaceutically acceptable salt, solvate or prodrug thereof, wherein:

each of $R^1$, $R^2$ and $R^3$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, $—COR^4$, $—C(O)OR^4$, $—C(O)NR^4R^5$, $—C{=}NR^4$, $—OR^4$, $—OC(O)R^4$, $—S(O)_t—R^4$, $—NR^4R^5$, $—NR^4C(O)R^5$, $—N{=}CR^4R^5$, wherein t is 0, 1, 2 or 3 and $R^4$ and $R^5$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen.

In some embodiments, $R^1$ is hydrogen. In other embodiments, $R^1$ is alkyl or substituted alkyl. In other embodiments, $R^1$ is aryl or substituted aryl. In other embodiments, $R^1$ is heterocycloalkyl or substituted heterocycloalkyl. In other embodiments, $R^1$ is heteroaryl or substituted heteroaryl. In other embodiments, $R^1$ is hydroxyl, alkoxyl or substituted alkoxyl. In other embodiments, $R^1$ is acyloxy or substituted acyloxy. In other embodiments, $R^1$ is alkoxylcarbonyl or substituted alkoxycarbonyl. In other embodiments, $R^1$ is acyl or substituted acyl. In other embodiments, $R^1$ is thiol. In other embodiments, $R^1$ is amino or substituted amino. In other embodiments, $R^1$ is aminoacyl or substituted aminoacyl. In other embodiments, $R^1$ is azido. In other embodiments, $R^1$ is carboxyl, substituted carboxyl, carboxyalkyl or substituted carboxyalkyl. In other embodiments, $R^1$ is a halogen, such as —F, —Cl, —Br and —I. In other embodiments, $R^1$ is nitro. In certain embodiments, $R^1$ is naphthyl.

In some embodiments, $R^2$ is hydrogen. In other embodiments, $R^2$ is alkyl or substituted alkyl. In other embodiments, $R^2$ is aryl or substituted aryl. In other embodiments, $R^2$ is heterocycloalkyl or substituted heterocycloalkyl. In other embodiments, $R^2$ is heteroaryl or substituted heteroaryl. In other embodiments, $R^2$ is hydroxyl, alkoxyl or substituted alkoxyl. In other embodiments, $R^2$ is acyloxy or substituted acyloxy. In other embodiments, $R^2$ is alkoxylcarbonyl or substituted alkoxycarbonyl. In other embodiments, $R^2$ is acyl or substituted acyl. In other embodiments, $R^2$ is thiol. In other embodiments, $R^2$ is amino or substituted amino. In other embodiments, $R^2$ is aminoacyl or substituted aminoacyl. In other embodiments, $R^2$ is azido. In other embodiments, $R^2$ is carboxyl, substituted carboxyl, carboxyalkyl or substituted carboxyalkyl. In other embodiments, $R^2$ is cyano. In other embodiments, $R^2$ is a halogen, such as —F, —Cl, —Br and —I. In other embodiments, $R^2$ is nitro.

In some embodiments, $R^3$ is hydrogen. In certain instances, $R^3$ is methyl. In other embodiments, $R^3$ is alkyl or substituted alkyl, such as methyl, ethyl or propyl. In other embodiments, $R^3$ is aryl or substituted aryl. In other embodiments, $R^3$ is heterocycloalkyl or substituted heterocycloalkyl. In other embodiments, $R^3$ is heteroaryl or substituted heteroaryl. In other embodiments, $R^3$ is hydroxyl, alkoxyl or substituted alkoxyl. In other embodiments, $R^3$ is acyloxy or substituted acyloxy. In other embodiments, $R^3$ is alkoxylcarbonyl or substituted alkoxycarbonyl. In other embodiments, $R^3$ is acyl or substituted acyl. In other embodiments, $R^3$ is thiol. In other embodiments, $R^3$ is amino or substituted amino. In other embodiments, $R^3$ is aminoacyl or substituted aminoacyl. In other embodiments, $R^3$ is azido. In other embodiments, $R^3$ is carboxyl, substituted carboxyl, carboxyalkyl or substituted carboxyalkyl. In other embodiments, $R^3$ is cyano. In other embodiments, $R^3$ is a halogen, such as —F, —Cl, —Br and —I. In other embodiments, $R^3$ is chloro.

In certain embodiments, a compound of interest and salts or solvates or stereoisomers thereof, include:

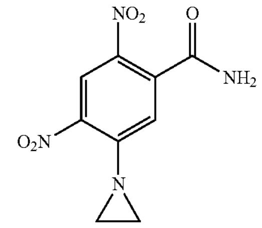 [SMILES: NC(=O)c1cc(N2CC2)c([N+](=O)[O-])cc1[N+](=O)[O-]]

("CB-1954") (5-(1-aziridinyl)-2,4-dinitrobenzamide)

Compounds of Formula VIII

Compositions which find use in the methods of the present disclosure can include compounds of Formula VIII, shown below, which formula encompasses biperiden ((1RS, 2SR,4RS)-1-(bicyclo[2.2.1]hept-5-en-2-yl)-1-phenyl-3-(piperidin-1-yl)propan-1-01) and pharmaceutically acceptable salts and derivatives thereof. Pharmaceutical compositions and methods of the present disclosure also contemplate compounds of Formula VIII.

In one aspect, the disclosed methods include administration of a compound of Formula VIIII:

(VIII)

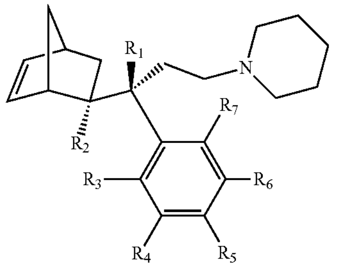

or a pharmaceutically acceptable salt, solvate or prodrug thereof, wherein:

each of $R^1$, $R^2$, $R^3$, $R^4$, $R^5$, $R^6$ and $R^7$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, $—COR^8$, $—C(O)OR^8$, $—C(O)NR^8R^9$, $—C{=}NR^8$, $—OR^9$, $—OC(O)R^8$, $—S(O)_t—R^8$, $—NR^8R^9$, $—NR^8C(O)R^9$, $—N{=}CR^8R^9$, wherein t is 0, 1, 2 or 3 and $R^8$ and $R^9$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen.

In some embodiments, $R^1$ is hydroxyl. In other embodiments, $R^1$ is hydrogen. In other embodiments, $R^1$ is alkyl or substituted alkyl. In other embodiments, $R^1$ is aryl or substituted aryl. In other embodiments, $R^1$ is heterocycloalkyl or substituted heterocycloalkyl. In other embodiments, $R^1$ is heteroaryl or substituted heteroaryl. In other embodiments, $R^1$ is alkoxyl or substituted alkoxyl. In other embodiments, $R^1$ is acyloxy or substituted acyloxy. In other embodiments, $R^1$ is alkoxylcarbonyl or substituted alkoxycarbonyl. In other embodiments, $R^1$ is acyl or substituted acyl. In other embodiments, $R^1$ is thiol. In other embodiments, $R^1$ is amino or substituted amino. In other embodiments, $R^1$ is aminoacyl or substituted aminoacyl. In other embodiments, $R^1$ is azido. In other embodiments, $R^1$ is carboxyl, substituted carboxyl, carboxyalkyl or substituted carboxyalkyl. In other embodiments, $R^1$ is a halogen, such as —F, —Cl, —Br and —I. In other embodiments, $R^1$ is nitro. In certain embodiments, $R^1$ is naphthyl.

In some embodiments, $R^2$ is hydrogen. In other embodiments, $R^2$ is alkyl or substituted alkyl. In other embodiments, $R^2$ is aryl or substituted aryl. In other embodiments, $R^2$ is heterocycloalkyl or substituted heterocycloalkyl. In other embodiments, $R^2$ is heteroaryl or substituted heteroaryl. In other embodiments, $R^2$ is hydroxyl, alkoxyl or substituted alkoxyl. In other embodiments, $R^2$ is acyloxy or substituted acyloxy. In other embodiments, $R^2$ is alkoxylcarbonyl or substituted alkoxycarbonyl. In other embodiments, $R^2$ is acyl or substituted acyl. In other embodiments, $R^2$ is thiol. In other embodiments, $R^2$ is amino or substituted amino. In other embodiments, $R^2$ is aminoacyl or substituted aminoacyl. In other embodiments, $R^2$ is azido. In other embodiments, $R^2$ is carboxyl, substituted carboxyl, carboxyalkyl or substituted carboxyalkyl. In other embodiments, $R^2$ is cyano. In other embodiments, $R^2$ is a halogen, such as —F, —Cl, —Br and —I. In other embodiments, $R^2$ is nitro.

In some embodiments, $R^3$ is hydrogen. In certain instances, $R^3$ is methyl. In other embodiments, $R^3$ is alkyl or substituted alkyl, such as methyl, ethyl or propyl. In other embodiments, $R^3$ is aryl or substituted aryl. In other embodiments, $R^3$ is heterocycloalkyl or substituted heterocycloalkyl. In other embodiments, $R^3$ is heteroaryl or substituted heteroaryl. In other embodiments, $R^3$ is hydroxyl, alkoxyl or substituted alkoxyl. In other embodiments, $R^3$ is acyloxy or substituted acyloxy. In other embodiments, $R^3$ is alkoxylcarbonyl or substituted alkoxycarbonyl. In other embodiments, $R^3$ is acyl or substituted acyl. In other embodiments, $R^3$ is thiol. In other embodiments, $R^3$ is amino or substituted amino. In other embodiments, $R^3$ is aminoacyl or substituted aminoacyl. In other embodiments, $R^3$ is azido. In other embodiments, $R^3$ is carboxyl, substituted carboxyl, carboxyalkyl or substituted carboxyalkyl. In other embodiments, $R^3$ is cyano. In other embodiments, $R^3$ is a halogen, such as —F, —Cl, —Br and —I. In other embodiments, $R^3$ is chloro.

In some embodiments, $R^4$ is hydrogen. In other embodiments, $R^4$ is alkyl or substituted alkyl. In other embodiments, $R^4$ is aryl or substituted aryl. In other embodiments, $R^4$ is heterocycloalkyl or substituted heterocycloalkyl. In other embodiments, $R^4$ is heteroaryl or substituted heteroaryl. In other embodiments, $R^4$ is hydroxyl, alkoxyl or substituted alkoxyl. In other embodiments, $R^4$ is acyloxy or substituted acyloxy. In other embodiments, $R^4$ is alkoxylcarbonyl or substituted alkoxycarbonyl. In other embodiments, $R^4$ is acyl or substituted acyl. In other embodiments, $R^4$ is thiol. In other embodiments, $R^4$ is amino or substituted amino. In other embodiments, $R^4$ is aminoacyl or substituted aminoacyl. In other embodiments, $R^4$ is azido. In other embodiments, $R^4$ is carboxyl, substituted carboxyl, carboxyalkyl or substituted carboxyalkyl. In other embodiments, $R^4$ is cyano. In other embodiments, $R^4$ is a halogen, such as —F, —Cl, —Br and —I. In other embodiments, $R^4$ is nitro.

In some embodiments, $R^5$ is hydrogen. In other embodiments, $R^5$ is alkyl or substituted alkyl. In other embodiments, $R^5$ is aryl or substituted aryl. In other embodiments, $R^5$ is heterocycloalkyl or substituted heterocycloalkyl. In other embodiments, $R^5$ is heteroaryl or substituted heteroaryl. In other embodiments, $R^5$ is hydroxyl, alkoxyl or substituted alkoxyl. In other embodiments, $R^5$ is acyloxy or substituted acyloxy. In other embodiments, $R^5$ is alkoxylcarbonyl or substituted alkoxycarbonyl. In other embodiments, $R^5$ is acyl or substituted acyl. In other embodiments, $R^5$ is thiol. In other embodiments, $R^5$ is amino or substituted amino. In other embodiments, $R^5$ is aminoacyl or substituted aminoacyl. In other embodiments, $R^5$ is azido. In other embodiments, $R^5$ is carboxyl, substituted carboxyl, carboxyalkyl or substituted carboxyalkyl. In other embodiments, $R^5$ is cyano. In other embodiments, $R^5$ is a halogen, such as —F, —Cl, —Br and —I. In other embodiments, $R^5$ is nitro.

In some embodiments, $R^6$ is hydrogen. In other embodiments, $R^6$ is alkoxy, such as methoxy or ethoxy. In other embodiments, $R^6$ is alkyl or substituted alkyl. In other embodiments, $R^6$ is aryl or substituted aryl. In other embodiments, $R^6$ is heterocycloalkyl or substituted heterocycloalkyl. In other embodiments, $R^6$ is heteroaryl or substituted heteroaryl. In other embodiments, $R^6$ is hydroxyl, alkoxyl or substituted alkoxyl. In other embodiments, $R^6$ is acyloxy or substituted acyloxy. In other embodiments, $R^6$ is alkoxylcarbonyl or substituted alkoxycarbonyl. In other embodiments, $R^6$ is acyl or substituted acyl. In other embodiments, $R^6$ is thiol. In other embodiments, $R^6$ is amino or substituted amino. In other embodiments, $R^6$ is aminoacyl or substituted aminoacyl. In other embodiments, $R^6$ is azido. In other embodiments, $R^6$ is carboxyl, substituted carboxyl, carboxyalkyl or substituted carboxyalkyl. In other embodiments, $R^6$ is cyano. In other embodiments, $R^6$ is a halogen, such as —F, —Cl, —Br and —I. In other embodiments, $R^6$ is nitro. In certain embodiments, $R^6$ is alkoxylcarbonyl, such as ethoxycarbonyl.

In some embodiments, $R^7$ is hydrogen. In other embodiments, $R^7$ is alkyl or substituted alkyl, such as methyl, ethyl or propyl. In certain instances, $R^7$ is methyl. In other embodiments, $R^7$ is aryl or substituted aryl. In other embodiments, $R^7$ is heterocycloalkyl or substituted heterocycloalkyl. In other embodiments, $R^7$ is heteroaryl or substituted heteroaryl. In other embodiments, $R^7$ is hydroxyl, alkoxyl or substituted alkoxyl. In other embodiments, $R^7$ is acyloxy or substituted acyloxy. In other embodiments, $R^7$ is alkoxylcarbonyl or substituted alkoxycarbonyl. In other embodiments, $R^7$ is acyl or substituted acyl. In other embodiments, $R^7$ is thiol. In other embodiments, $R^7$ is amino or substituted amino. In other embodiments, $R^7$ is aminoacyl or substituted aminoacyl. In other embodiments, $R^7$ is azido. In other embodiments, $R^7$ is carboxyl, substituted carboxyl, carboxyalkyl or substituted carboxyalkyl. In other embodiments, $R^7$ is cyano. In other embodiments, $R^7$ is a halogen, such as —F, —Cl, —Br and —I. In other embodiments, $R^7$ is nitro. In certain embodiments, $R^7$ is amino.

In certain embodiments, a compound of interest and salts or solvates or stereoisomers thereof, include:

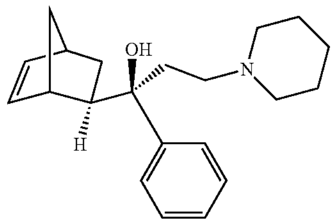 [SMILES: O[C@@](CCN1CCCCC1)(c1ccccc1)[C@@H]1CC2C=CC1C2]

("biperiden") ((1RS,2SR,4RS)-1-(bicyclo[2.2.1]hept-5-en-2-yl)-1-phenyl-3-(piperidin-1-yl)propan-1-ol))

Compounds of Formula IX

Compositions which find use in the methods of the present disclosure can include compounds of Formula IX, shown below, which formula encompasses RO-4929097 (2,2-dimethyl-N-[(10S)-9-oxo-8-azatricyclo[9.4.0.02,7] pentadeca-1,2,4,6,11,13-hexaene-10-yl]-N'-(2,2,3,3,3-pentafluoropropyl)propanediamide) and pharmaceutically acceptable salts and derivatives thereof.

In one aspect, the disclosed methods include administration of a compound of Formula IX:

(IX)

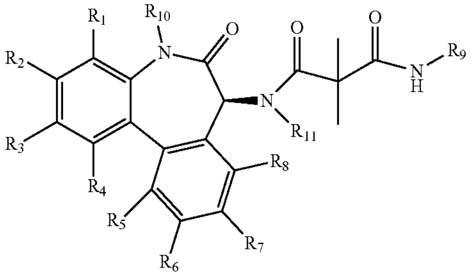

or a pharmaceutically acceptable salt, solvate or prodrug thereof, wherein:

each of $R^1$, $R^2$, $R^3$, $R^4$, $R^5$, $R^6$, $R^7$, $R^8$, $R^9$, $R^{10}$ and $R^{11}$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, $—COR^{12}$, $—C(O)OR^{12}$, $—C(O)NR^{12}R^{13}$, $—C{=}NR^{12}$, $—OR^{12}$, $—OC(O)R^{12}$, $—S(O)_t—R^{12}$, $—NR^{12}R^{13}$, $—NR^{12}C(O)R^{13}$, $—N{=}CR^{12}R^{13}$, wherein t is 0, 1, 2 or 3 and $R^{12}$ and $R^{13}$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen.

In some embodiments, $R^1$ is hydrogen. In other embodiments, $R^1$ is alkyl or substituted alkyl. In other embodiments, $R^1$ is aryl or substituted aryl. In other embodiments, $R^1$ is heterocycloalkyl or substituted heterocycloalkyl. In other embodiments, $R^1$ is heteroaryl or substituted heteroaryl. In other embodiments, $R^1$ is hyrdoxyl alkoxyl or substituted alkoxyl. In other embodiments, $R^1$ is acyloxy or substituted acyloxy. In other embodiments, $R^1$ is alkoxylcarbonyl or substituted alkoxycarbonyl. In other embodiments, $R^1$ is acyl or substituted acyl. In other embodiments, $R^1$ is thiol. In other embodiments, $R^1$ is amino or substituted amino. In other embodiments, $R^1$ is aminoacyl or substituted aminoacyl. In other embodiments, $R^1$ is azido. In other embodiments, $R^1$ is carboxyl, substituted carboxyl, carboxyalkyl or substituted carboxyalkyl. In other embodiments, $R^1$ is a halogen, such as —F, —Cl, —Br and —I. In other embodiments, $R^1$ is nitro. In certain embodiments, $R^1$ is naphthyl.

In some embodiments, $R^2$ is hydrogen. In other embodiments, $R^2$ is alkyl or substituted alkyl. In other embodiments, $R^2$ is aryl or substituted aryl. In other embodiments, $R^2$ is heterocycloalkyl or substituted heterocycloalkyl. In other embodiments, $R^2$ is heteroaryl or substituted heteroaryl. In other embodiments, $R^2$ is hydroxyl, alkoxyl or substituted alkoxyl. In other embodiments, $R^2$ is acyloxy or substituted acyloxy. In other embodiments, $R^2$ is alkoxylcarbonyl or substituted alkoxycarbonyl. In other embodiments, $R^2$ is acyl or substituted acyl. In other embodiments, $R^2$ is thiol. In other embodiments, $R^2$ is amino or substituted amino. In other embodiments, $R^2$ is aminoacyl or substituted aminoacyl. In other embodiments, $R^2$ is azido. In other embodiments, $R^2$ is carboxyl, substituted carboxyl, carboxyalkyl or substituted carboxyalkyl. In other embodiments, $R^2$ is cyano. In other embodiments, $R^2$ is a halogen, such as —F, —Cl, —Br and —I. In other embodiments, $R^2$ is nitro.

In some embodiments, $R^3$ is hydrogen. In certain instances, $R^3$ is methyl. In other embodiments, $R^3$ is alkyl or substituted alkyl, such as methyl, ethyl or propyl. In other embodiments, $R^3$ is aryl or substituted aryl. In other embodiments, $R^3$ is heterocycloalkyl or substituted heterocycloalkyl. In other embodiments, $R^3$ is heteroaryl or substituted heteroaryl. In other embodiments, $R^3$ is hydroxyl, alkoxyl or substituted alkoxyl. In other embodiments, $R^3$ is acyloxy or substituted acyloxy. In other embodiments, $R^3$ is alkoxylcarbonyl or substituted alkoxycarbonyl. In other embodiments, $R^3$ is acyl or substituted acyl. In other embodiments, $R^3$ is thiol. In other embodiments, $R^3$ is amino or substituted amino. In other embodiments, $R^3$ is aminoacyl or substituted aminoacyl. In other embodiments, $R^3$ is azido. In other embodiments, $R^3$ is carboxyl, substituted carboxyl, carboxyalkyl or substituted carboxyalkyl. In other embodiments, $R^3$ is cyano. In other embodiments, $R^3$ is a halogen, such as —F, —Cl, —Br and —I. In other embodiments, $R^3$ is chloro.

In some embodiments, $R^4$ is hydrogen. In other embodiments, $R^4$ is alkyl or substituted alkyl. In other embodiments, $R^4$ is aryl or substituted aryl. In other embodiments, $R^4$ is heterocycloalkyl or substituted heterocycloalkyl. In other embodiments, $R^4$ is heteroaryl or substituted heteroaryl. In other embodiments, $R^4$ is hydroxyl, alkoxyl or substituted alkoxyl. In other embodiments, $R^4$ is acyloxy or substituted acyloxy. In other embodiments, $R^4$ is alkoxylcarbonyl or substituted alkoxycarbonyl. In other embodiments, $R^4$ is acyl or substituted acyl. In other embodiments, $R^4$ is thiol. In other embodiments, $R^4$ is amino or substituted amino. In other embodiments, $R^4$ is aminoacyl or substituted aminoacyl. In other embodiments, $R^4$ is azido. In other embodiments, $R^4$ is carboxyl, substituted carboxyl, carboxyalkyl or substituted carboxyalkyl. In other embodiments, $R^4$ is cyano. In other embodiments, $R^4$ is a halogen, such as —F, —Cl, —Br and —I. In other embodiments, $R^4$ is nitro.

In some embodiments, $R^5$ is hydrogen. In other embodiments, $R^5$ is alkyl or substituted alkyl. In other embodiments, $R^5$ is aryl or substituted aryl. In other embodiments, $R^5$ is heterocycloalkyl or substituted heterocycloalkyl. In other embodiments, $R^5$ is heteroaryl or substituted heteroaryl. In other embodiments, $R^5$ is hydroxyl, alkoxyl or substituted alkoxyl. In other embodiments, $R^5$ is acyloxy or substituted acyloxy. In other embodiments, $R^5$ is alkoxylcarbonyl or substituted alkoxycarbonyl. In other embodiments, $R^5$ is acyl or substituted acyl. In other embodiments, $R^5$ is thiol. In other embodiments, $R^5$ is amino or substituted amino. In other embodiments, $R^5$ is aminoacyl or substituted aminoacyl. In other embodiments, $R^5$ is azido. In other embodiments, $R^5$ is carboxyl, substituted carboxyl, carboxyalkyl or substituted carboxyalkyl. In other embodiments, $R^5$ is cyano. In other embodiments, $R^5$ is a halogen, such as —F, —Cl, —Br and —I. In other embodiments, $R^5$ is nitro.

In some embodiments, $R^6$ is hydrogen. In other embodiments, $R^6$ is alkoxy, such as methoxy or ethoxy. In other embodiments, $R^6$ is alkyl or substituted alkyl. In other embodiments, $R^6$ is aryl or substituted aryl. In other embodiments, $R^6$ is heterocycloalkyl or substituted heterocycloalkyl. In other embodiments, $R^6$ is heteroaryl or substituted heteroaryl. In other embodiments, $R^6$ is hydroxyl, alkoxyl or substituted alkoxyl. In other embodiments, $R^6$ is acyloxy or substituted acyloxy. In other embodiments, $R^6$ is alkoxylcarbonyl or substituted alkoxycarbonyl. In other embodiments, $R^6$ is acyl or substituted acyl. In other embodiments, $R^6$ is thiol. In other embodiments, $R^6$ is amino or substituted amino. In other embodiments, $R^6$ is aminoacyl or substituted aminoacyl. In other embodiments, $R^6$ is azido. In other embodiments, $R^6$ is carboxyl, substituted carboxyl, carboxyalkyl or substituted carboxyalkyl. In other embodiments, $R^6$ is cyano. In other embodiments, $R^6$ is a halogen, such as —F, —Cl, —Br and —I. In other embodiments, $R^6$ is nitro. In certain embodiments, $R^6$ is alkoxylcarbonyl, such as ethoxycarbonyl.

In some embodiments, $R^7$ is hydrogen. In other embodiments, $R^7$ is alkyl or substituted alkyl, such as methyl, ethyl or propyl. In certain instances, $R^7$ is methyl. In other embodiments, $R^7$ is aryl or substituted aryl. In other embodiments, $R^7$ is heterocycloalkyl or substituted heterocycloalkyl. In other embodiments, $R^7$ is heteroaryl or substituted heteroaryl. In other embodiments, $R^7$ is hydroxyl, alkoxyl or substituted alkoxyl. In other embodiments, $R^7$ is acyloxy or substituted acyloxy. In other embodiments, $R^7$ is alkoxylcarbonyl or substituted alkoxycarbonyl. In other embodiments, $R^7$ is acyl or substituted acyl. In other embodiments, $R^7$ is thiol. In other embodiments, $R^7$ is amino or substituted amino. In other embodiments, $R^7$ is aminoacyl or substituted aminoacyl. In other embodiments, $R^7$ is azido. In other embodiments, $R^7$ is carboxyl, substituted carboxyl, carboxyalkyl or substituted carboxyalkyl. In other embodiments, $R^7$ is cyano. In other embodiments, $R^7$ is a halogen, such as —F, —Cl, —Br and —I. In other embodiments, $R^7$ is nitro. In certain embodiments, $R^7$ is amino.

In some embodiments, $R^9$ is alkyl or substituted alkyl, such as methyl, ethyl or propyl. In certain instances, $R^9$ is pentalfuoro ethyl. In other embodiments, $R^9$ is hydrogen. In other embodiments, $R^9$ is aryl or substituted aryl. In other embodiments, $R^9$ is heterocycloalkyl or substituted heterocycloalkyl. In other embodiments, $R^9$ is heteroaryl or substituted heteroaryl. In other embodiments, $R^9$ is hydroxyl, alkoxyl or substituted alkoxyl. In other embodiments, $R^9$ is acyloxy or substituted acyloxy. In other embodiments, $R^9$ is alkoxylcarbonyl or substituted alkoxycarbonyl. In other embodiments, $R^9$ is acyl or substituted acyl. In other embodiments, $R^9$ is thiol. In other embodiments, $R^9$ is amino or substituted amino. In other embodiments, $R^9$ is aminoacyl or substituted aminoacyl. In other embodiments, $R^9$ is azido. In other embodiments, $R^9$ is carboxyl, substituted carboxyl, carboxyalkyl or substituted carboxyalkyl. In other embodiments, $R^9$ is cyano. In other embodiments, $R^9$ is a halogen, such as —F, —Cl, —Br and —I. In other embodiments, $R^9$ is nitro. In certain embodiments, $R^7$ is amino.

In some embodiments, $R^{10}$ is hydrogen. In other embodiments, $R^{10}$ is alkyl or substituted alkyl. In other embodiments, $R^{10}$ is aryl or substituted aryl. In other embodiments, $R^{10}$ is heterocycloalkyl or substituted heterocycloalkyl. In other embodiments, $R^{10}$ is heteroaryl or substituted heteroaryl. In other embodiments, $R^{10}$ is hydroxyl, alkoxyl or substituted alkoxyl. In other embodiments, $R^{10}$ is acyloxy or substituted acyloxy. In other embodiments, $R^{10}$ is alkoxylcarbonyl or substituted alkoxycarbonyl. In other embodiments, $R^{10}$ is acyl or substituted acyl. In other embodiments, $R^{10}$ is thiol. In other embodiments, $R^{10}$ is amino or substituted amino. In other embodiments, $R^{10}$ is aminoacyl or substituted aminoacyl. In other embodiments, $R^{10}$ is azido. In other embodiments, $R^{10}$ is carboxyl, substituted carboxyl, carboxyalkyl or substituted carboxyalkyl. In other embodiments, $R^{10}$ is cyano. In other embodiments, $R^{10}$ is a halogen, such as —F, —Cl, —Br and —I. In other embodiments, $R^{10}$ is nitro. In certain embodiments, $R^{10}$ is amino.

In some embodiments, $R^{11}$ is hydrogen. In other embodiments, $R^{11}$ is alkyl or substituted alkyl. In other embodiments, $R^{11}$ is aryl or substituted aryl. In other embodiments, $R^{11}$ is heterocycloalkyl or substituted heterocycloalkyl. In other embodiments, $R^{11}$ is heteroaryl or substituted heteroaryl. In other embodiments, $R^{11}$ is hydroxyl, alkoxyl or substituted alkoxyl. In other embodiments, $R^{11}$ is acyloxy or substituted acyloxy. In other embodiments, $R^{11}$ is alkoxylcarbonyl or substituted alkoxycarbonyl. In other embodiments, $R^{11}$ is acyl or substituted acyl. In other embodiments, $R^{11}$ is thiol. In other embodiments, $R^{11}$ is amino or substituted amino. In other embodiments, $R^{11}$ is aminoacyl or substituted aminoacyl. In other embodiments, $R^{11}$ is azido. In other embodiments, $R^{11}$ is carboxyl, substituted carboxyl, carboxyalkyl or substituted carboxyalkyl. In other embodiments, $R^{11}$ is cyano. In other embodiments, $R^{11}$ is a halogen, such as —F, —Cl, —Br and —I. In other embodiments, $R^{11}$ is nitro. In certain embodiments, $R^{11}$ is amino.

In certain embodiments, a compound of interest and salts or solvates or stereoisomers thereof, include:

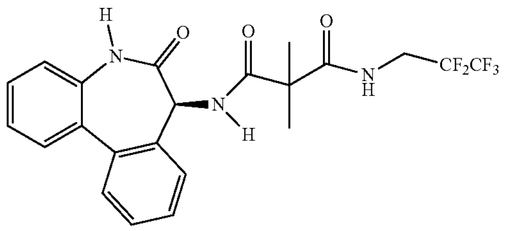

("RO-4929097") ((2,2-dimethyl-N-[(10S)-9-oxo-8-azatricyclo[9.4.0.02,7]pentadeca-1,2,4,6,11,13-hexaene-10-yl]-N'-(2,2,3,3,3-pentafluoropropyl)propanediamide)

Compounds of Formula X

Compositions which find use in the methods of the present disclosure can include compounds of Formula X, shown below, which formula encompasses Fmoc-leucine and pharmaceutically acceptable salts and derivatives thereof.

In one aspect, the disclosed methods include administration of a compound of Formula X:

(X)

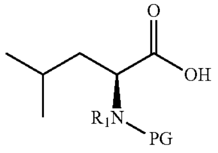

or a pharmaceutically acceptable salt, solvate or prodrug thereof, wherein $R^1$ is selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, $—COR^2$, $—C(O)OR^2$, $—C(O)NR^2R^3$, $—C{=}NR^2$, $—OR^2$, $—OC(O)R^2$, $—S(O)_t—R^2$, $—NR^2R^3$, $—NR^2C(O)R^3$, $—N{=}CR^2R^3$, wherein t is 0, 1, 2 or 3 and $R^8$ and $R^9$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen; and PG is a hydroxyl protecting group such as benzyl ether, methyl ester, benzoic acid ester, t-butyl ester, t-butyl ether (TBDMS, TBDPS), methoxymethyl ether (MOM), allyl ether, tetrahydropyranyl ether (THP). In some embodiments, PG is fluorenylmethyloxycarbonyl (FMOC).

In certain embodiments, a compound of interest and salts or solvates or stereoisomers thereof, include:

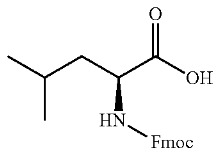

("Fmoc-Leucine")

Formulations, Dosages, and Routes of Administration

In general, an active agent (e.g., a compound of Formulae I-X, or a pharmaceutically acceptable salt or derivative thereof) is prepared in a pharmaceutically acceptable composition(s) for delivery to a host.

Pharmaceutically acceptable carriers preferred for use with active agents (and optionally one or more additional therapeutic agent) may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, and microparticles, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. A composition comprising an active agent (and optionally one or more additional therapeutic agent) may also be lyophilized using means well known in the art, for subsequent reconstitution and use according to the invention.

Formulations

An active agent is generally administered to an individual in need thereof in a formulation with a pharmaceutically acceptable excipient(s). A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc. For the purposes of the following description of formulations, "active agent" includes an active agent as described above, and optionally one or more additional therapeutic agent.

In a subject method, an active agent may be administered to the host using any convenient means capable of resulting in treatment of cardiac valve disease, e.g., CAVD. Thus, an active agent can be incorporated into a variety of formulations for therapeutic administration. For example, an active agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. In an exemplary embodiment, an active agent is formulated as a gel, as a solution, or in some other form suitable for intravaginal administration. In a further exemplary embodiment, an active agent is formulated as a gel, as a solution, or in some other form suitable for rectal (e.g., intrarectal) administration.

In pharmaceutical dosage forms, an active agent may be administered in the form of its pharmaceutically acceptable salts, or it may also be used alone or in appropriate association, as well as in combination, with other pharmaceutically active compounds. The following methods and excipients are merely exemplary and are in no way limiting.

In some embodiments, an active agent is formulated in an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

For oral preparations, an active agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An active agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

An active agent can be utilized in aerosol formulation to be administered via inhalation. An active agent can be formulated into pressurized acceptable propellants such as dichlorodifluoromethane, propane, nitrogen and the like.

Furthermore, an active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise the active agent(s) in a composition as a solution in sterile water, normal saline or another pharmaceutically acceptable carrier.

Unit dosage forms for intravaginal or intrarectal administration such as syrups, elixirs, gels, and suspensions may be provided wherein each dosage unit, for example, teaspoonful, tablespoonful, tablet, unit gel volume, or suppository, contains a predetermined amount of the composition containing one or more active agents.

The term "unit dosage form," as used herein, refers to physically discrete units suitable as unitary dosages for human and animal subjects, each unit containing a predetermined quantity of an active agent, calculated in an amount sufficient to produce the desired effect in association with a pharmaceutically acceptable diluent, carrier or vehicle. The specifications for a given active agent will depend in part on the particular compound employed and the effect to be achieved, and the pharmacodynamics associated with each compound in the host.

Other modes of administration will also find use with the subject invention. For instance, an active agent can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g. about 1% to about 2%.

An active agent can be administered as an injectable. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

An active agent will in some embodiments be formulated for vaginal delivery. A subject formulation for intravaginal administration comprises an active agent formulated as an intravaginal bioadhesive tablet, intravaginal bioadhesive microparticle, intravaginal cream, intravaginal lotion, intravaginal foam, intravaginal ointment, intravaginal paste, intravaginal solution, or intravaginal gel.

An active agent will in some embodiments be formulated for rectal delivery. A subject formulation for intrarectal administration comprises an active agent formulated as an intrarectal bioadhesive tablet, intrarectal bioadhesive microparticle, intrarectal cream, intrarectal lotion, intrarectal foam, intrarectal ointment, intrarectal paste, intrarectal solution, or intrarectal gel.

A subject formulation comprising an active agent includes one or more of an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, poly(ethylene glycol), sucrose or starch), a disintegrator (e.g., starch, carboxymethylcellulose, hydroxypropyl starch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol).

Tablets comprising an active agent may be coated with a suitable film-forming agent, e.g., hydroxypropylmethyl cellulose, hydroxypropyl cellulose or ethyl cellulose, to which a suitable excipient may optionally be added, e.g., a softener such as glycerol, propylene glycol, diethylphthalate, or glycerol triacetate; a filler such as sucrose, sorbitol, xylitol, glucose, or lactose; a colorant such as titanium hydroxide; and the like.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

Although the dosage used will vary depending on the clinical goals to be achieved, a suitable dosage range of an active agent is one which provides up to about 1 mg to about 5000 mg, e.g., from about 1 mg to about 25 mg, from about 25 mg to about 50 mg, from about 50 mg to about 100 mg, from about 100 mg to about 200 mg, from about 200 mg to about 250 mg, from about 250 mg to about 500 mg, from about 500 mg to about 1000 mg, or from about 1000 mg to about 5000 mg of an active agent, which can be administered in a single dose.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

In some embodiments, a suitable dose of a compound of Formulae I-X a pharmaceutically acceptable salt or derivative thereof, is in the range of from about 1 mg/kg body weight to about 500 mg/kg body weight, e.g., from about 5 mg/kg body weight to about 500 mg/kg body weight, from about 10 mg/kg body weight to about 500 mg/kg body weight, from about 20 mg/kg body weight to about 500 mg/kg body weight, from about 30 mg/kg body weight to about 500 mg/kg body weight, from about 40 mg/kg body weight to about 500 mg/kg body weight, from about 50 mg/kg body weight to about 500 mg/kg body weight, from about 60 mg/kg body weight to about 500 mg/kg body weight, from about 70 mg/kg body weight to about 500 mg/kg body weight, from about 80 mg/kg body weight to about 500 mg/kg body weight, from about 90 mg/kg body weight to about 500 mg/kg body weight, from about 100 mg/kg body weight to about 500 mg/kg body weight, from about 200 mg/kg body weight to about 500 mg/kg body weight, from about 300 mg/kg body weight to about 500 mg/kg body weight, or from about 400 mg/kg body weight to about 500 mg/kg body weight.

In some embodiments, a suitable dose of a compound of Formulae I-X or a pharmaceutically acceptable salt or derivative thereof, is in the range of from about 1 mg/kg body weight to about 5 mg/kg body weight, from about 5 mg/kg body weight to about 10 mg/kg body weight, from about 10 mg/kg body weight to about 20 mg/kg body weight, from about 20 mg/kg body weight to about 30 mg/kg body weight, from about 30 mg/kg body weight to about 40 mg/kg body weight, from about 40 mg/kg body weight to about 50 mg/kg body weight, from about 50 mg/kg body weight to about 100 mg/kg body weight, or from about 100 mg/kg body weight to about 500 mg/kg body weight.

In some embodiments, a single dose of an active agent is administered. In other embodiments, multiple doses of an active agent are administered. Where multiple doses are administered over a period of time, an active agent is administered, e.g., twice daily (qid), daily (qd), every other day (qod), every third day, three times per week (tiw), or twice per week (biw) over a period of time. For example, an active agent is administered qid, qd, qod, tiw, or biw over a period of from one day to about 2 years or more. For example, an active agent is administered at any of the aforementioned frequencies for one week, two weeks, one month, two months, six months, one year, or two years, or more, depending on various factors.

Where two different active agents are administered, e.g., any two or more compounds selected from compounds of Formulae I-X. a first active agent and a second active agent can be administered in separate formulations. A first active agent and a second active agent can be administered substantially simultaneously, or within about 30 minutes, about 1 hour, about 2 hours, about 4 hours, about 8 hours, about 16 hours, about 24 hours, about 36 hours, about 72 hours, about 4 days, about 7 days, or about 2 weeks of one another. The separate pharmaceutical compositions comprising the different agents may be administered using the same or different routes of administration in accordance with any medically acceptable method known in the art.

In some embodiments, a compound of Formula I is administered in combination with a compound of Formula III. In a nonlimiting example, XCT-790 (2E-3-(4-{[2,4-bis (trifluoromethyl)benzyl]oxy}-3-methoxyphenyl)-2-cyano-N-[5-(trifluoromethyl)-1,3,4-thiadiazol-2-yl]acrylamide) is administered in combination with GSK-837149A (4,4'-(carbonyldiimino)bis[N-(4-methyl-2-pyrimidinyl)-benzene-sulfonamide).

In some embodiments, a compound of Formula I is administered in combination with a compound of Formula II and a compound of Formula II. In a nonlimiting example, XCT-790 (2E-3-(4-{[2,4-bis(trifluoromethyl)benzyl]oxy}-3-methoxyphenyl)-2-cyano-N-[5-(trifluoromethyl)-1,3,4-thiadiazol-2-yl]acrylamide) is administered in combination with TG-003 ((Z)-1-(3-ethyl-5-methoxy-2,3-dihydrobenzothiazol-2-ylidene)propan-2-one) and GSK-837149A (4,4'-(carbonyldiimino)bis[N-(4-methyl-2-pyrimidinyl)-benzene-sulfonamide).

The compound of Formula I (e.g., XCT-790) can be administered prior to, concurrent with, or subsequent to the compound of Formula III (e.g., GSK-837149A) and/or the compound of Formula II (e.g., TG-003). If provided at the same time as the compound of Formula III (e.g., GSK-837149A) and/or the compound of Formula II (e.g., TG-003), the compound of Formula I (e.g., XCT-790) can be provided in the same or in a different composition. Thus, the three agents, or two of the three agents can be presented to the individual by way of concurrent therapy. By "concurrent therapy" is intended administration to a human subject such that the therapeutic effect of the combination of the substances is caused in the subject undergoing therapy. For example, concurrent therapy may be achieved by administering at least one therapeutically effective dose of a pharmaceutical composition comprising a compound of Formula I (e.g., XCT-790) and at least one therapeutically effective dose of a pharmaceutical composition comprising a compound of Formula III (e.g., GSK-837149A) and, optionally, at least one therapeutically effective dose of a composition comprising a compound of Formula II (e.g., TG-003) according to a particular dosing regimen. Administration of the separate pharmaceutical compositions can be at the same time (i.e., simultaneously) or at different times (i.e., sequentially, in either order, on the same day, or on different days), as long as the therapeutic effect of the combination of these compounds is caused in the subject undergoing therapy.

Routes of Administration

An active agent is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, transdermal, subcutaneous, intradermal, topical application, intravenous, vaginal, nasal, and other parenteral routes of administration. In some embodiments, an active agent is administered via an intravaginal route of administration. In other embodiments, an active agent is administered via an intrarectal route of administration. Routes of administration may be combined, if desired, or adjusted depending upon the agent and/or the desired effect. The composition can be administered in a single dose or in multiple doses.

An active agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, vaginal, transdermal, subcutaneous, intramuscular, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

An active agent can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as the degree of calcification of an aortic valve. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

Subjects Suitable for Treatment

A variety of hosts (wherein the term "host" is used interchangeably herein with the terms "subject" and "patient") are treatable according to the subject methods. Generally such hosts are "mammals" or "mammalian," where these terms are used broadly to describe organisms which are within the class mammalia, and primates (e.g., humans, chimpanzees, and monkeys). In many embodiments, the hosts will be humans. A suitable subject may be a subject that has been identified as at risk of or diagnosed with a cardiac valve disease, e.g., CAVD, including aortic sclerosis, and/or calcific aortic stenosis.

Total cholesterol, increased low-density lipoprotein (LDL) cholesterol, increased lipoprotein(a), increased triglycerides, decreased high-density lipoprotein cholesterol, male sex, cigarette smoking, hypertension, and diabetes mellitus have been reported to increase the incidence of aortic stenosis, and may contribute to endothelial dysfunction and leaflet damage. In addition, patients with familial hypercholesterolaemia develop peripheral vascular disease, coronary artery disease and aortic valve lesions, which calcify with age. Oxidised LDL (oxLDL) is implicated in vascular calcification associated with atherosclerosis. Elevated blood levels of oxLDL correlate with aortic valve calcification and fibrosis, and oxLDL accumulation in calcific, stenotic aortic valves has been described. Metabolic bone diseases, e.g., Paget's disease, secondary hyperparathyroidism and renal disease, as well as increased serum creatinine and calcium are also linked to progression of valve calcification. Patients with valve malformations, e.g. bicuspid aortic valve, are also at risk for valve calcification.

Additionally, patients identified as having a mutation in one of the multiple genes found to be associated with valve calcification may be identified as at-risk patients where preventative treatment is recommended, e.g., patients identified as having a mutation in one or more of NOTCH1, SMAD6, and GATA5. A suitable subject may also be a subject that has a NOTCH1 haploinsufficiency. Accordingly, a suitable subject may be a subject having one or more of the above clinical and/or genetic risk factors.

Kits, Containers, Devices, Delivery Systems

Kits with unit doses of the active agent, e.g. in oral, vaginal, rectal, transdermal, or injectable doses (e.g., for intramuscular, intravenous, or subcutaneous injection), are provided. In such kits, in addition to the containers containing the unit doses will be an informational package insert describing the use and attendant benefits of the drugs in treating or preventing cardiac valve disease. Suitable active agents and unit doses are those described herein above.

In many embodiments, a subject kit will further include instructions for practicing the subject methods or means for obtaining the same (e.g., a website URL directing the user to a webpage which provides the instructions), where these instructions are typically printed on a substrate, which substrate may be one or more of: a package insert, the packaging, formulation containers, and the like.

In some embodiments, a subject kit includes one or more components or features that increase patient compliance, e.g., a component or system to aid the patient in remembering to take the active agent at the appropriate time or interval. Such components include, but are not limited to, a calendaring system to aid the patient in remembering to take the active agent at the appropriate time or interval.

The present invention provides a delivery system comprising a compound of Formulae I-X, or a pharmaceutically acceptable salt or derivative thereof. In some embodiments, the delivery system is a delivery system that provides for injection of a formulation comprising an active agent subcutaneously, intravenously, or intramuscularly. In other embodiments, the delivery system is a vaginal or rectal delivery system.

In some embodiments, an active agent is packaged for oral administration. The present invention provides a packaging unit comprising daily dosage units of an active agent. For example, the packaging unit is in some embodiments a conventional blister pack or any other form that includes tablets, pills, and the like. The blister pack will contain the appropriate number of unit dosage forms, in a sealed blister pack with a cardboard, paperboard, foil, or plastic backing, and enclosed in a suitable cover. Each blister container may be numbered or otherwise labeled, e.g., starting with day 1.

In some embodiments, a subject delivery system comprises an injection device. Exemplary, non-limiting drug delivery devices include injections devices, such as pen injectors, and needle/syringe devices. In some embodiments, the invention provides an injection delivery device that is pre-loaded with a formulation comprising an effective amount of a compound of Formulae I-X or a pharmaceutically acceptable salt or derivative thereof. For example, a subject delivery device comprises an injection device pre-loaded with a single dose of a compound of Formulae I-X or a pharmaceutically acceptable salt or derivative thereof. A subject injection device can be re-usable or disposable.

Pen injectors are well known in the art. Exemplary devices which can be adapted for use in the present methods are any of a variety of pen injectors from Becton Dickinson, e.g., BD™ Pen, BD™ Pen II, BD™ Auto-Injector; a pen injector from Innoject, Inc.; any of the medication delivery pen devices discussed in U.S. Pat. Nos. 5,728,074, 6,096,010, 6,146,361, 6,248,095, 6,277,099, and 6,221,053; and the like. The medication delivery pen can be disposable, or reusable and refillable.

The present invention provides a delivery system for vaginal or rectal delivery of an active agent to the vagina or rectum of an individual. The delivery system comprises a device for insertion into the vagina or rectum. In some embodiments, the delivery system comprises an applicator for delivery of a formulation into the vagina or rectum; and a container that contains a formulation comprising an active agent. In these embodiments, the container (e.g., a tube) is adapted for delivering a formulation into the applicator. In other embodiments, the delivery system comprises a device that is inserted into the vagina or rectum, which device includes an active agent. For example, the device is coated with, impregnated with, or otherwise contains a formulation comprising the active agent.

In some embodiments, the vaginal or rectal delivery system is a tampon or tampon-like device that comprises a subject formulation. Drug delivery tampons are known in the art, and any such tampon can be used in conjunction with a subject drug delivery system. Drug delivery tampons are described in, e.g., U.S. Pat. No. 6,086,909. If a tampon or tampon-like device is used, there are numerous methods by which an active agent can be incorporated into the device. For example, the drug can be incorporated into a gel-like bioadhesive reservoir in the tip of the device. Alternatively, the drug can be in the form of a powdered material positioned at the tip of the tampon. The drug can also be absorbed into fibers at the tip of the tampon, for example, by dissolving the drug in a pharmaceutically acceptable carrier and absorbing the drug solution into the tampon fibers. The drug can also be dissolved in a coating material which is applied to the tip of the tampon. Alternatively, the drug can be incorporated into an insertable suppository which is placed in association with the tip of the tampon.

In other embodiments, the drug delivery device is a vaginal or rectal ring. Vaginal or rectal rings usually consist of an inert elastomer ring coated by another layer of elastomer containing an active agent to be delivered. The rings can be easily inserted, left in place for the desired period of time (e.g., up to 7 days), then removed by the user. The ring can optionally include a third, outer, rate-controlling elastomer layer which contains no drug. Optionally, the third ring can contain a second drug for a dual release ring. The drug can be incorporated into polyethylene glycol throughout the silicone elastomer ring to act as a reservoir for drug to be delivered.

In other embodiments, a subject vaginal or rectal delivery system is a vaginal or rectal sponge. The active agent is incorporated into a silicone matrix which is coated onto a cylindrical drug-free polyurethane sponge, as described in the literature.

Pessaries, tablets, and suppositories are other examples of drug delivery systems which can be used, e.g., in carrying out a method of the present disclosure. These systems have been described extensively in the literature.

Bioadhesive microparticles constitute still another drug delivery system suitable for use in the present invention. This system is a multi-phase liquid or semi-solid preparation which does not seep from the vagina or rectum as do many suppository formulations. The substances cling to the wall of the vagina or rectum and release the drug over a period of time. Many of these systems were designed for nasal use but can be used in the vagina or rectum as well (e.g. U.S. Pat. No. 4,756,907). The system may comprise microspheres with an active agent; and a surfactant for enhancing uptake of the drug. The microparticles have a diameter of 10-100 μm and can be prepared from starch, gelatin, albumin, collagen, or dextran.

Another system is a container comprising a subject formulation (e.g., a tube) that is adapted for use with an applicator. The active agent is incorporated into creams, lotions, foams, paste, ointments, and gels which can be applied to the vagina or rectum using an applicator. Processes for preparing pharmaceuticals in cream, lotion, foam, paste, ointment and gel formats can be found throughout the literature. An example of a suitable system is a standard fragrance free lotion formulation containing glycerol, ceramides, mineral oil, petrolatum, parabens, fragrance and water such as the product sold under the trademark JERGENS™ (Andrew Jergens Co., Cincinnati, Ohio). Suitable nontoxic pharmaceutically acceptable systems for use in the compositions of the present invention will be apparent to those skilled in the art of pharmaceutical formulations and examples are described in Remington's Pharmaceutical Sciences, 19th Edition, A. R.

Gennaro, ed., 1995. The choice of suitable carriers will depend on the exact nature of the particular vaginal or rectal dosage form desired, e.g., whether the active ingredient(s) is/are to be formulated into a cream, lotion, foam, ointment, paste, solution, or gel, as well as on the identity of the active ingredient(s). Other suitable delivery devices are those described in U.S. Pat. No. 6,476,079.

In some embodiments, more than one active agent is included in the kit, e.g., any two or more compounds selected from compounds of Formulae I-X. For example, the kit may comprise a compound of Formula I and a compound of Formula III, or a compound of Formula I, a compound of Formula II, and a compound of Formula III. In one embodiment, the kit comprises XCT-790, and GSK-837149A. In another embodiment, the kit comprises XCT-790, TG-003, and GSK-837149A.

Methods of Identifying a Candidate Compound for Treatment of Cardiac Valve Disease The present disclosure provides screening methods for identifying a candidate compound for treatment of cardiac valve disease. In some embodiments, the methods include contacting human NOTCH1$^{+/-}$ endothelial cells with a compound; performing targeted RNA sequencing (RNA-seq) to provide an expression profile for the human NOTCH1$^{+/-}$ endothelial cells resulting from the contacting, wherein the targeted RNA-seq comprises sequencing RNA transcripts for a plurality of the genes listed in Table 1; comparing the expression profile resulting from the contacting with an isogenic WT expression profile for the plurality of genes listed in Table 1; and identifying the compound as a candidate compound for treatment of cardiac valve disease when the expression profile resulting from the contacting is corrected to the isogenic WT expression profile.

TABLE 1

| Target # | Gene Symbol | Ensembl ID | RefSeq Transcript ID |
|---|---|---|---|
| 1 | NOTCH1 | ENSG00000148400 | NM_017617.3 |
| 2 | SOX7 | ENSG00000171056 | NM_031439.3 |
| 3 | TCF4 | ENSG00000196628 | NM_003199 |
| 4 | SMAD1 | ENSG00000170365 | NM_005900 |
| 5 | NOTCH4 | ENSG00000204301 | NM_004557.3 |
| 6 | HES1 | ENSG00000114315 | NM_005524 |
| 7 | ACE | ENSG00000159640 | NM_000789.3 |
| 8 | GREM1 | ENSG00000166923 | NM_013372 |
| 9 | CHMP2A | ENSG00000130724 | NM_014453.3 |
| 10 | C1orf43 | ENSG00000143612 | NM_015449 |
| 11 | REEP5 | ENSG00000129625 | NM_005669.4 |
| 12 | JAG2 | ENSG00000184916 | NM_002226.4 |
| 13 | ARHGEF17 | ENSG00000110237 | NM_014786.3 |
| 14 | MMP10 | ENSG00000166670 | NM_002425.2 |
| 15 | IRF6 | ENSG00000117595 | NM_006147.3 |
| 16 | DKK3 | ENSG00000050165 | NM_013253 |
| 17 | ANO4 | ENSG00000151572 | NM_001286615.1 |
| 18 | MMP19 | ENSG00000123342 | NM_001272101.1 |
| 19 | SOX11 | ENSG00000176887 | NM_003108.3 |
| 20 | SOX13 | ENSG00000143842 | NM_005686.2 |

TABLE 1-continued

| Target # | Gene Symbol | Ensembl ID | RefSeq Transcript ID |
|---|---|---|---|
| 21 | RUNX2 | ENSG00000124813 | NM_001024630 |
| 22 | RUNX1 | ENSG00000159216 | NM_001001890.2 |
| 23 | ITGA5 | ENSG00000161638 | NM_002205.2 |
| 24 | CD34 | ENSG00000174059 | NM_001773.2 |
| 25 | ETS1 | ENSG00000134954 | NM_005238.3 |
| 26 | CSDA | ENSG00000060138 | NM_003651.4 |
| 27 | IGFBP3 | ENSG00000146674 | NM_000598.4 |
| 28 | SDPR | ENSG00000168497 | NM_004657.5 |
| 29 | CDH5 | ENSG00000179776 | NM_001795.3 |
| 30 | LXN | ENSG00000079257 | NM_020169.3 |
| 31 | CXCR4 | ENSG00000121966 | NM_003467 |
| 32 | TNFSF4 | ENSG00000117586 | NM_003326 |
| 33 | GJA4 | ENSG00000187513 | NM_002060.2 |
| 34 | NRP1 | ENSG00000099250 | NM_003873 |
| 35 | CD24P4 | ENSG00000185275 | NM_013230.3 |
| 36 | HMGA2 | ENSG00000149948 | NM_003483 |
| 37 | THSD1 | ENSG00000136114 | NM_018676.3 |
| 38 | RASSF2 | ENSG00000101265 | NM_014737.2 |
| 39 | HHIP | ENSG00000164161 | NM_022475.2 |
| 40 | TERF1 | ENSG00000147601 | NM_017489.2 |
| 41 | NID2 | ENSG00000087303 | NM_007361.3 |
| 42 | ALDH1A1 | ENSG00000165092 | NM_000689.4 |
| 43 | HEY1 | ENSG00000164683 | NM_001040708.1 |
| 44 | ETS2 | ENSG00000157557 | NM_005239.5 |
| 45 | ITGA9 | ENSG00000144668 | NM_002207.2 |
| 46 | NRCAM | ENSG00000091129 | NM_001193582 |
| 47 | HOXB5 | ENSG00000120075 | NM_002147.3 |
| 48 | HOXB6 | ENSG00000108511 | NM_018952.4 |
| 49 | PRDM1 | ENSG00000057657 | NM_001198.3 |
| 50 | C10orf10 | ENSG00000165507 | NM_007021.3 |
| 51 | ALDH2 | ENSG00000111275 | NM_000690.3 |
| 52 | COL12A1 | ENSG00000111799 | NM_004370.5 |
| 53 | SNCA | ENSG00000145335 | NM_000345.3 |
| 54 | SFRP1 | ENSG00000104332 | NM_003012.4 |
| 55 | NPPB | ENSG00000120937 | NM_002521.2 |
| 56 | CA8 | ENSG00000178538 | NM_004056.4 |
| 57 | GNA14 | ENSG00000156049 | NM_004297.3 |
| 58 | VCAN | ENSG00000038427 | NM_001164097 |
| 59 | HOXB7 | ENSG00000120087 | NM_004502.3 |
| 60 | ITGA8 | ENSG00000077943 | NM_003638 |
| 61 | ACP5 | ENSG00000102575 | NM_001111034.1 |
| 62 | TMEM178 | ENSG00000152154 | NM_152390 |
| 63 | HOXB3 | ENSG00000120093 | NM_002146.4 |
| 64 | PLAGL1 | ENSG00000118495 | NM_001080952.1 |
| 65 | NR5A2 | ENSG00000116833 | NM_205860.2 |
| 66 | VLDLR | ENSG00000147852 | NM_003383.3 |
| 67 | BICD1 | ENSG00000151746 | NM_001003398.1 |
| 68 | MAML3 | ENSG00000196782 | NM_018717.4 |
| 69 | NRG3 | ENSG00000185737 | NM_001010848.3 |
| 70 | FOXF1 | ENSG00000103241 | NM_001451.2 |
| 71 | CXCL12 | ENSG00000107562 | NM_000609 |
| 72 | HLX | ENSG00000136630 | NM_021958.3 |
| 73 | MEIS2 | ENSG00000134138 | NM_002399 |
| 74 | HOXB4 | ENSG00000182742 | NM_024015.4 |
| 75 | TCF7L1 | ENSG00000152284 | NM_031283.2 |
| 76 | FGF2 | ENSG00000138685 | NM_002006.4 |
| 77 | ALX1 | ENSG00000180318 | NM_006982.2 |
| 78 | CARHSP1 | ENSG00000153048 | NM_001278260 |
| 79 | DNER | ENSG00000187957 | NM_139072.3 |
| 80 | TGFBR3 | ENSG00000069702 | NM_001195683.1 |
| 81 | TOX3 | ENSG00000103460 | NM_001146188 |
| 82 | PDE2A | ENSG00000186642 | NM_001143839.3 |
| 83 | HOXB2 | ENSG00000173917 | NM_002145.3 |
| 84 | CA2 | ENSG00000104267 | NM_000067.2 |
| 85 | COL15A1 | ENSG00000204291 | NM_001855.4 |
| 86 | PPARG | ENSG00000132170 | NM_005037.5 |
| 87 | IER3 | ENSG00000137331 | NM_003897.3 |
| 88 | TNFRSF25 | ENSG00000215788 | NM_148970 |
| 89 | FLT4 | ENSG00000037280 | NM_182925 |
| 90 | PRRX1 | ENSG00000116132 | NM_006902.4 |
| 91 | HOXD1 | ENSG00000128645 | NM_024501.2 |
| 92 | AFF3 | ENSG00000144218 | NM_001025108.1 |
| 93 | CXCR7 | ENSG00000144476 | NM_020311.2 |
| 94 | PDE3A | ENSG00000172572 | NM_000921.4 |
| 95 | SMTN | ENSG00000183963 | NM_134270 |
| 96 | BMP6 | ENSG00000153162 | NM_001718.4 |
| 97 | BMP4 | ENSG00000125378 | NM_001202.3 |
| 98 | PGF | ENSG00000119630 | NM_002632 |

TABLE 1-continued

| Target # | Gene Symbol | Ensembl ID | RefSeq Transcript ID |
|---|---|---|---|
| 99 | TXNIP | ENSG00000117289 | NM_006472.4 |
| 100 | DACH1 | ENSG00000165659 | NM_080759.5 |
| 101 | F2R | ENSG00000181104 | NM_001992.3 |
| 102 | F2RL2 | ENSG00000164220 | NM_004101.3 |
| 103 | THBS1 | ENSG00000137801 | NM_003246.2 |
| 104 | FAM124B | ENSG00000124019 | NM_001122779.1 |
| 105 | PLOD2 | ENSG00000152952 | NM_182943.2 |
| 106 | COX6A1 | ENSG00000111775 | NM_004373.3 |
| 107 | KIAA0494 | ENSG00000159658 | NM_014774.2 |
| 108 | RNF19A | ENSG00000034677 | NM_001280539.1 |
| 109 | CLEC14A | ENSG00000176435 | NM_175060.2 |
| 110 | DIAPH2 | ENSG00000147202 | NM_006729.4 |
| 111 | NDUFA12 | ENSG00000184752 | NM_018838.4 |
| 112 | FAM89A | ENSG00000182118 | NM_198552.2 |
| 113 | NNMT | ENSG00000166741 | NM_006169.2 |
| 114 | MLF1 | ENSG00000178053 | NM_001130156.2 |
| 115 | C1orf54 | ENSG00000118292 | NM_001301040 |
| 116 | HAPLN1 | ENSG00000145681 | NM_001884.3 |
| 117 | IL1RL1 | ENSG00000115602 | NM_003856.3 |
| 118 | ITPKB | ENSG00000143772 | NM_002221.3 |
| 119 | CD97 | ENSG00000123146 | NM_001025160.2 |

In some embodiments, the plurality includes one or more or all of the following genes: NOTCH1, SOX7, TCF4, and SMAD1. In some embodiments, the plurality includes NOTCH1, SOX7, TCF4, and SMAD1 and at least 1, e.g., 2, 3, 4, 5, 6, 7, 8, 9, 10, 15, 20, 30, 40, 50, 60, 70, 80, 90, 100, 110, or 115 additional genes selected from Table 1. In some embodiments, the plurality includes at least one housekeeping gene. In some embodiments, the at least one housekeeping gene is selected from CHMP2A, C1orf43, and REEP5. In some embodiments, one, two or all of the housekeeping genes CHMP2A, C1orf43, and REEP5 are excluded from the expression profile. For example, in some embodiments, the targeted RNA-seq does not include sequencing RNA transcripts for one, two or all of the housekeeping genes CHMP2A, C1orf43, and REEP5.

In some embodiments, the human NOTCH1$^{+/-}$ endothelial cells are derived from human induced pluripotent stem cells (iPSC) derived from a subject having CAVD, e.g., iPSC derived from fibroblasts of a subject having CAVD. In other embodiments, wild type cells, e.g., wild type human endothelial cells, genetically engineered to have the N1 mutation, are used in place of human NOTCH1$^{+/-}$ endothelial cells derived from human induced pluripotent stem cells (iPSC) derived from a subject having CAVD. In still other embodiments, endothelial cells are derived from human induced pluripotent stem cells (iPSC) e.g., iPSC derived from fibroblasts, wherein the endothelial cells are genetically engineered to have the N1 mutation.

One or more suitable machine learning algorithms, e.g., K-nearest neighbors (KNN) algorithm, may be utilized to determine when the expression profile resulting from the contacting is corrected to the isogenic WT expression profile. A suitable isogenic WT expression profile can be obtained, e.g., by deriving isogenic control lines, wherein the N1 mutation is corrected using an appropriate gene editing tool, e.g., Meganuclease, TALEN, ZFN, or CRISPR/Cas system.

EXEMPLARY NON-LIMITING ASPECTS OF THE DISCLOSURE

Aspects, including embodiments, of the present subject matter described above may be beneficial alone or in combination, with one or more other aspects or embodiments. Without limiting the foregoing description, certain non-limiting aspects of the disclosure are provided below. As will be apparent to those of ordinary skill in the art upon reading this disclosure, each of the individually numbered aspects may be used or combined with any of the preceding or following individually numbered aspects. This is intended to provide support for all such combinations of aspects and is not limited to combinations of aspects explicitly provided below. It will be apparent to one of ordinary skill in the art that various changes and modifications can be made without departing from the spirit or scope of the invention.

1. A method of treating cardiac valve disease by administering to a subject in need thereof a therapeutically effective amount of a compound of Formula I:

(I)

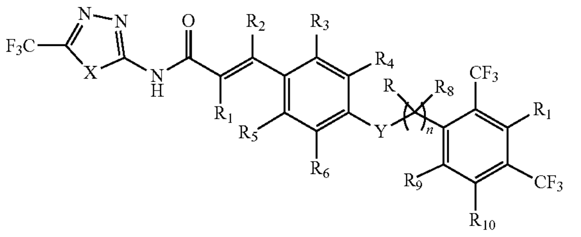

or a pharmaceutically acceptable salt, solvate or prodrug thereof, wherein:

n is an integer from 1 to 8;

X is O or S;

Y is O or S; and each of $R^1$, $R^2$, $R^3$, $R^4$, $R^5$, $R^6$, $R^7$, $R^8$, $R^9$, $R^{10}$ and $R^{11}$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, $-COR^{12}$, $-C(O)OR^{12}$, $-C(O)NR^{12}R^{13}$, $-C{=}NR^{12}$, $-OR^{12}$, $-OC(O)R^{12}$, $-S(O)_t-R^7$, $-NR^{12}R^{13}$, $-NR^{12}C(O)R^{13}$, $-N{=}CR^{12}R^{13}$, wherein t is 0, 1, 2 or 3 and $R^{12}$ and $R^{13}$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen.

2. The method according to 1, wherein $R^1$ is cyano.
3. The method according to any one of 1-2, wherein $R^1$ is methoxy.
4. The method according to any one of 1-3, wherein X is S.
5. The method according to any one of 1-4, wherein Y is O.
6. The method according to any one of 1-5, wherein n is 1.
7. The method according to 1, wherein the compound is XCT-790 (2E-3-(4-{[2,4-bis(trifluoromethyl)benzyl]oxy}-3-methoxyphenyl)-2-cyano-N-[5-(trifluoromethyl)-1,3,4-thiadiazol-2-yl]acrylamide):

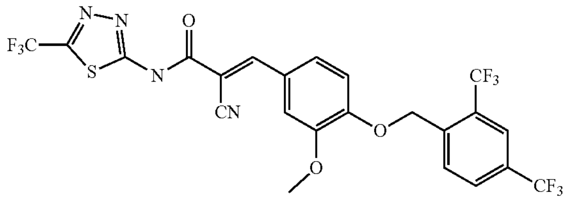

8. The method according to any one of 1-7, wherein the cardiac valve disease is a calcific aortic valve disease.

9. The method according to any one of 1-7, wherein the subject has a NOTCH1 haploinsufficiency, the subject is at risk of developing calcific aortic valve disease, and/or the subject has been diagnosed as having calcific aortic valve disease.

10. A method of treating cardiac valve disease by administering to a subject in need thereof a therapeutically effective amount of a compound of Formula II:

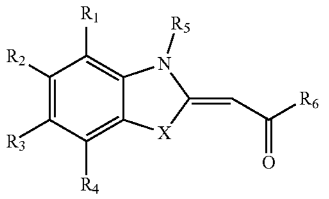

(II)

or a pharmaceutically acceptable salt, solvate or prodrug thereof, wherein:

X is O or S; and each of $R^1$, $R^2$, $R^3$, $R^4$, $R^5$ and $R^6$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, $—COR^{12}$, $—C(O)OR^{12}$, $—C(O)NR^{12}R^{13}$, $—C{=}NR^{12}$, $—OR^{12}$, $—OC(O)R^{12}$, $—S(O)_t—R^7$, $—NR^{12}R^{13}$, $—NR^{12}C(O)R^{13}$, $—N{=}CR^{12}R^{13}$, wherein t is 0, 1, 2 or 3 and $R^{12}$ and $R^{13}$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen.

11. The method according 10, wherein $R^2$ is methoxy.

12. The method according to any one of 10-11, wherein $R^5$ is methyl.

13. The method according to any one of 10-12, wherein $R^6$ is methyl.

14. The method according to any one of 10-13, wherein X is O.

15. The method according to 10, wherein the compound is TG-003 ((Z)-1-(3-ethyl-5-methoxy-2,3-dihydrobenzothiazol-2-ylidene)propan-2-one):

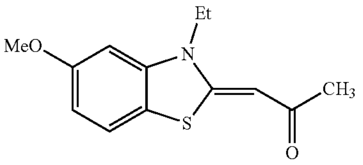 [SMILES: CCN1/C(=C/C(C)=O)Sc2ccc(OC)cc21]

16. The method according to any one of 10-15, wherein the cardiac valve disease is a calcific aortic valve disease.

17. The method according to any one of 10-15, wherein the subject has a NOTCH1 haploinsufficiency, the subject is at risk of developing calcific aortic valve disease, and/or the subject has been diagnosed as having calcific aortic valve disease.

18. A method of treating cardiac valve disease by administering to a subject in need thereof a therapeutically effective amount of a compound of Formula III:

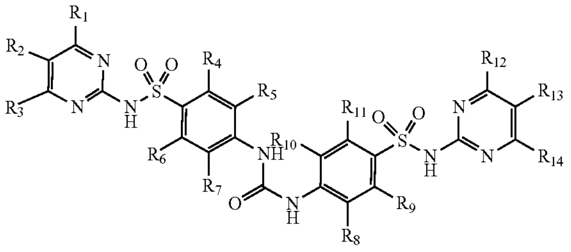

(III)

or a pharmaceutically acceptable salt, solvate or prodrug thereof, wherein:

each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, $—COR^{15}$, $—C(O)OR^{15}$, $—C(O)NR^{15}R^{16}$, $—C{=}NR^{15}$, $—OR^{15}$, $—OC(O)R^{15}$, $—S(O)_t—R^{15}$, $—NR^{15}R^{16}$, $—NR^{15}C(O)R^{16}$, $—N{=}CR^{15}R^{16}$, wherein t is 0, 1, 2 or 3 and $R^{15}$ and $R^{15}$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen.

19. The method according to 18, wherein $R^3$ is methyl.

20. The method according to any one of 18-19, wherein $R^{12}$ is methyl.

21. The method according to 18, wherein the compound is GSK-837149A (4,4'-(carbonyldiimino)bis[N-(4-methyl-2-pyrimidinyl)-benzenesulfonamide):

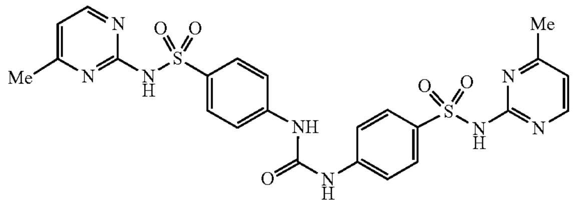 [SMILES: Cc1ccnc(NS(=O)(=O)c2ccc(NC(=O)Nc3ccc(S(=O)(=O)Nc4nccc(C)n4)cc3)cc2)n1]

22. The method according to any one of 18-21, wherein the cardiac valve disease is a calcific aortic valve disease.

23. The method according to any one of 18-21, wherein the subject has a NOTCH1 haploinsufficiency, the subject is at risk of developing calcific aortic valve disease, and/or the subject has been diagnosed as having calcific aortic valve disease.

24. A method of treating cardiac valve disease by administering to a subject in need thereof a therapeutically effective amount of a compound of Formula IV:

(IV)

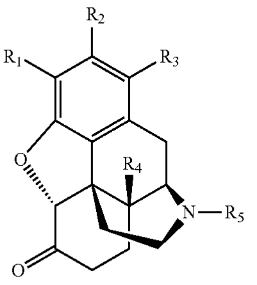

or a pharmaceutically acceptable salt, solvate or prodrug thereof, wherein:

each of $R^1$, $R^2$, $R^3$, $R^4$ and $R^5$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —$COR^{15}$, —$C(O)OR^{15}$, —$C(O)NR^{15}R^{16}$, —$C{=}NR^{15}$, —$OR^{15}$, —$OC(O)R^{15}$, —$S(O)_t$—$R^{15}$, —$NR^{15}R^{16}$, —$NR^{15}C(O)R^{16}$, —$N{=}CR^{15}R^{16}$, wherein t is 0, 1, 2 or 3 and $R^{15}$ and $R^{15}$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen.

25. The method according to 24, wherein $R^1$ is hydroxyl.

26. The method according to any one of 24-25, wherein $R^4$ is hydroxyl.

27. The method according to any one of 24-26, wherein $R^5$ is allyl.

28. The method according to 24, wherein the compound is Naloxone ((4R,4aS,7aR,12bS)-4a,9-dihydroxy-3-prop-2-enyl-2,4,5,6,7a,13-hexahydro-1H-4,12-methanobenzofuro[3,2-e]isoquinoline-7-one):

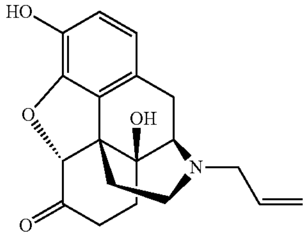

29. The method according to any one of 24-28, wherein the cardiac valve disease is a calcific aortic valve disease.

30. The method according to any one of 24-28, wherein the subject has a NOTCH1 haploinsufficiency, the subject is at risk of developing calcific aortic valve disease, and/or the subject has been diagnosed as having calcific aortic valve disease.

31. A method of treating cardiac valve disease by administering to a subject in need thereof a therapeutically effective amount of a compound of Formula V:

(V)

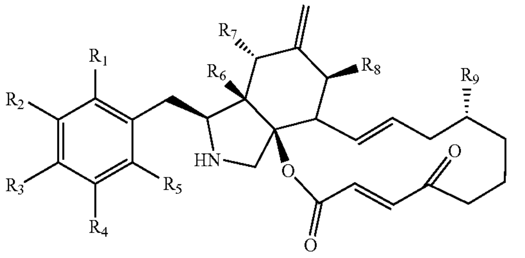

or a pharmaceutically acceptable salt, solvate or prodrug thereof, wherein:

each of $R^1$, $R^2$, $R^3$, $R^4$, $R^5$, $R^6$, $R^7$, $R^8$ and $R^9$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, —$COR^{10}$, —$C(O)OR^{10}$, —$C(O)NR^{10}R^{11}$, —$C{=}NR^{10}$, —$OR^{10}$, —$OC(O)R^{10}$, —$S(O)_t$—$R^{10}$, —$NR^{10}R^{11}$, —$NR^{10}C(O)R^{11}$, —$N{=}CR^{10}R^{11}$, wherein t is 0, 1, 2 or 3 and $R^{10}$ and $R^{11}$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen.

32. The method according to 31, wherein $R^6$ is hydrogen.

33. The method according to any one of 31-32, wherein $R^7$ is methyl.

34. The method according to any one of 31-33, wherein $R^8$ is hydroxyl.

35. The method according to any one of 31-34, wherein $R^9$ is methyl.

36. The method according to 31, wherein the compound is Cytochalasin:

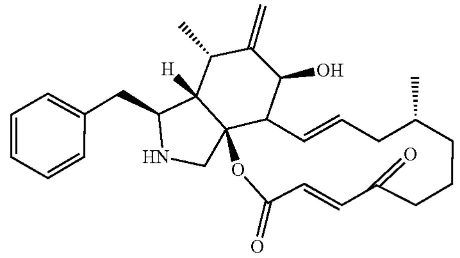 [SMILES: C=C1[C@@H](O)C2/C=C/C[C@H](C)CCCC(=O)/C=C/C(=O)O[C@]23CN[C@@H](Cc2ccccc2)[C@@H]3[C@@H]1C]

37. The method according to any one of 31-36, wherein the cardiac valve disease is a calcific aortic valve disease.

38. The method according to any one of 31-36, wherein the subject has a NOTCH1 haploinsufficiency, the subject is at risk of developing calcific aortic valve disease, and/or the subject has been diagnosed as having calcific aortic valve disease.

39. A method of treating cardiac valve disease by administering to a subject in need thereof a therapeutically effective amount of a compound of Formula VI:

(VI)

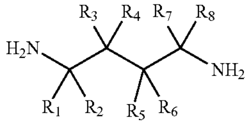

or a pharmaceutically acceptable salt, solvate or prodrug thereof, wherein:

each of $R^1$, $R^2$, $R^3$, $R^4$, $R^5$, $R^6$, $R^7$ and $R^8$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, $—COR^9$, $—C(O)OR^9$, $—C(O)NR^9R^{10}$, $—C{=}NR^9$, $—OR^9$, $—OC(O)R^9$, $—S(O)_t—R^9$, $—NR^9R^{10}$, $—NR^9C(O)R^{10}$, $—N{=}CR^9R^{10}$, wherein t is 0, 1, 2 or 3 and $R^9$ and $R^{10}$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen.

40. The method according to 39, wherein each of $R^1$, $R^2$, $R^3$, $R^4$, $R^5$, $R^6$, $R^7$ and $R^8$ are hydrogen.

41. The method according to 39, wherein the compound is Putrescine (Butane-1,4-diamine):

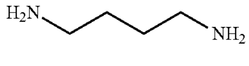

42. The method according to any one of 39-41, wherein the cardiac valve disease is a calcific aortic valve disease.

43. The method according to any one of 39-41, wherein the subject has a NOTCH1 haploinsufficiency, the subject is at risk of developing calcific aortic valve disease, and/or the subject has been diagnosed as having calcific aortic valve disease.

44. A method of treating cardiac valve disease by administering to a subject in need thereof a therapeutically effective amount of a compound of Formula VI:

(VII)

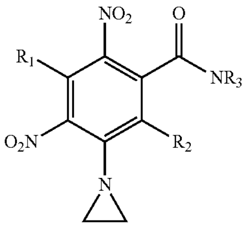

or a pharmaceutically acceptable salt, solvate or prodrug thereof, wherein:

each of $R^1$, $R^2$ and $R^3$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, $—COR^4$, $—C(O)OR^4$, $—C(O)NR^4R^5$, $—C{=}NR^4$, $—OR^4$, $—OC(O)R^4$, $—S(O)_t—R^4$, $—NR^4R^5$, $—NR^4C(O)R^5$, $—N{=}CR^4R^5$, wherein t is 0, 1, 2 or 3 and $R^4$ and $R^5$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen.

45. The method according to 44, wherein each of $R^1$, $R^2$ and $R^3$ are hydrogen.

46. The method according to 44, wherein the compound is CB-1954 (5-(1-aziridinyl)-2,4-dinitrobenzamide):

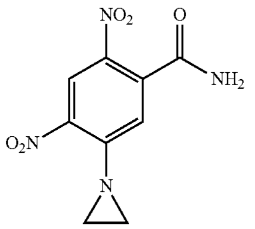 [SMILES: NC(=O)c1cc(N2CC2)c([N+](=O)[O-])cc1[N+](=O)[O-]]

47. The method according to any one of 44-46, wherein the cardiac valve disease is a calcific aortic valve disease.

48. The method according to any one of 44-46, wherein the subject has a NOTCH1 haploinsufficiency, the subject is at risk of developing calcific aortic valve disease, and/or the subject has been diagnosed as having calcific aortic valve disease.

49. A method of treating cardiac valve disease by administering to a subject in need thereof a therapeutically effective amount of a compound of Formula VIII:

(VIII)

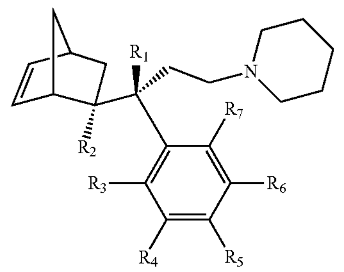

or a pharmaceutically acceptable salt, solvate or prodrug thereof, wherein:

each of $R^1$, $R^2$, $R^3$, $R^4$, $R^5$, $R^6$ and $R^7$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, $—COR^8$, $—C(O)OR^8$, $—C(O)NR^8R^9$, $—C{=}NR^8$, $—OR^9$, $—OC(O)R^8$, $—S(O)_t—R^8$, $—NR^8R^9$, $—NR^8C(O)R^9$, $—N{=}CR^8R^9$, wherein t is 0, 1, 2 or 3 and $R^8$ and $R^9$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen.

50. The method according to 49, wherein $R^1$ is hydrogen.

51. The method according to 49, wherein $R^1$ is hydroxyl.

52. The method according to any one of 49-51, wherein each of $R^2$, $R^3$, $R^4$, $R^5$, $R^6$ and $R^7$ are hydrogen.

53. The method according to 49, wherein the compound is biperiden ((1RS,2SR,4RS)-1-(bicyclo[2.2.1]hept-5-en-2-yl)-1-phenyl-3-(piperidin-1-yl)propan-1-ol)):

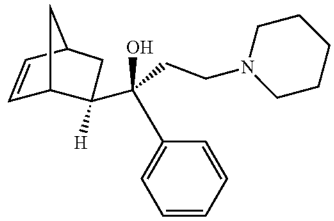 [SMILES: O[C@@](CCN1CCCCC1)(c1ccccc1)[C@@H]1CC2C=CC1C2]

54. The method according to any one of 49-53, wherein the cardiac valve disease is a calcific aortic valve disease.

55. The method according to any one of 49-53, wherein the subject has a NOTCH1 haploinsufficiency, the subject is at risk of developing calcific aortic valve disease, and/or the subject has been diagnosed as having calcific aortic valve disease.

56. A method of treating cardiac valve disease by administering to a subject in need thereof a therapeutically effective amount of a compound of Formula IX:

(IX)

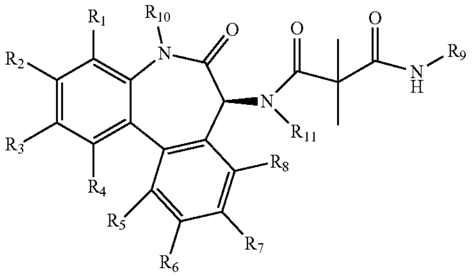

or a pharmaceutically acceptable salt, solvate or prodrug thereof, wherein:

each of $R^1$, $R^2$, $R^3$, $R^4$, $R^5$, $R^6$, $R^7$, $R^8$, $R^9$, $R^{10}$ and $R^{11}$ are independently selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, $—COR^{12}$, $—C(O)OR^{12}$, $—C(O)NR^{12}R^{13}$, $—C{=}NR^{12}$, $—OR^{12}$, $—OC(O)R^{12}$, $—S(O)_t—R^{12}$, $—NR^{12}R^{13}$, $—NR^{12}C(O)R^{13}$, $—N{=}CR^{12}R^{13}$, wherein t is 0, 1, 2 or 3 and $R^{12}$ and $R^{13}$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen.

57. The method according to 56, wherein each of $R^1$, $R^2$, $R^3$, $R^4$, $R^5$, $R^6$, $R^7$, $R^8$, $R^{10}$ and $R^{11}$ are hydrogen.

58. The method according to 56, wherein $R^9$ is pentafluoroethyl.

59. The method according to 56, wherein the compound is RO-4929097 ((2,2-dimethyl-N-[(10S)-9-oxo-8-azatricyclo[9.4.0.02,7]pentadeca-1,2,4,6,11,13-hexaene-10-yl]-N'-(2,2,3,3,3-pentafluoropropyl)propanediamide):

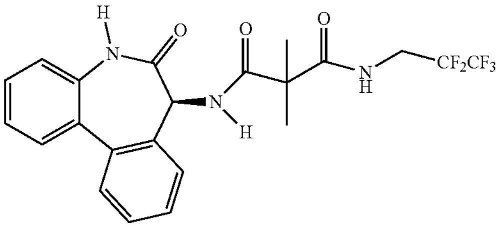

60. The method according to any one of 56-59, wherein the cardiac valve disease is a calcific aortic valve disease.

61. The method according to any one of 56-59, wherein the subject has a NOTCH1 haploinsufficiency, the subject is at risk of developing calcific aortic valve disease, and/or the subject has been diagnosed as having calcific aortic valve disease.

62. A method of treating cardiac valve disease by administering to a subject in need thereof a therapeutically effective amount of a compound of Formula X:

(X)

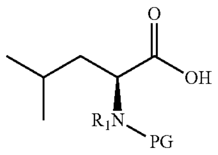

or a pharmaceutically acceptable salt, solvate or prodrug thereof, wherein:

$R^1$ is selected from hydrogen, alkyl, substituted alkyl, aryl, substituted aryl, heterocycloalkyl, substituted heterocycloalkyl, heteroaryl, substituted heteroaryl, hydroxyl, alkoxyl, substituted alkoxyl, substituted acyloxy, alkoxycarbonyl, substituted alkoxycarbonyl, thiol, acyl, amino, substituted amino, aminoacyl, acylamino, azido, carboxyl, carboxylalkyl, cyano, halogen, nitro, $—COR^2$, $—C(O)OR^2$, $—C(O)NR^2R^3$, $—C{=}NR^2$, $—OR^2$, $—OC(O)R^2$, $—S(O)_t—R^2$, $—NR^2R^3$, $—NR^2C(O)R^3$, $—N{=}CR^2R^3$, wherein t is 0, 1, 2 or 3 and $R^1$ and $R^9$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen; and PG is a hydroxyl protecting group selected from the group consisting of a benzyl ether, methyl ester, benzoic acid ester, t-butyl ester, t-butyl ether (TBDMS, TBDPS), methoxymethyl ether (MOM), allyl ether, tetrahydropyranyl ether (THP), a fluorenylmethyloxycarbonyl (Fmoc).

63. The method according to 62, wherein each of $R^1$ is hydrogen.

64. The method according to 63, wherein PG is fluorenylmethyloxycarbonyl (Fmoc).

65. The method according to 64, wherein the compound is Fmoc-leucine:

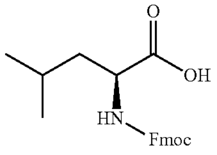

66. The method according to any one of 62-65, wherein the cardiac valve disease is a calcific aortic valve disease.

67. The method according to any one of 62-65, wherein the subject has a NOTCH1 haploinsufficiency, the subject is at risk of developing calcific aortic valve disease, and/or the subject has been diagnosed as having calcific aortic valve disease.

68. A method of identifying a candidate compound for treatment of cardiac valve disease, the method comprising:

contacting human NOTCH1$^{+/-}$ endothelial cells with a compound;

performing targeted RNA sequencing (RNA-seq) to provide an expression profile for the human NOTCH1$^{+/-}$ endothelial cells resulting from the contacting, wherein the targeted RNA-seq comprises sequencing RNA transcripts fora plurality of genes selected from Table 1;

comparing the expression profile resulting from the contacting with an isogenic WT expression profile; and identifying the compound as a candidate compound for treatment of cardiac valve disease when the expression profile resulting from the contacting is corrected to the isogenic WT expression profile.

69. The method of 68, wherein the plurality of genes comprises one or more or all of NOTCH1, SOX7, TCF4, and SMAD1.

70. The method of 68 or 69, wherein the plurality of genes further comprises one or more or all of NOTCH4, HES1, ACE, and GREM1.

71. The method of any one of 68-70, wherein the plurality of genes further comprises one or more or all of CHMP2A, C1orf43, and REEP5.

72. The method of any one of 68-71, wherein the plurality of genes further comprises one or more or all of JAG2, ARHGEF17, MMP10, IRF6, DKK3, ANO4, MMP19, SOX11, SOX13, RUNX2, and RUNX1.

73. The method of any one of 68-72, wherein the plurality of genes further comprises one or more or all of ITGA5, CD34, ETS1, CSDA, IGFBP3, SDPR, CDH5, LXN, CXCR4, TNFSF4, GJA4, NRP1, CD24P4, HMGA2, THSD1, RASSF2, HHIP, TERF1, NID2, ALDH1A1, HEY1, ETS2, ITGA9, NRCAM, HOXB5, HOXB6, PRDM1, C10orf10, ALDH2, COL12A1, SNCA, SFRP1, NPPB, CA8, GNA14, VCAN, HOXB7, ITGA8, ACP5, TMEM178, HOXB3, PLAGLI, NR5A2, VLDLR, BICD1, MAML3, NRG3, FOXF1, CXCL12, HLX, MEIS2, HOXB4, TCF7L1, FGF2, ALX1, CARHSP1, DNER, TGFBR3, TOX3, PDE2A, HOXB2, CA2, COL15A1, PPARG, IER3, TNFRSF25, FLT4, PRRX1, HOXD1, AFF3, CXCR7, PDE3A, SMTN, BMP6, BMP4, PGF, TXNIP, and DACH1.

74. The method of any one of 68-73, wherein the plurality of genes further comprises one or more or all of F2R, F2RL2, THBS1, FAM124B, PLOD2, COX6A1, KIAA0494, RNF19A, CLEC14A, DIAPH2, NDUFA12, FAM89A, NNMT, MLF1, C1orf54, HAPLN1, IL1RL1, ITPKB, and CD97.

75. The method of any one of 68-74, wherein the human NOTCH1$^{+/-}$ endothelial cells are derived from human induced pluripotent stem cells (iPSC) derived from a subject having CAVD.

76. The method of 75, wherein the iPSC are derived from fibroblasts of a subject having CAVD.

77. The method of any one of 68-76, wherein the identifying comprises applying a machine learning algorithm to determine when the expression profile resulting from the contacting is corrected to the isogenic WT expression profile.

78. A composition comprising at least one compound of any one of Formulae I-X for use in the treatment of cardiac valve disease.

EXAMPLES

The following examples are put forth so as to provide those of ordinary skill in the art with a complete disclosure and description of how to make and use the present invention, and are not intended to limit the scope of the invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Materials and Methods

The following materials and methods generally apply to the results presented in the Examples described herein except where noted otherwise. Additional materials and methods are provided below for each Example as applicable.

Isogenic iPSC Derivation and EC Differentiation

Figure 9A:
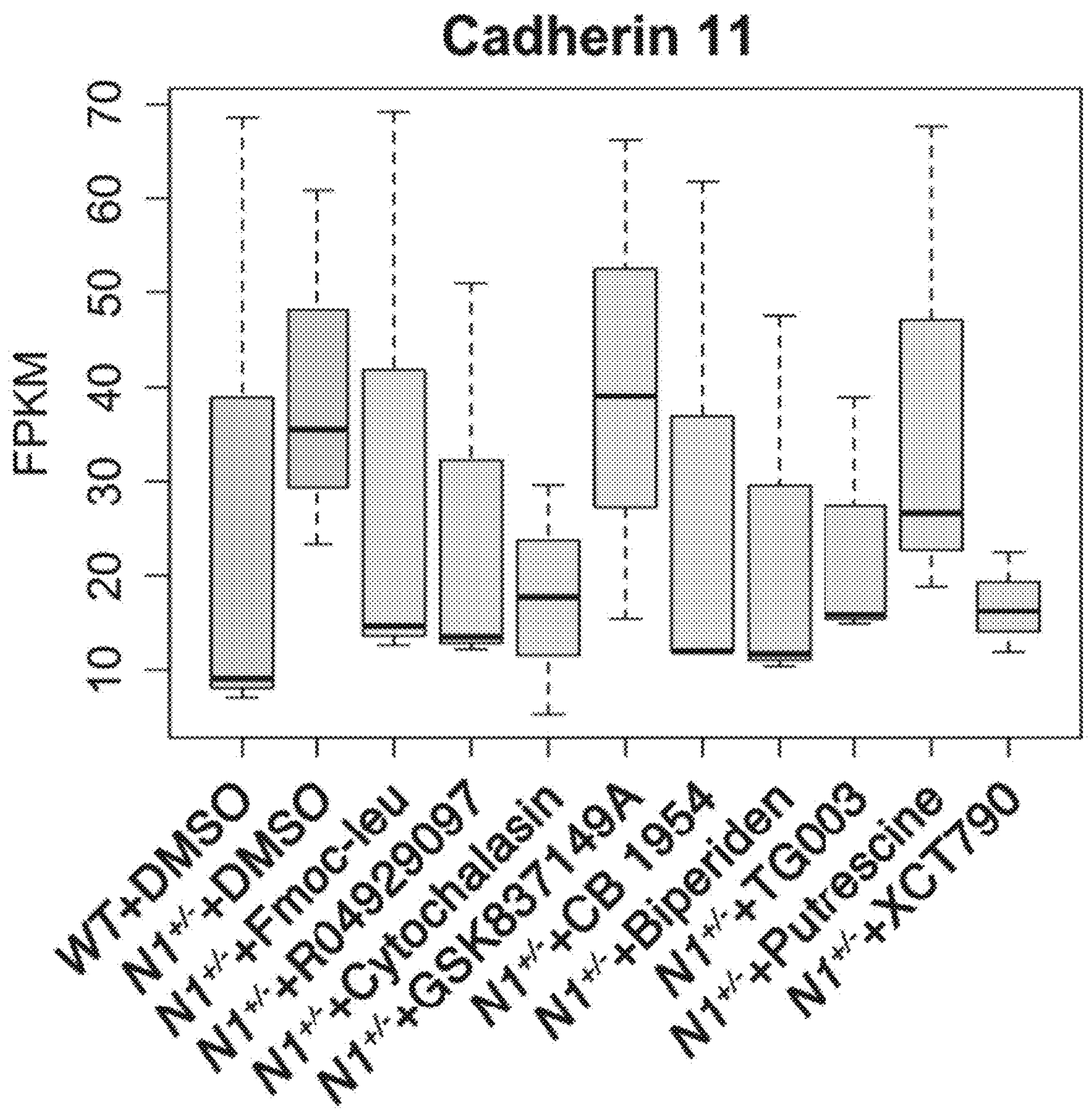
FIG. 9A depicts Cadherin 11 mRNA expression by whole transcriptome RNA-seq in $N1^{+/-}$ ECs treated with each network-correcting small molecule compared to $N1^{+/-}$ or WT ECs exposed to DMSO. Boxes represent the interquartile range, whiskers represent the range, and the solid horizontal line represents the median.
Figure 9B:
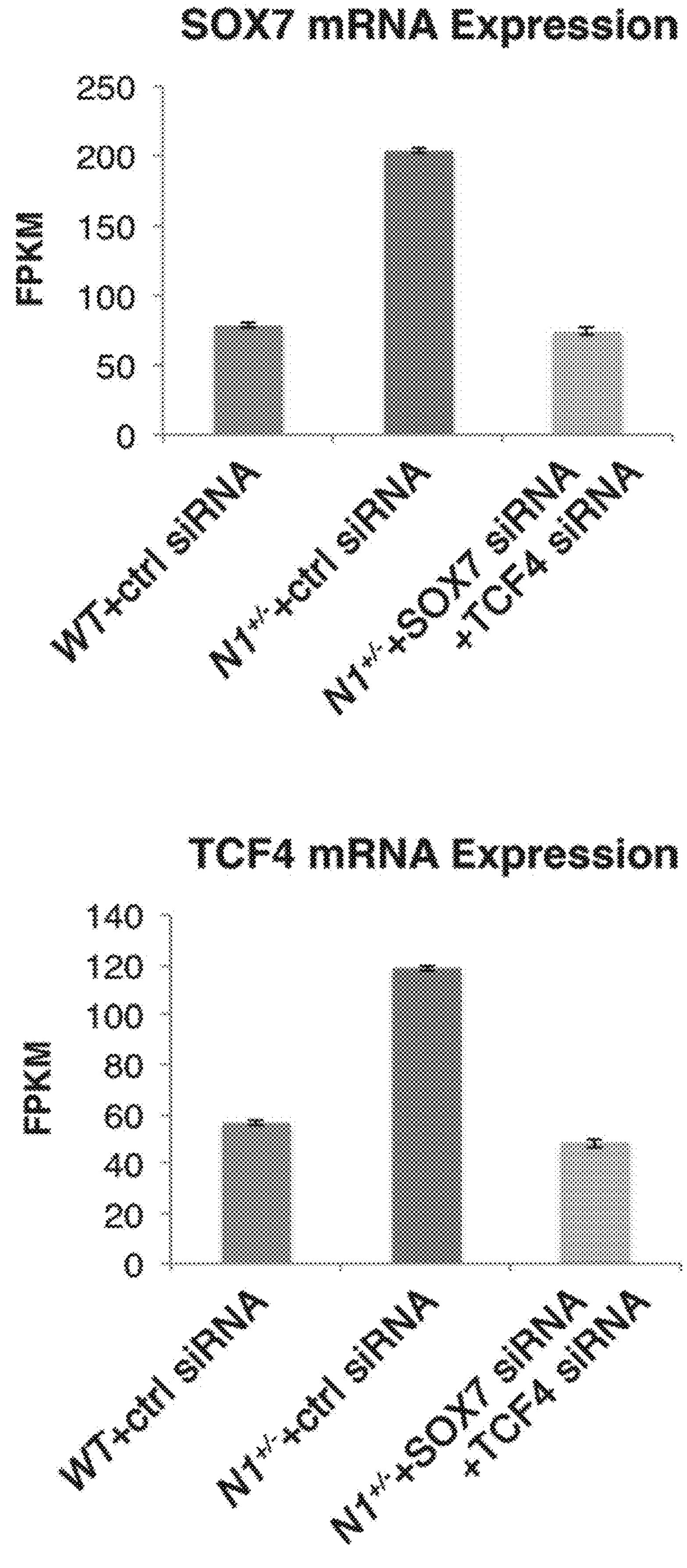
FIG. 9B depicts SOX7 or TCF4 mRNA expression by whole transcriptome RNA-seq in $N1^{+/-}$ ECs treated with siRNA targeting SOX7 and TCF4 compared to $N1^{+/-}$ or WT ECs treated with control siRNA. Error bars represent standard error.
Figure 9C:
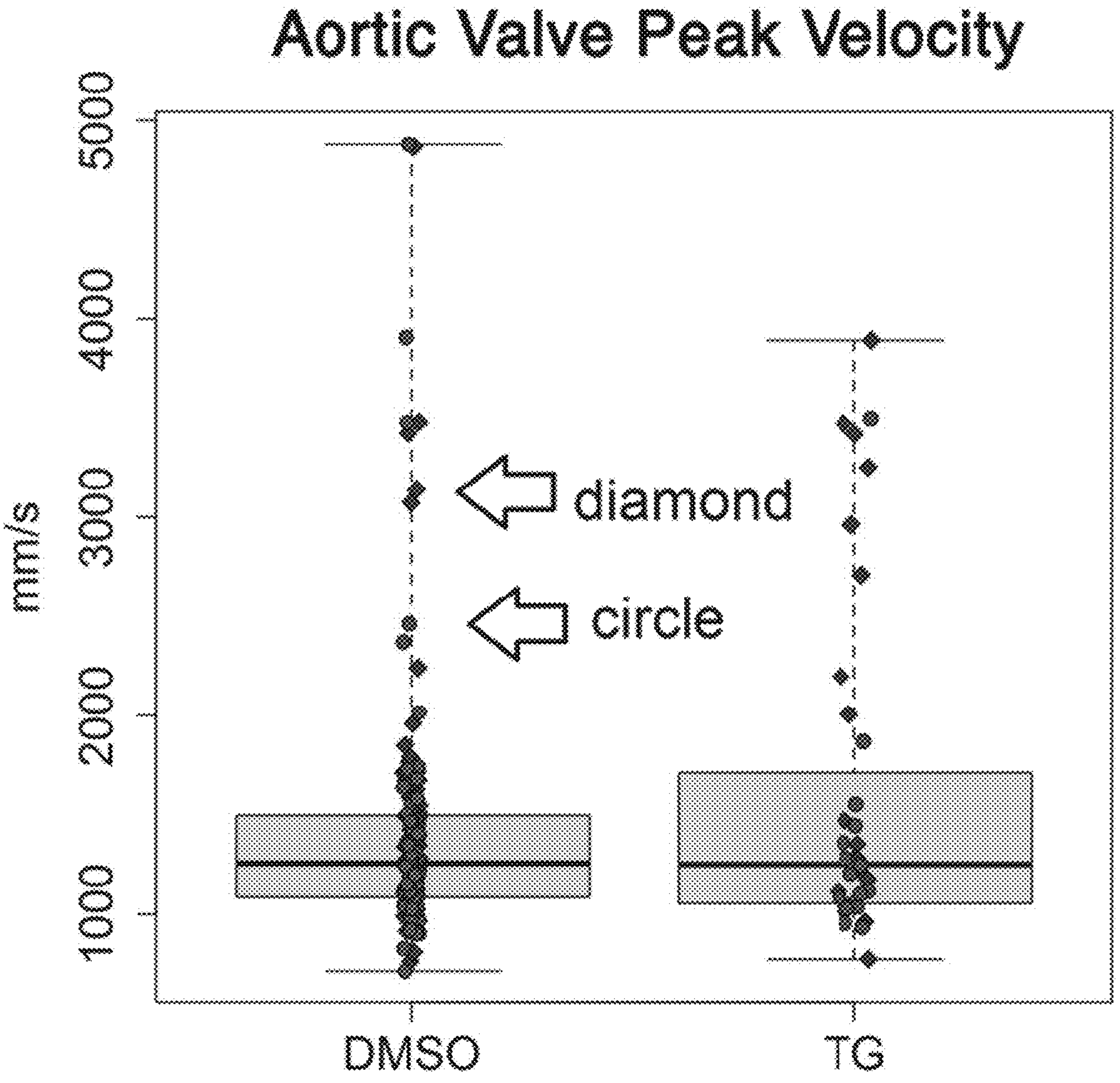
FIG. 9C depicts AV peak velocity by echocardiography in $N1^{+/-}/mTR^{G2}$ mice treated with TG003 (n=38) or DMSO (n=86) (p=0.22, one-sided t-test). Boxes represent the interquartile range, whiskers represent the range, and the solid horizontal line represents the median. Circular dots represent females and diamonds represent males.
Figure 9D:
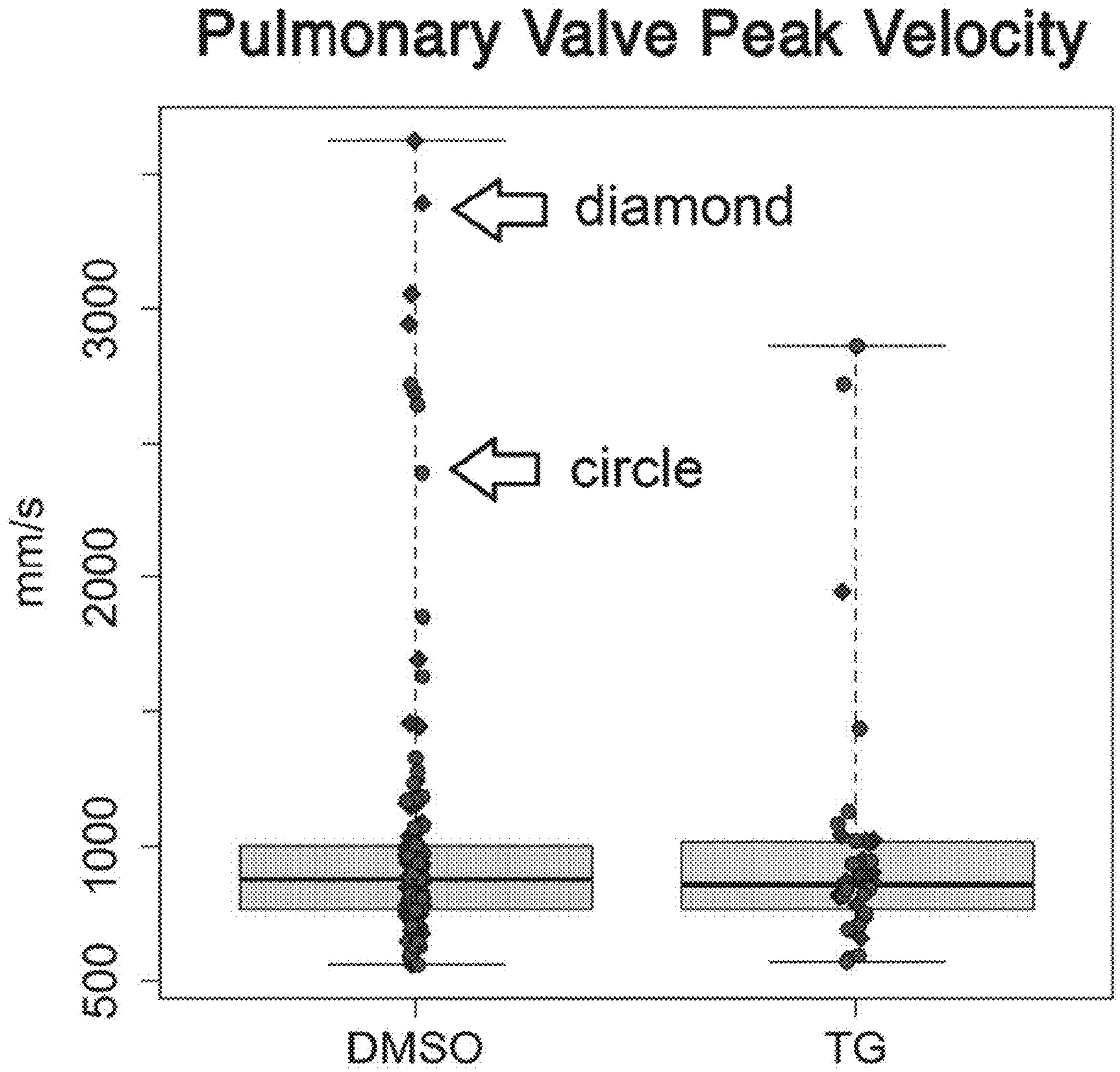
FIG. 9D depicts PV peak velocity by echocardiography in $N1^{+/-}/mTR^{G2}$ mice treated with TG003 (n=38) or DMSO (n=86) (p=0.83, one-sided t-test). Boxes represent the interquartile range, whiskers represent the range, and the solid horizontal line represents the median. Circular dots represent females and diamonds represent males.
Figure 9E:
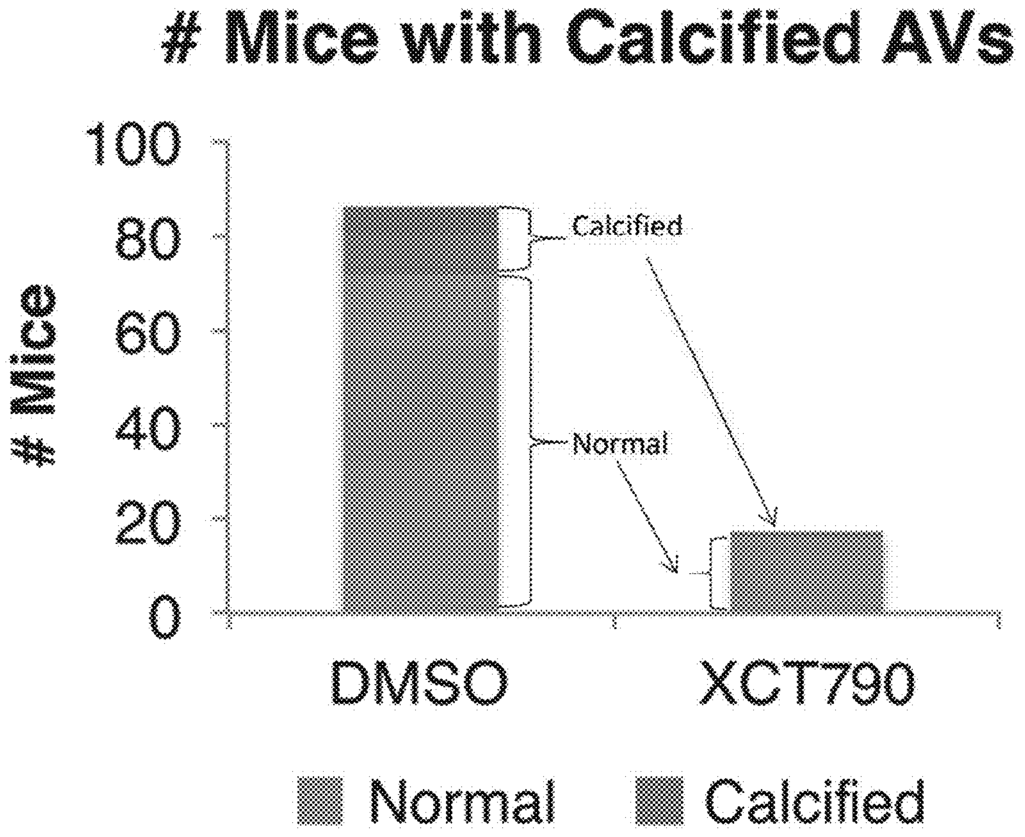
FIG. 9E depicts the number of $N1^{+/-}$/mTRG2 mice with calcified AVs by Alizarin red staining after treatment with XCT790 (1 of 17) or DMSO (14 of 86) (p=0.27, $X^2$ test).
Figure 9F:
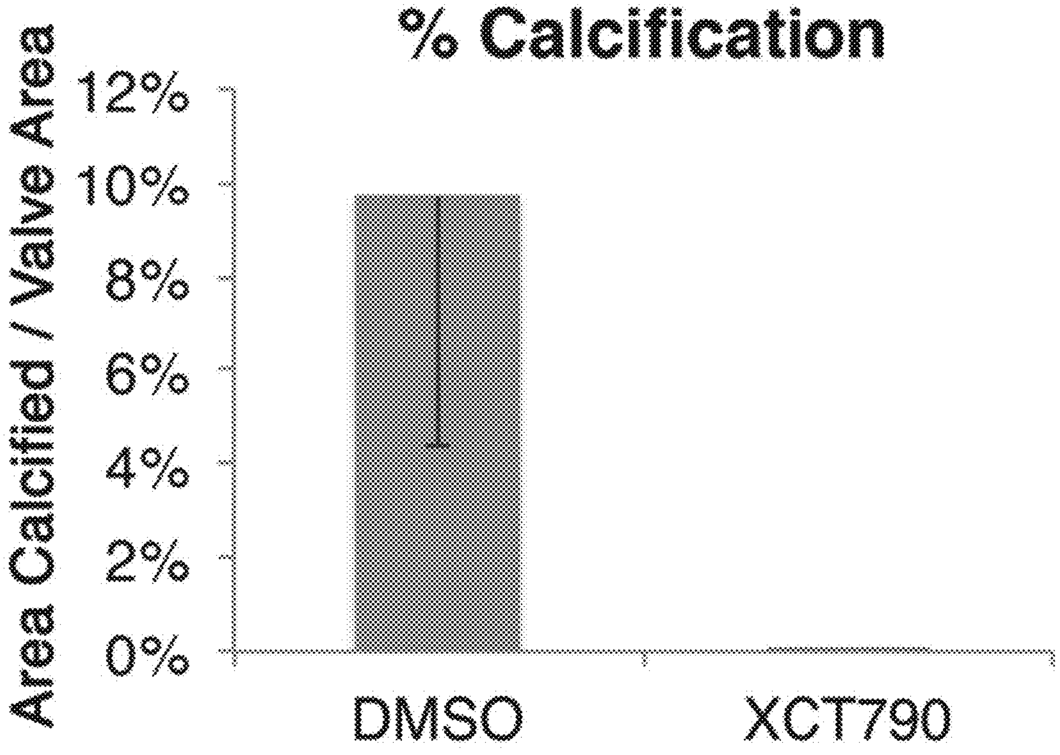
FIG. 9F depicts the percentage of the AV calcified by Alizarin red staining in $N1^{+/-}$/mTRG2 mice treated with XCT790 (n=1) or DMSO (n=14). Error bars represent standard error.
Figure 9G:
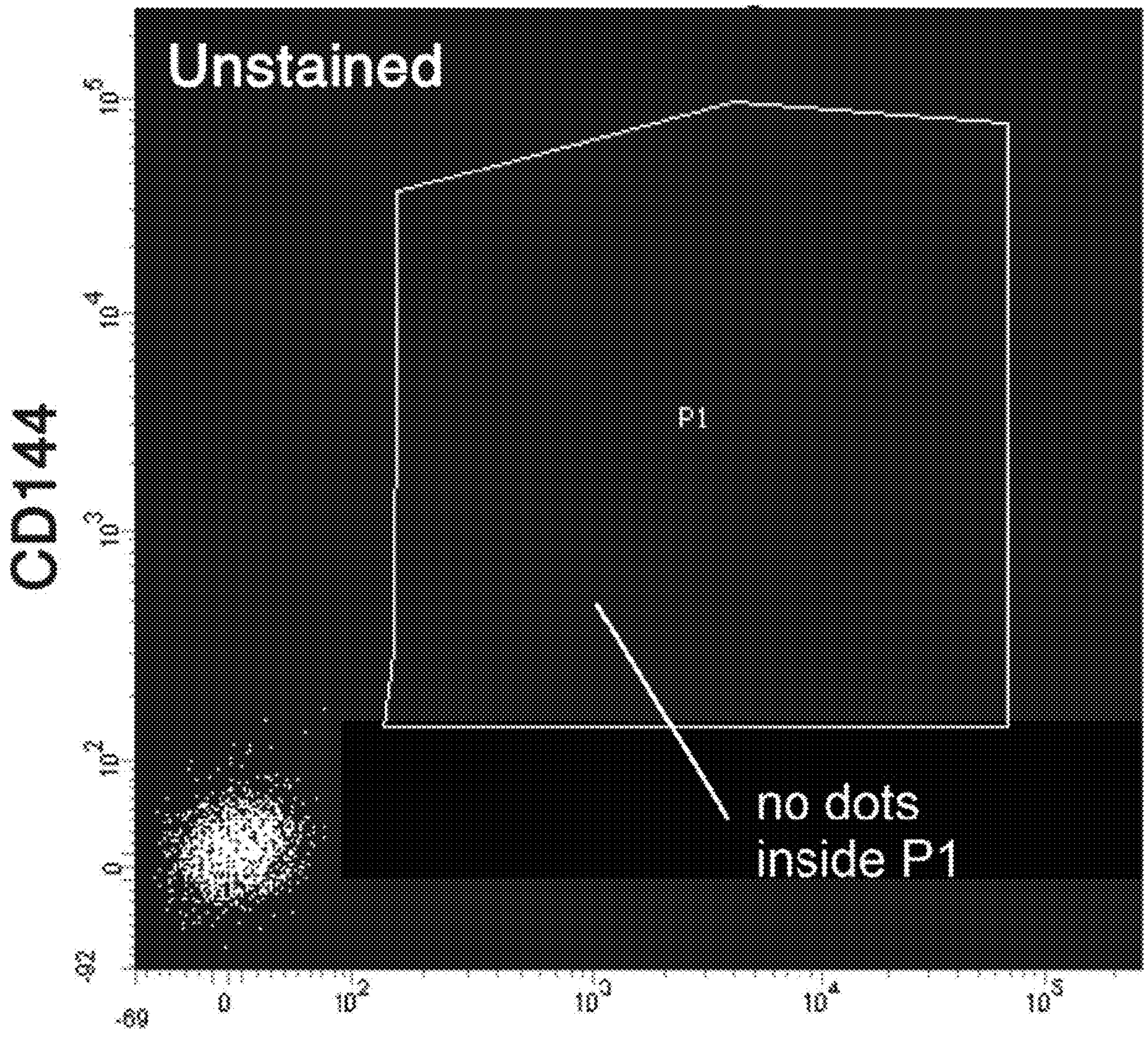
FIG. 9G depicts representative FACS analysis of unstained CD31/CD144 double positive iPSC-derived ECs on day 13 of differentiation.
Figure 9H:
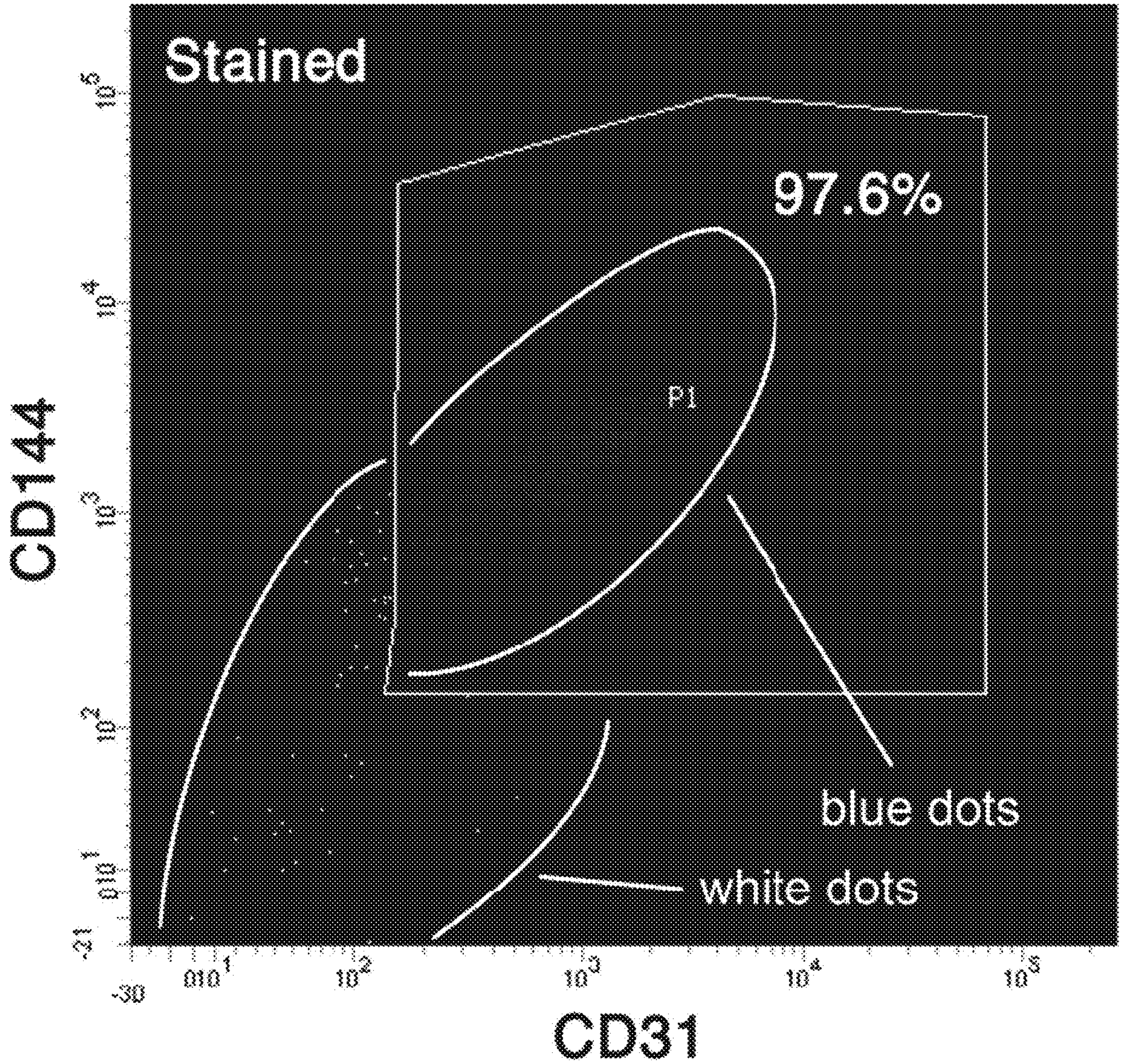
FIG. 9H depicts representative FACS analysis of stained CD31/CD144 double positive iPSC-derived ECs on day 13 of differentiation.
Figure 11A:
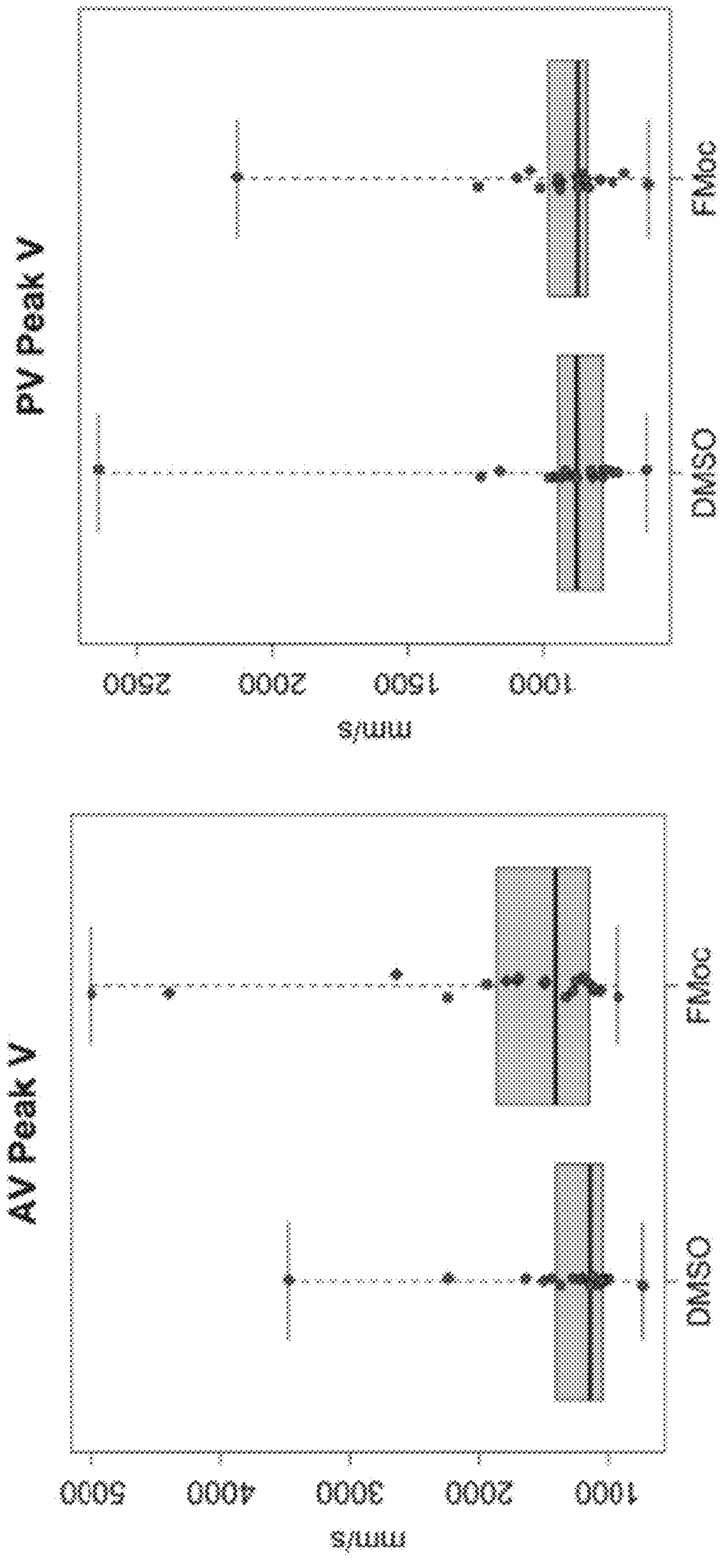
FIG. 11A depicts AV peak velocity and PV peak velocity by echocardiography in a small initial cohort of $N1^{+/-}/mTR^{G2}$ mice treated with Fmoc-leu or DMSO. Boxes represent the interquartile range, whiskers represent the range, and the solid horizontal line represents the median. Circular dots represent females and diamonds represent males.
Figure 11B:
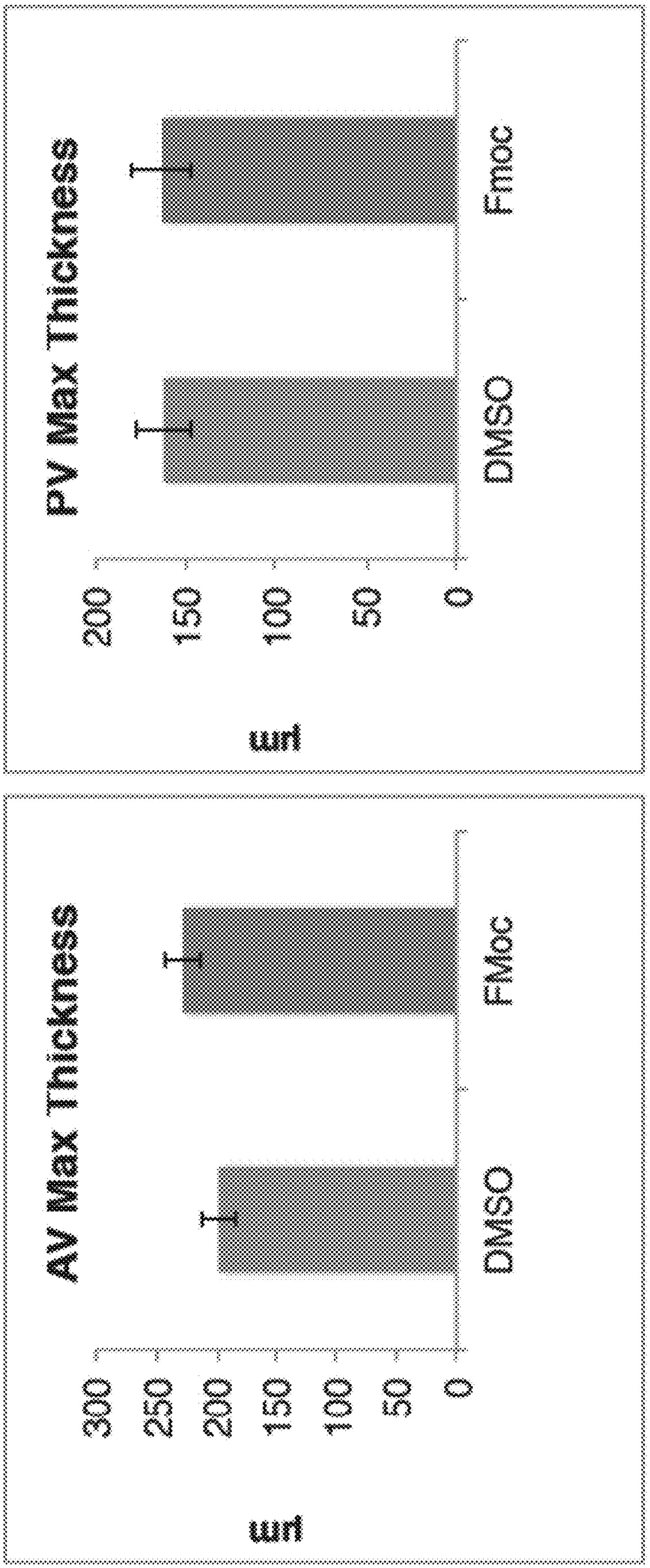
FIG. 11B depicts AV max thickness and PV max thickness in a small initial cohort of $N1^{+/-}/mTR^{G2}$ mice treated with Fmoc-leu or DMSO.
Figure 11C:
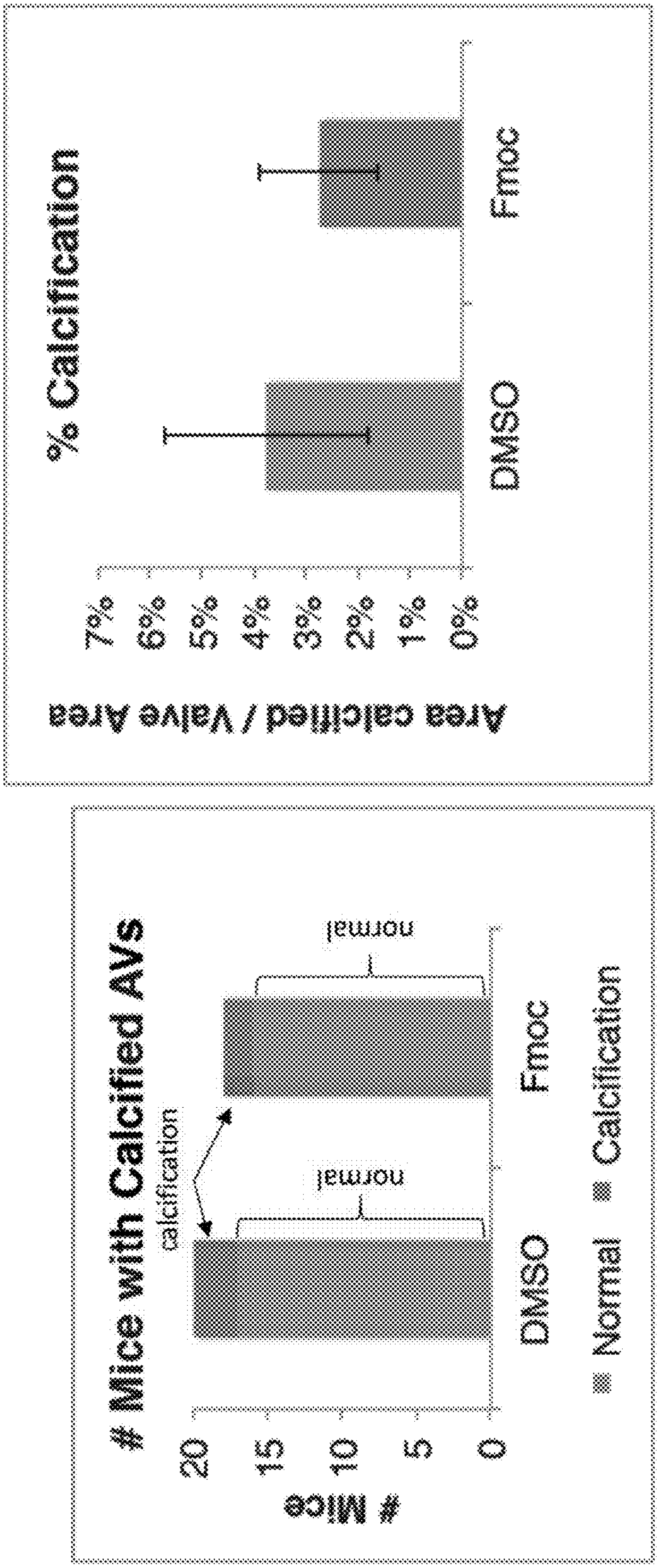
FIG. 11C (left/top) depicts the number of $N1^{+/-}/mTR^{G2}$ mice with calcified AVs by Alizarin red staining after treatment with Fmoc-leu or DMSO for a small initial cohort.
Figure 12A:
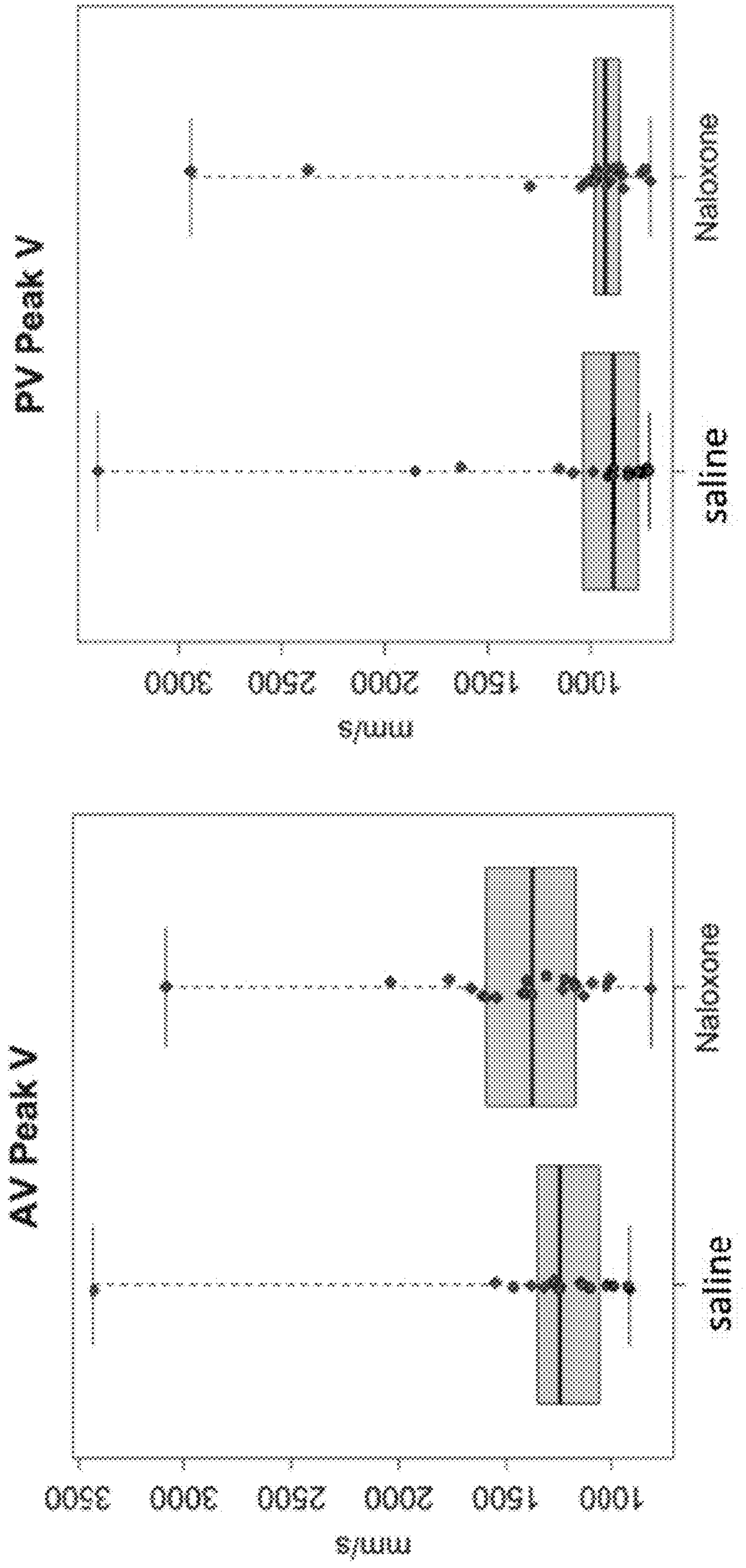
FIG. 12A depicts AV peak velocity and PV peak velocity by echocardiography in a small initial cohort of $N1^{+/-}/mTR^{G2}$ mice treated with naloxone or saline. Boxes represent the interquartile range, whiskers represent the range, and the solid horizontal line represents the median. Circular dots represent females and diamonds represent males.
Figure 12B:
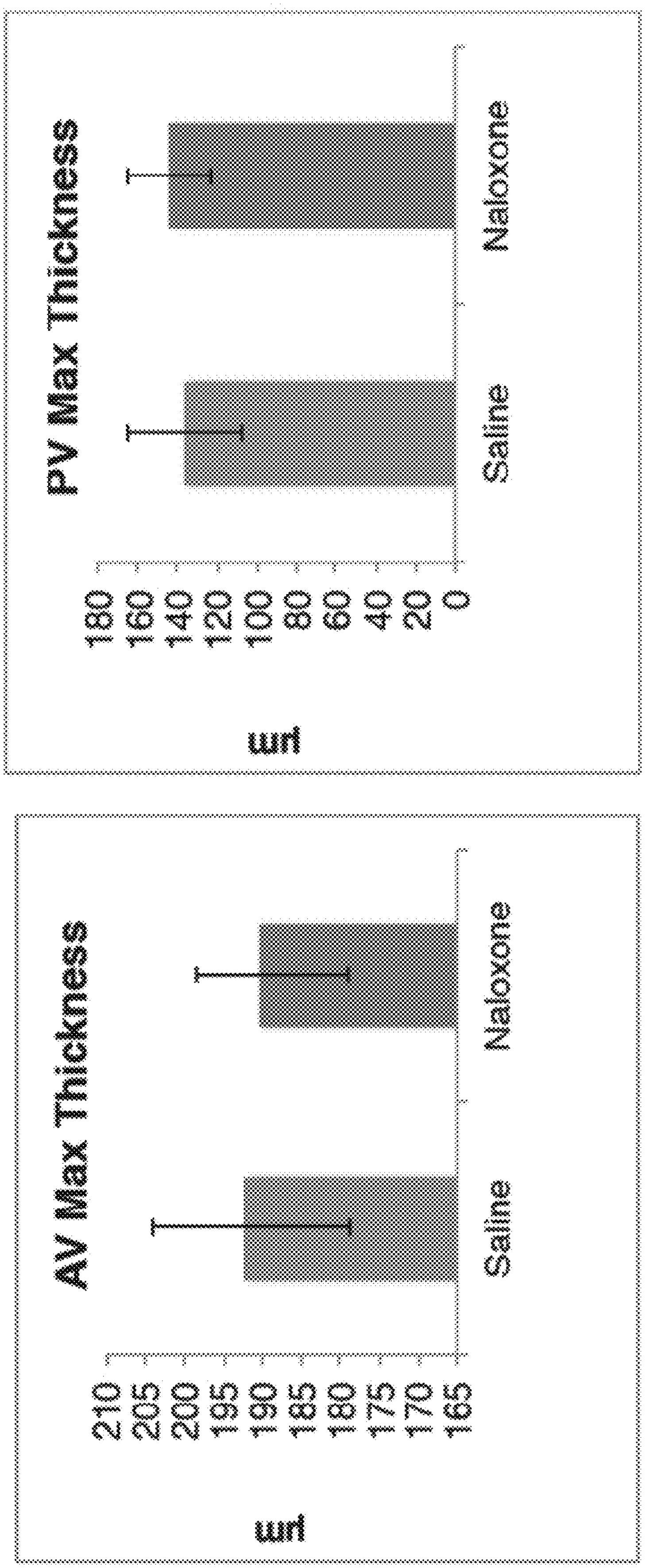
FIG. 12B depicts AV max thickness and PV max thickness in a small initial cohort of $N1^{+/-}/mTR^{G2}$ mice treated with naloxone or saline.
Figure 12C:
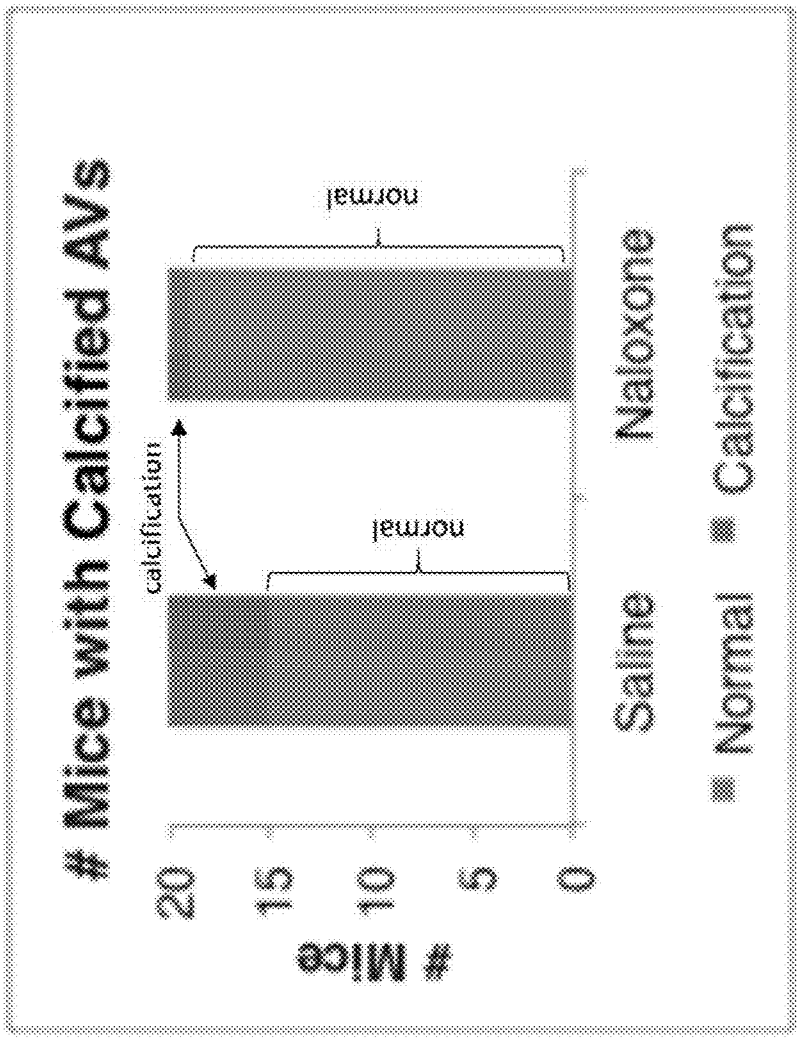
FIG. 12C depicts the number of $N1^{+/-}/mTR^{G2}$ mice with calcified AVs by Alizarin red staining after treatment with naloxone or saline for a small initial cohort.
Figure 13:
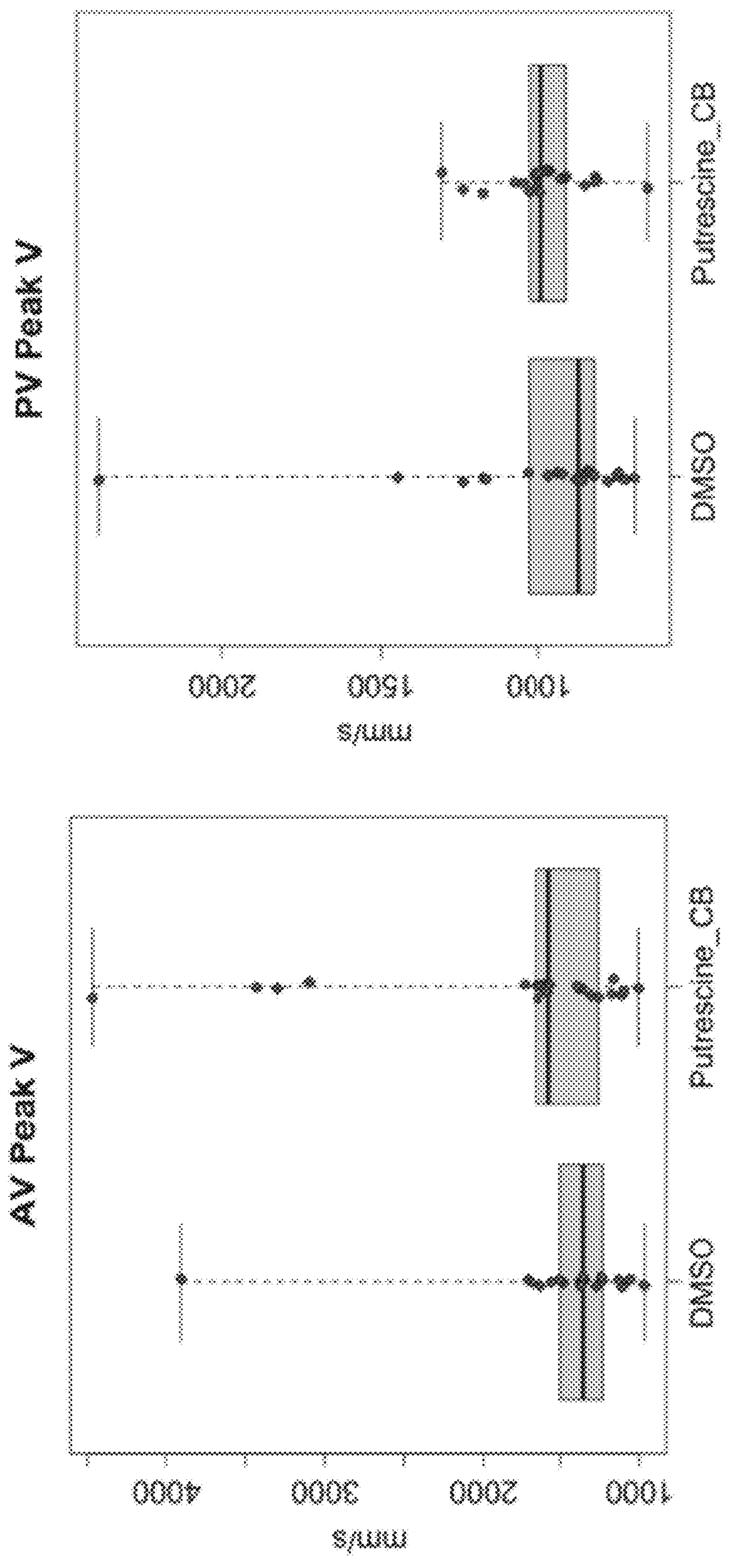
FIG. 13 depicts AV peak velocity and PV peak velocity by echocardiography in a small initial cohort of $N1^{+/-}/mTR^{G2}$ mice treated with putrescine+CB1954 or DMSO. Boxes represent the interquartile range, whiskers represent the range, and the solid horizontal line represents the median. Circular dots represent females and diamonds represent males.
Figure 14:
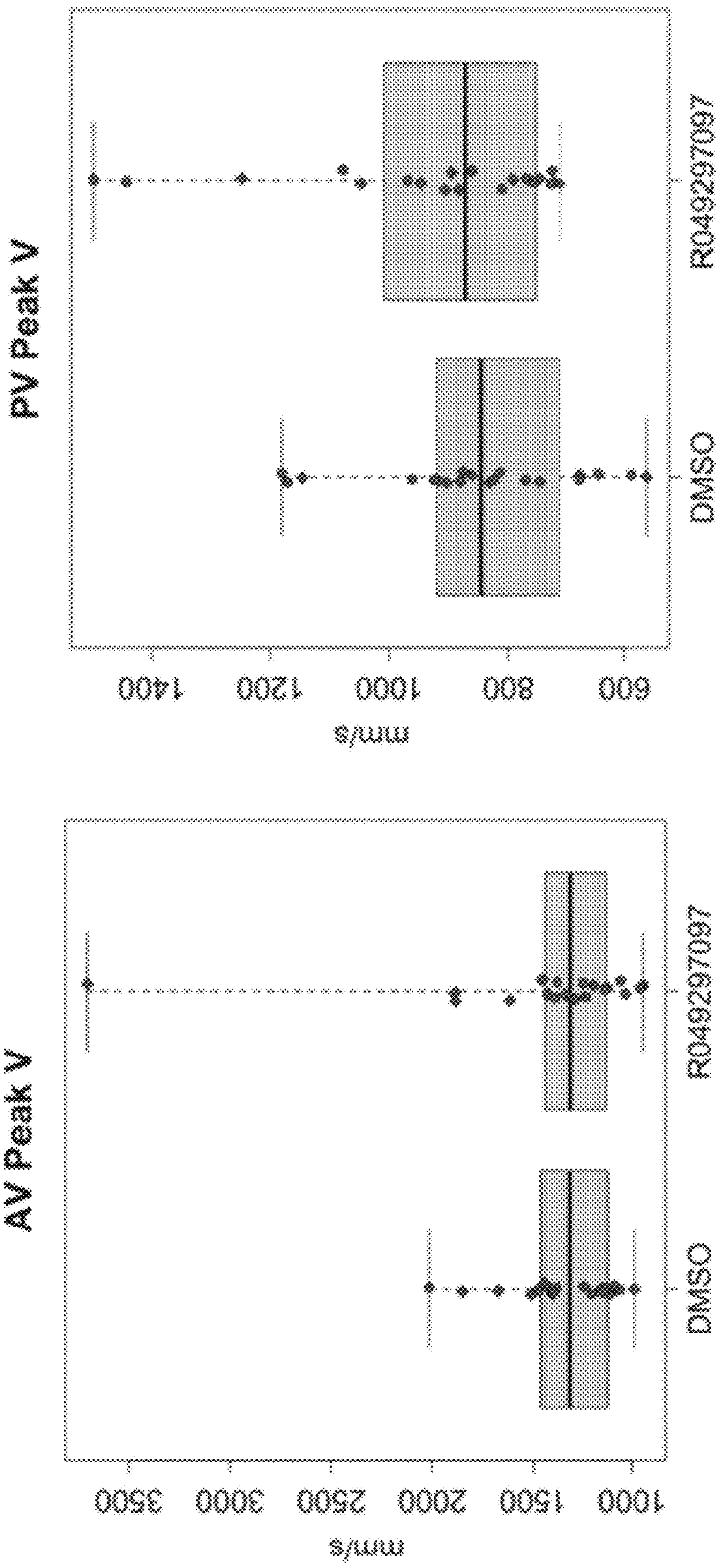
FIG. 14 depicts AV peak velocity and PV peak velocity by echocardiography in a small initial cohort of $N1^{+/-}/mTR^{G2}$ mice treated with RO4929097 or DMSO. Boxes represent the interquartile range, whiskers represent the range, and the solid horizontal line represents the median. Circular dots represent females and diamonds represent males.
Figure 15A:
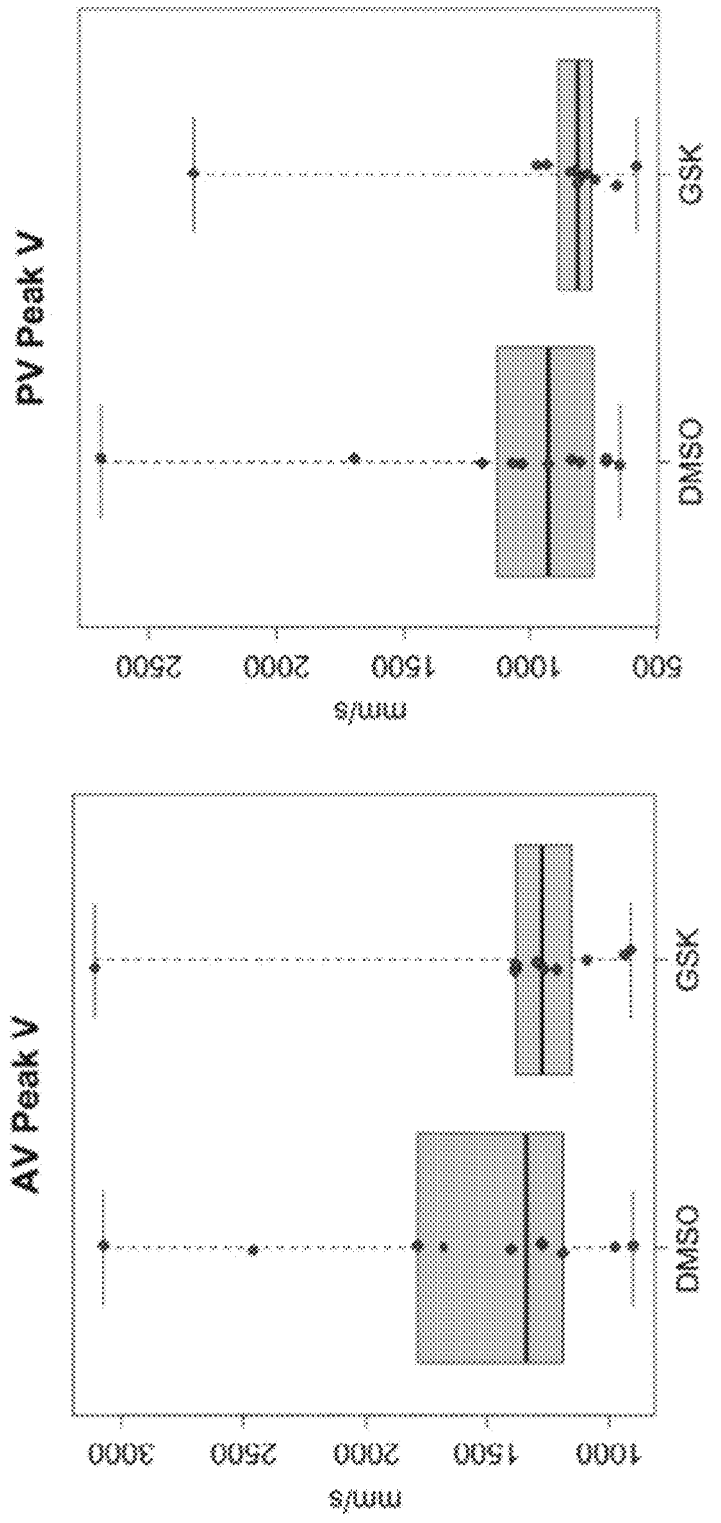
FIGS. 15A and 15B depict AV peak velocity and PV peak velocity by echocardiography in a small initial cohort of $N1^{+/-}/mTR^{G2}$ mice treated with GSK837149A or DMSO. Boxes represent the interquartile range, whiskers represent the range, and the solid horizontal line represents the median. Circular dots represent females and diamonds represent males.
Figure 15B:
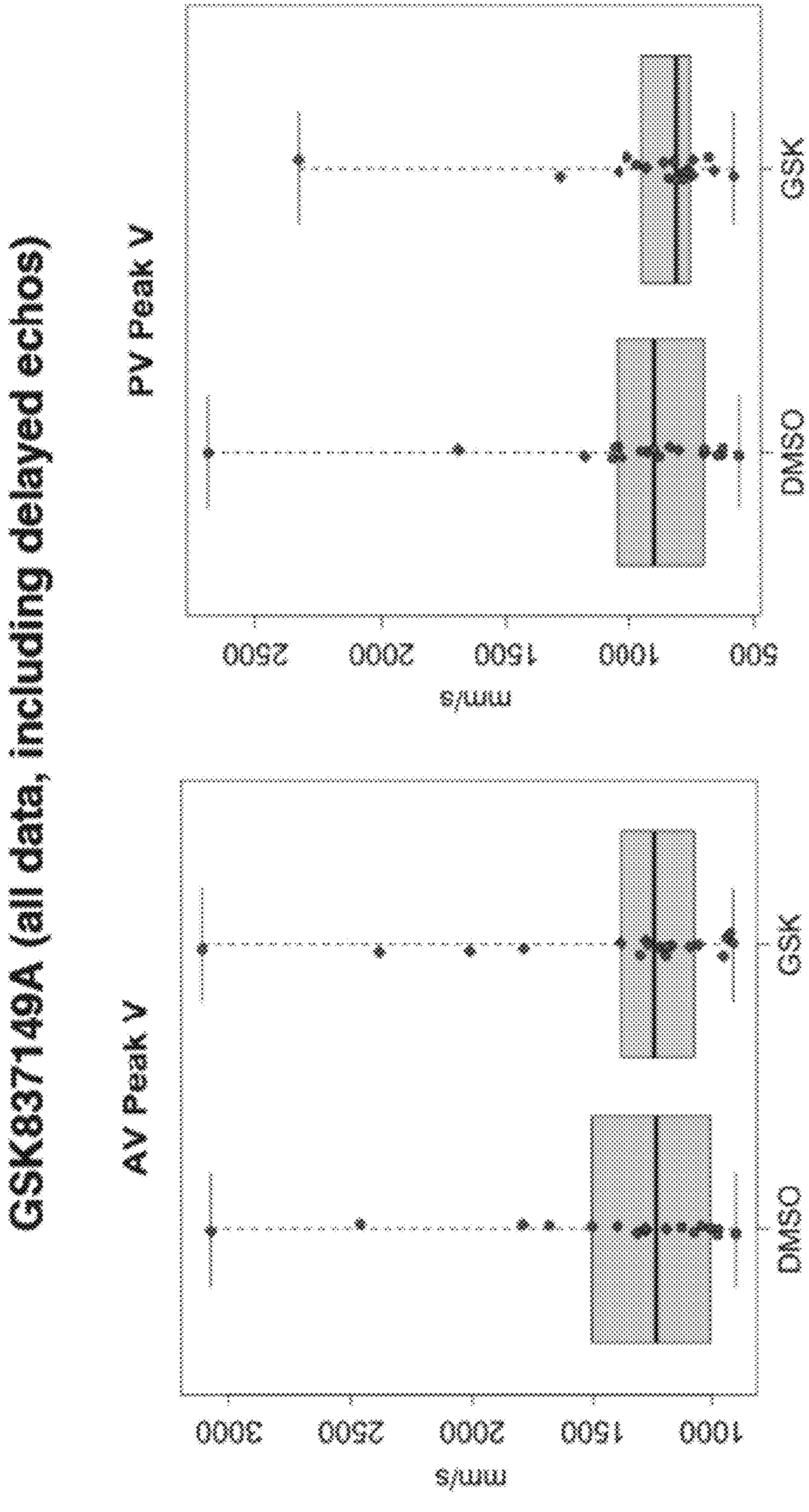

TALEN-engineered isogenic human iPSCs that were either WT (wild-type) or $N1^{+/-}$ were derived and characterized as detailed in Theodoris et al., *Cell.* 2015; 160:1072-1086. Isogenic iPSCs (induced pluripotent stem cells) were differentiated into ECs as previously described (Theodoris et al., 2015; White et al., *Stem Cells.* 2012; 31:92-103). On day 13 of the differentiation process, ECs were greater than 90% double-positive for CD31 (BD #558068) and CD144 (#FAB9381P) by FACS (fluorescence-activated cell sorting) analysis (FIGS. 9G-H). Small molecule experiments (described below) were conducted at day 15 of differentiation.

Small Molecule Screen and Validation

Starting on day 15 of differentiation, WT ECs were exposed to 10 μM DMSO (dimethyl sulfoxide) (n=80) while isogenic $N1^{+/-}$ ECs were exposed to either 10 μM DMSO (n=80) or one of the small molecules from the LOPAC (1280 molecules) (Sigma LO1280) or Sheng Ding (315 molecules) chemical libraries. DMSO or small molecules were renewed with EC media (ScienCell #1001) changes on alternating days until the cells were ultimately collected for analysis on day 21. ECs were imaged using the IN Cell Analyzer on day 21 to evaluate morphology and cell death; wells with extensive cell death were eliminated from final analyses. For validation experiments, promising small molecules identified from the initial screen were applied to $N1^{+/-}$ ECs in duplicate or triplicate along with controls of DMSO-exposed WT and $N1^{+/-}$ ECs (n=4 each) using the same process as the initial screen described above.

Targeted RNA-Seq and Analysis Pipeline

ECs were lysed and RNA was isolated using the Qiagen RNeasy 96-well purification kit. RNA was diluted so that it was between the 10 pg-1 ng range accepted by the Cellular Research Precise targeted RNA-seq (RNA sequencing) system. Targeted RNA-seq libraries were prepared as per the Cellular Research Precise protocol (Rev 03092015), which includes both molecule and sample barcoding. The selected 119 target genes (see Table 1) included 3 low-expressing housekeeping genes for normalization (CHMP2A, C1orf43, REEP5) and either predicted central regulatory nodes or peripheral genes positioned within varied regions of the N1 network to permit identification of small molecules that affected central nodes as well as those that may have a synergistic effect in combination due to regulating different aspects of the network. Briefly, RNA was added to the Precise Encoding Plate containing indexed dT primer, dNTPs, and Spike-in mRNA controls and incubated at 65° C. for 3 minutes followed by cooling on ice. A master-mix of RT enzyme, RNase inhibitor, and buffer was then added to the samples, and they were incubated at 42° C. for 30 minutes followed by 80° C. for 5 minutes. Each plate of samples was combined into a single 2 ml tube and purified with AMPureXP beads. N1 PCR master-mix was added and samples were incubated for 94° C. for 2 minutes, followed by 15 cycles of 94° C. for 30 seconds, 55° C. for 3 minutes, and 68° C. for 1 minute, followed by 68° C. for 7 minutes. Samples were purified with AMPureXP beads and N2 PCR master-mix was added. Samples were incubated with the same thermal cycler program as above for 12 cycles. These final libraries were then purified with AMPureXP beads and analyzed for quality and concentration by Agilent Bioanalyzer and Illumina Library Quantification Kit (KAPA Biosystems), respectively. Libraries were normalized to equivalent concentration and pooled for paired-end 100 bp sequencing on an Illumina HiSeq 2500 instrument.

Sequencing data was analyzed using Cellular Research Precise Analysis Pipeline on the SevenBridges platform, which included analyzing sequencing quality with FASTQC, trimming adapters and filtering reads, demultiplexing based on sample barcodes, aligning reads with Bowtie 2, and determining the number of unique molecular indices per gene. Network inference was based on mutual information of gene expression from all DMSO- and small molecule-exposed samples as described in Margolin et al., *BMC Bioinformatics.* 2006; 7 Suppl 1:S7. Network diagram was generated using NetworkX (Hagberg et al., Exploring Network Structure, Dynamics, and Function using NetworkX. SciPy. 2008) based on network connections inferred from the small molecule screen data as described above with colors based on whole transcriptome RNA-seq gene expression of isogenic $N1^{+/-}$ compared to WT ECs.

Example 1

Map of Gene Network Dysregulated by N1 Haploinsufficiency

Results

To map the network disrupted by N1 haploinsufficiency and identify small molecules that correct the network back to the normal state, targeted RNA-seq of 119 genes was performed in isogenic wild-type (WT) or $N1^{+/-}$ iPSC-derived ECs exposed to either DMSO or one of 1595 small molecules. The selected 119 target genes were either predicted central regulatory nodes or peripheral genes positioned within varied regions of the N1 network to facilitate identification of small molecules that affected central nodes as well as those that may have a synergistic effect in combination due to regulating different aspects of the network.

Figure 4A:
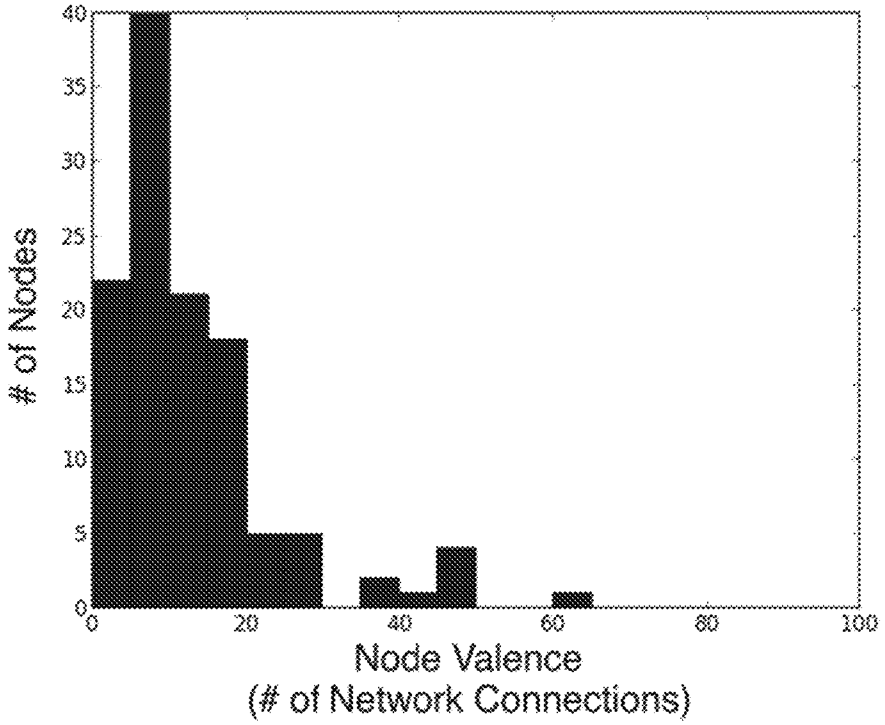
FIG. 4A depicts a histogram of the number of network connections of each node within the N1-dependent gene network as mapped by network inference based on targeted RNA-seq data.
Figure 4B:
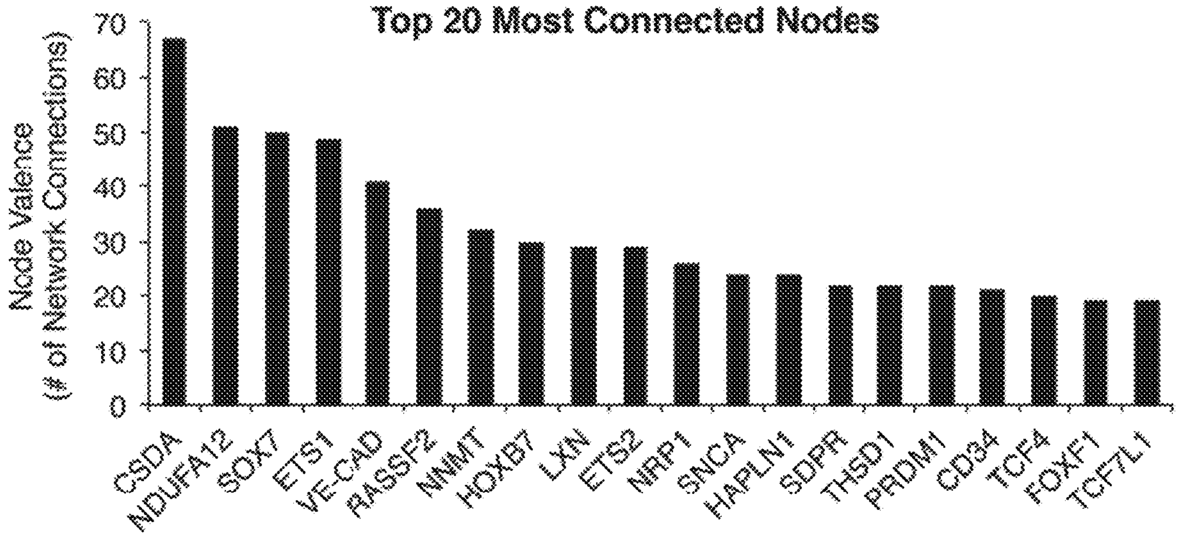
FIG. 4B depicts the top 20 most connected nodes in the N1-dependent gene network ordered from greatest to least valent.
Figure 5A:
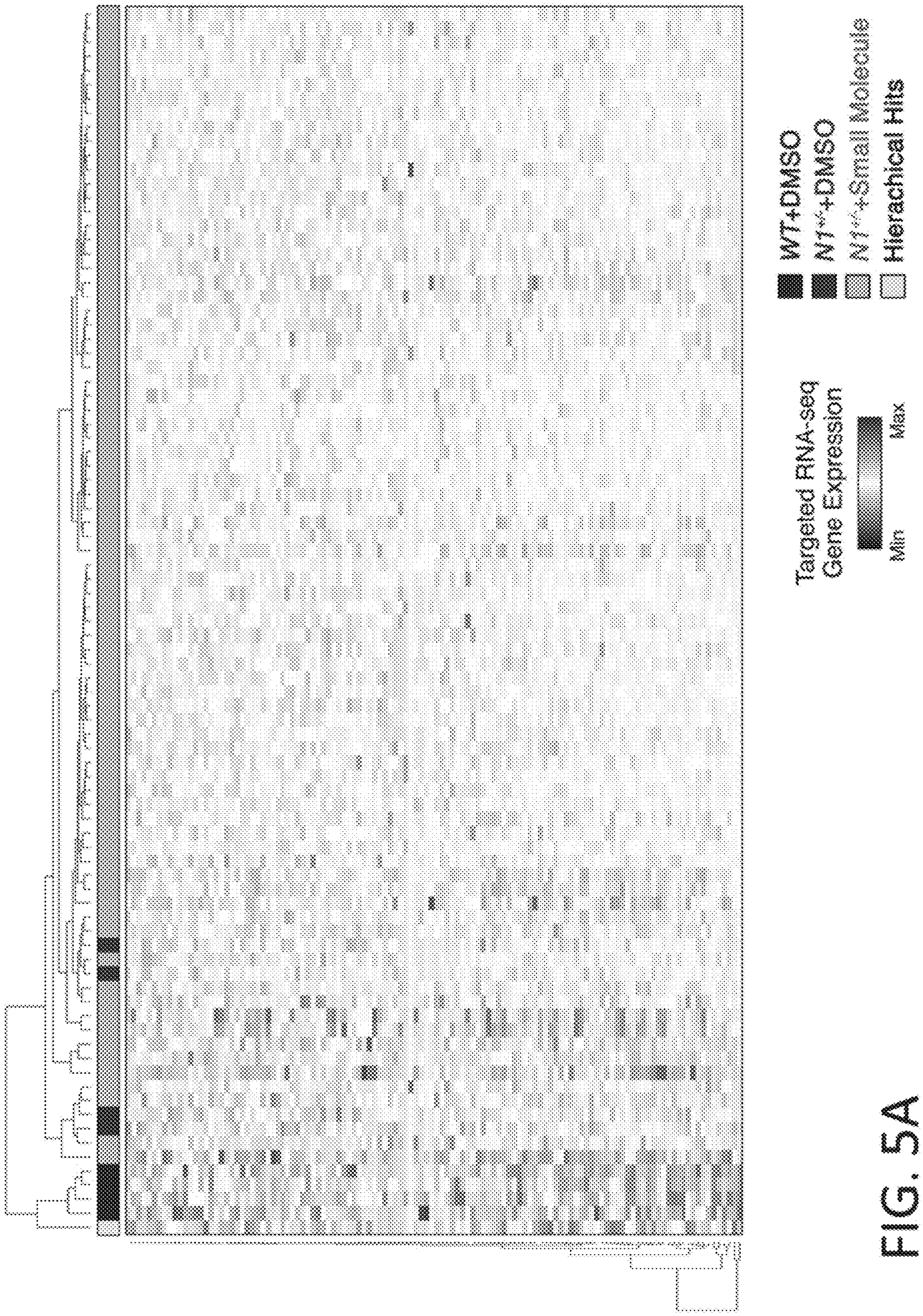
FIG. 5A depicts a hierarchical clustering of transcriptional profiles of $N1^{+/-}$ ECs treated with each of the small molecules (from LOPAC library plate 1 of 16) compared to $N1^{+/-}$ or WT ECs exposed to DMSO.
Figure 5B:
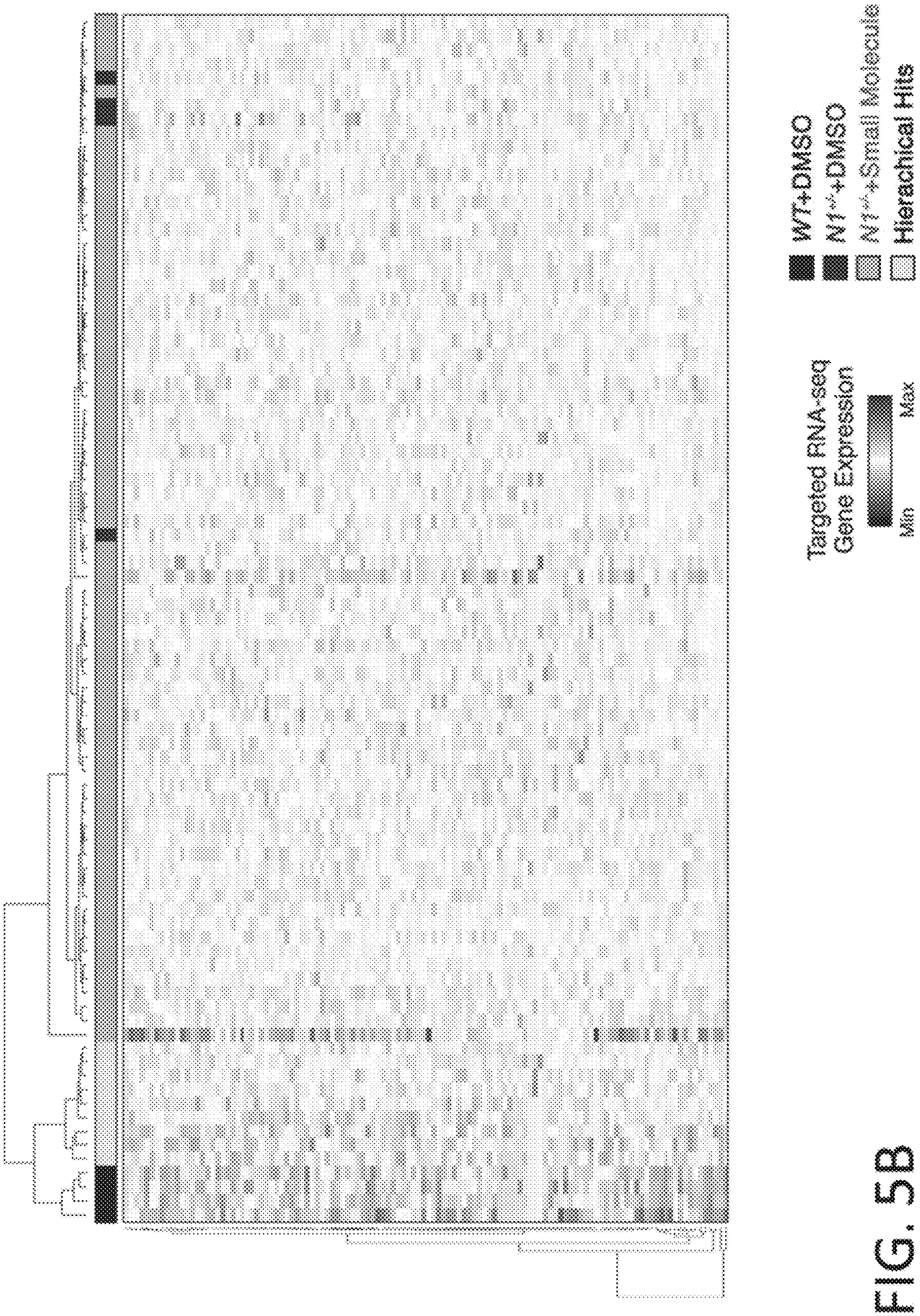
FIG. 5B depicts a hierarchical clustering of transcriptional profiles of $N1^{+/-}$ ECs treated with each of the small molecules (from LOPAC library plate 4 of 16) compared to $N1^{+/-}$ or WT ECs exposed to DMSO.
Figure 6A:
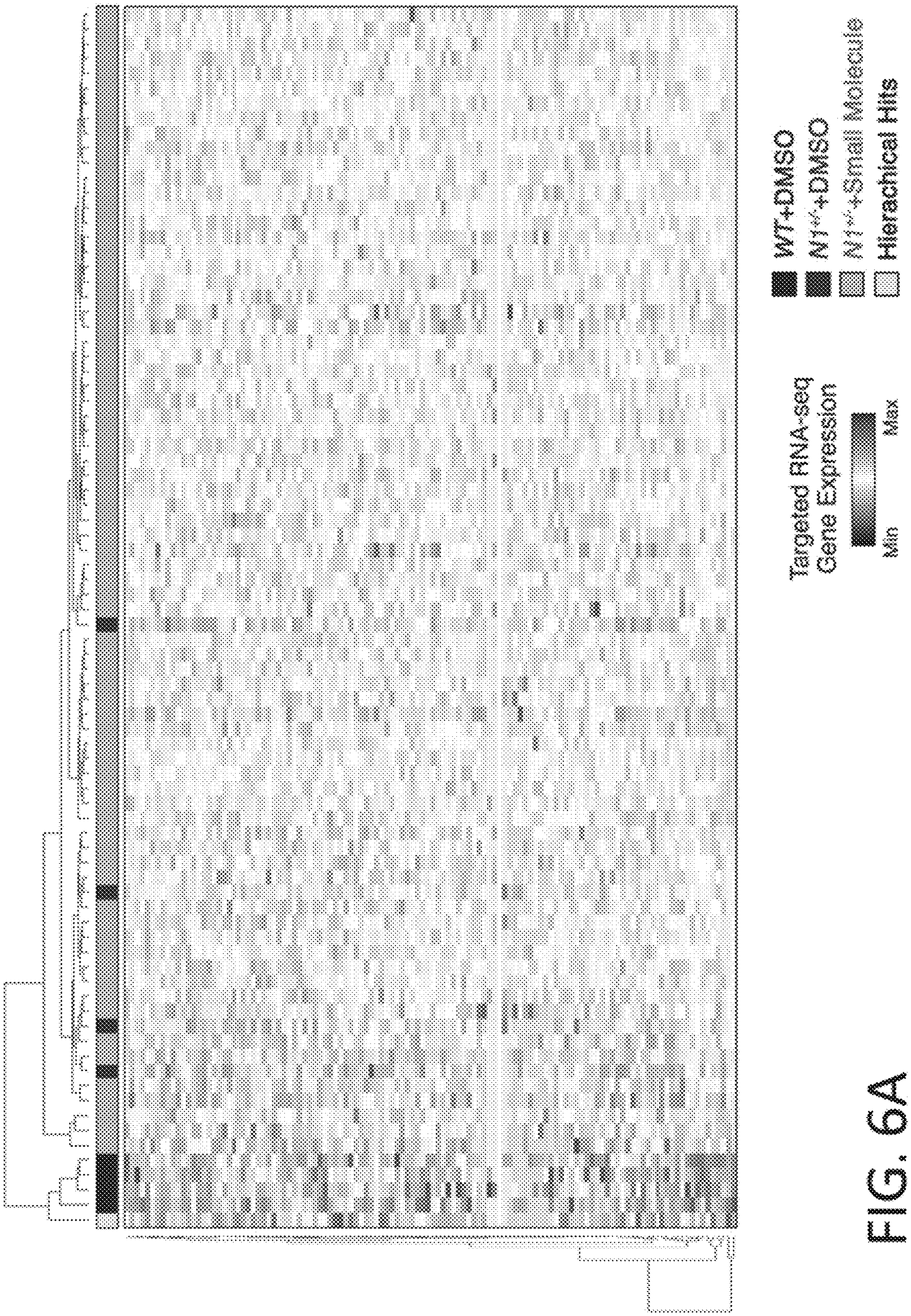
FIG. 6A depicts a hierarchical clustering of transcriptional profiles of $N1^{+/-}$ ECs treated with each of the small molecules (from LOPAC library plate 7 of 16) compared to $N1^{+/-}$ or WT ECs exposed to DMSO.
Figure 6B:
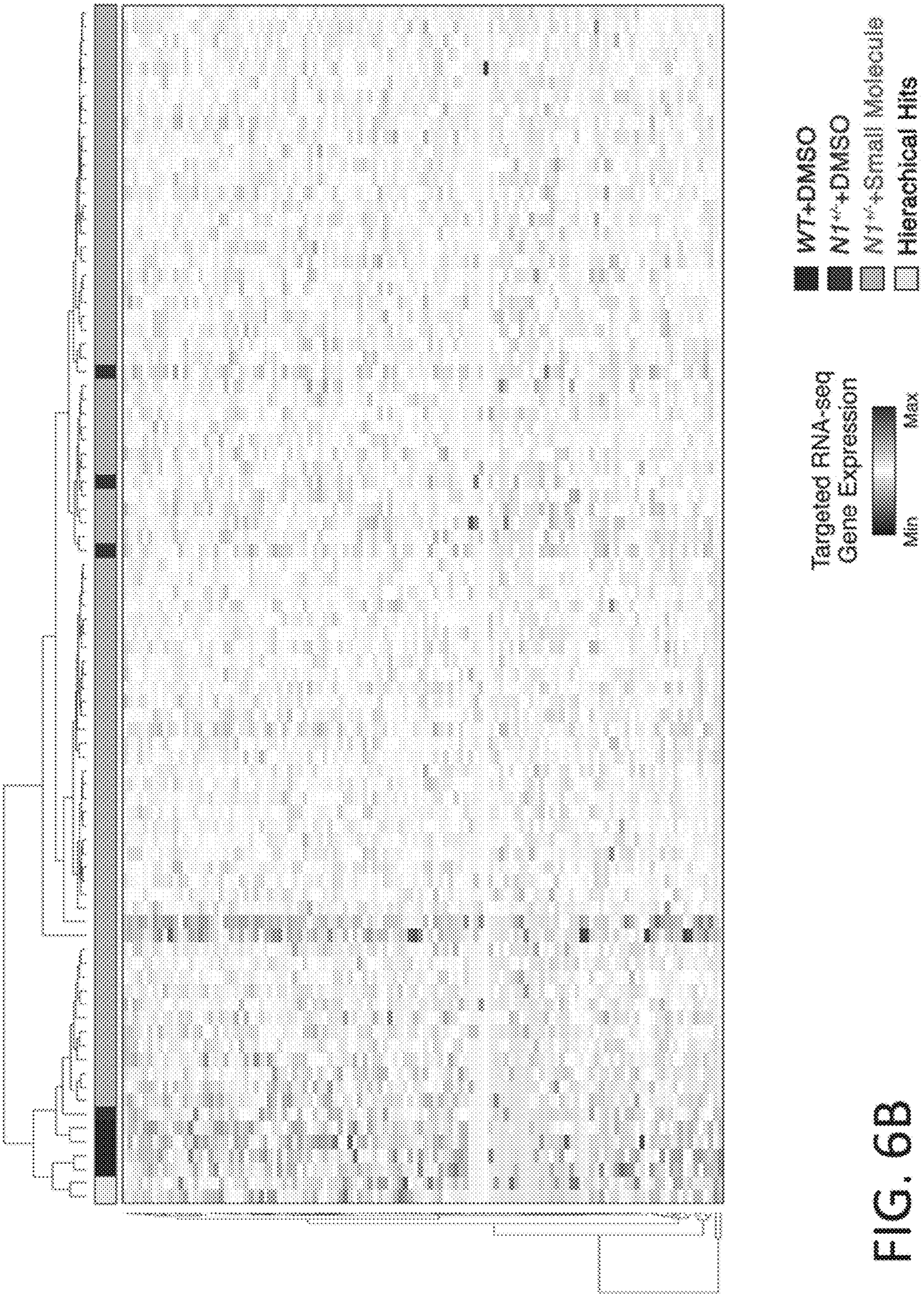
FIG. 6B depicts a hierarchical clustering of transcriptional profiles of $N1^{+/-}$ ECs treated with each of the small molecules (from LOPAC library plate 8 of 16) compared to $N1^{+/-}$ or WT ECs exposed to DMSO.
Figure 7A:
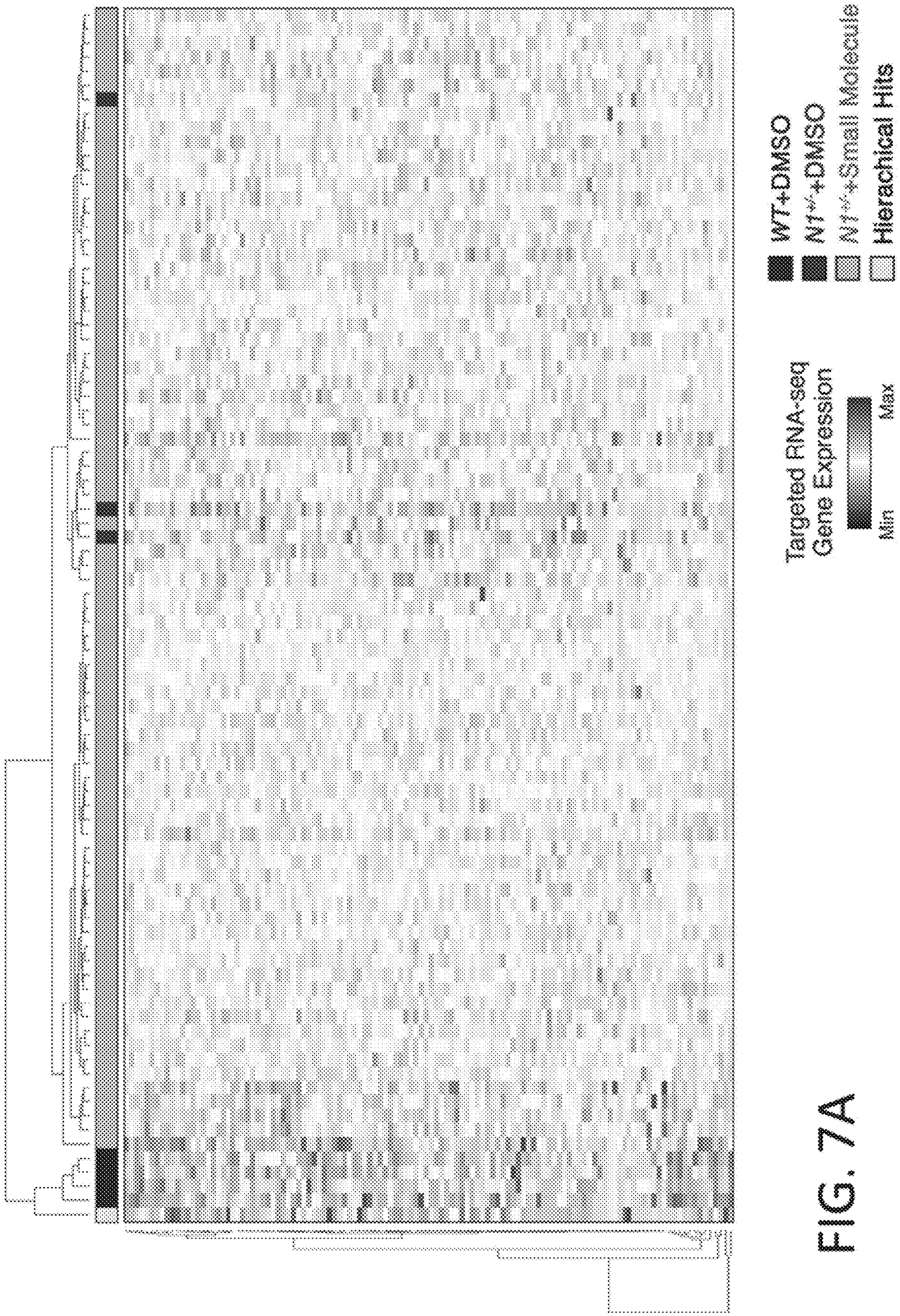
FIG. 7A depicts a hierarchical clustering of transcriptional profiles of $N1^{+/-}$ ECs treated with each of the small molecules (from LOPAC library plate 12 of 16) compared to $N1^{+/-}$ or WT ECs exposed to DMSO.
Figure 7B:
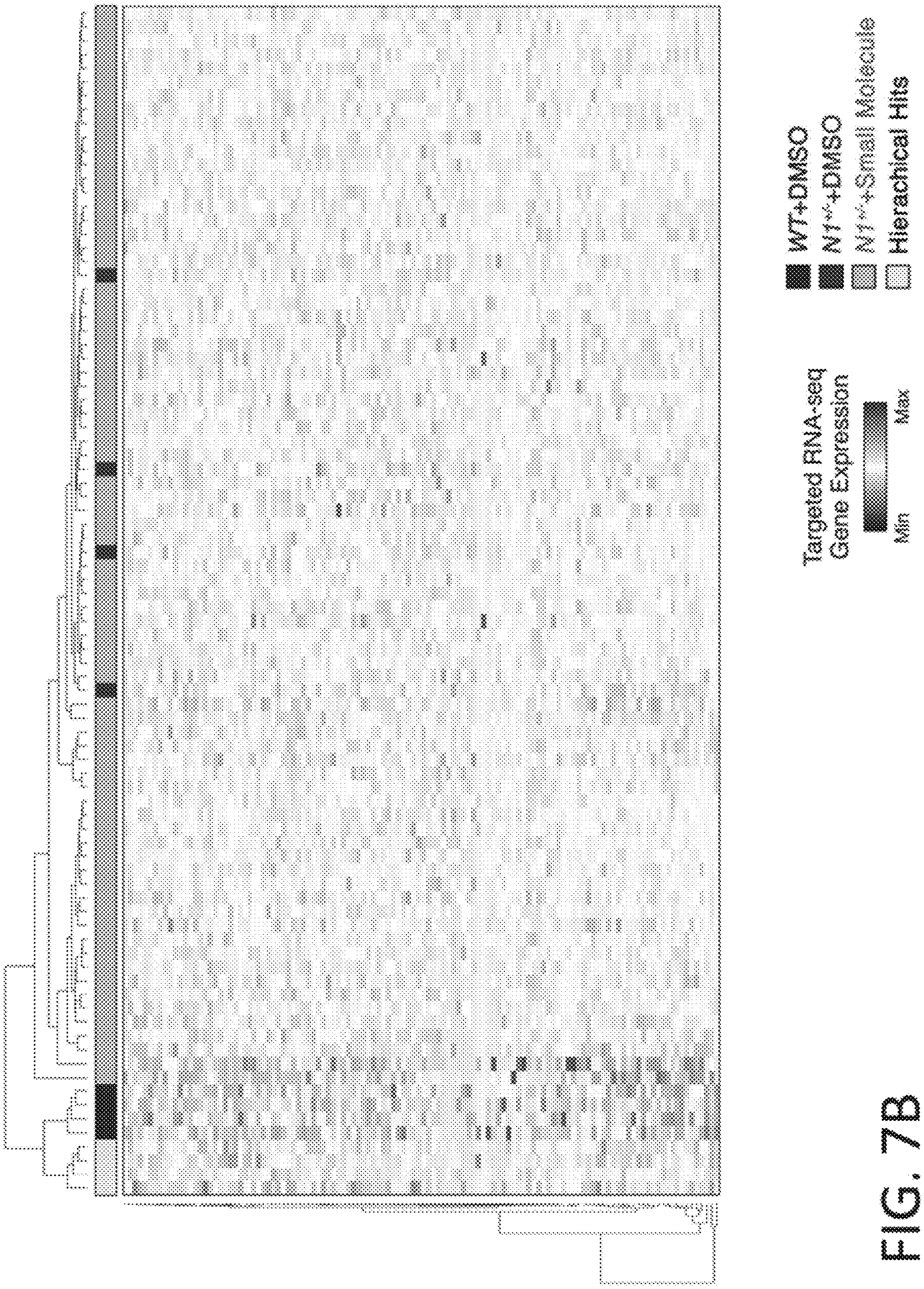
FIG. 7B depicts a hierarchical clustering of transcriptional profiles of $N1^{+/-}$ ECs treated with each of the small molecules (from LOPAC library plate 13 of 16) compared to $N1^{+/-}$ or WT ECs exposed to DMSO.
Figure 8A:
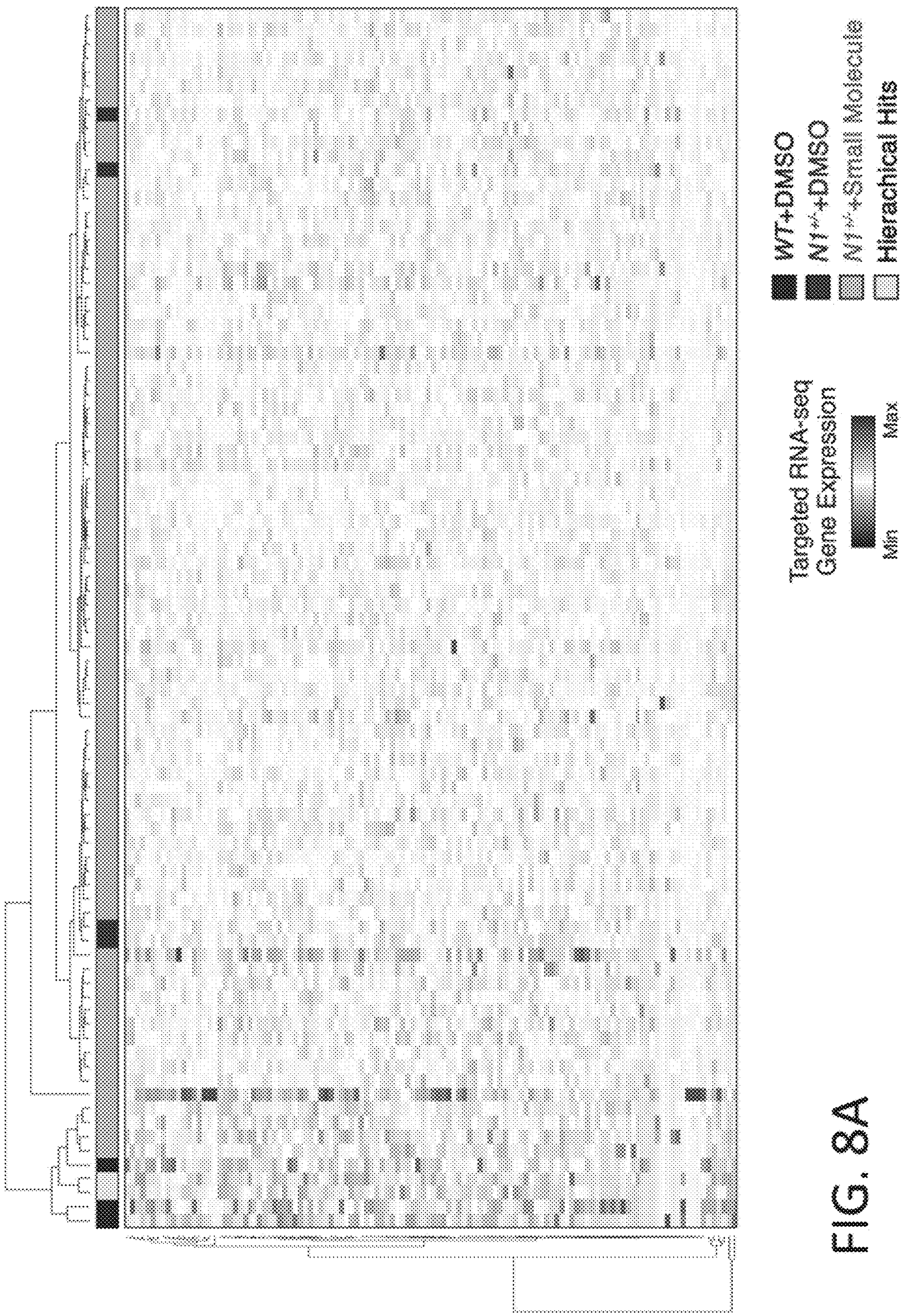
FIG. 8A depicts a hierarchical clustering of transcriptional profiles of $N1^{+/-}$ ECs treated with each of the small molecules (from LOPAC library plate 14 of 16) compared to $N1^{+/-}$ or WT ECs exposed to DMSO.
Figure 8B:
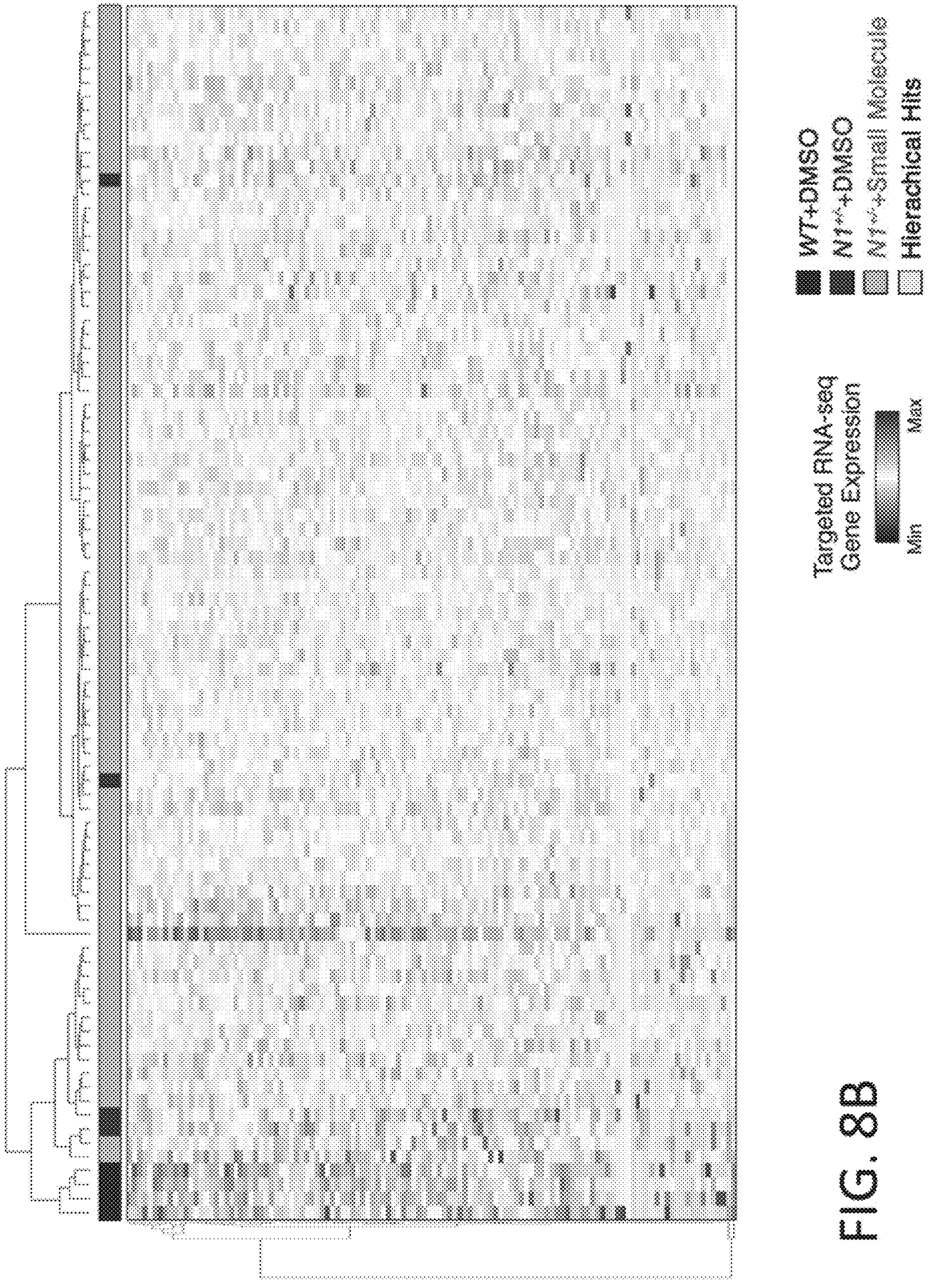
FIG. 8B depicts a hierarchical clustering of transcriptional profiles of $N1^{+/-}$ ECs treated with each of the small molecules (from LOPAC library plate 3 of 16) compared to $N1^{+/-}$ or WT ECs exposed to DMSO. No small molecules from LOPAC library plate 3 sufficiently restored the transcriptional profile of $N1^{+/-}$ ECs such that they clustered with WT ECs.

The large number of replicates of WT and N1-haploinsufficient ECs treated with DMSO or small molecules allowed mapping of the gene network regulated by N1 to a higher degree of confidence than experiments with fewer observations of the network state. Network inference predicted that SOX7 and WNT signaling effector TCF4, both of which are upregulated by N1 haploinsufficiency and are potentially pro-osteogenic genes, were highly connected within the dysregulated network, with SOX7 being the third most highly connected gene overall (FIGS. 1A and 4A-B). Concordant with prior perturbation experiments, BMP signaling effector SMAD1, which is also upregulated by N1 haploinsufficiency, was predicted to be more peripheral within the network. The most highly interconnected gene was CSDA, which is downregulated by N1 haploinsufficiency and serves as an anti-inflammatory repressor of the GM-CSF promoter.

Example 2

Network-Based Screen Identified Network-Correcting Small Molecules

Materials and Methods

Promising small molecules were identified using either K-nearest neighbor (KNN) or hierarchical clustering algorithms. A KNN algorithm (k=2) was trained on 73 DMSO-exposed WT and 78 DMSO-exposed $N1^{+/-}$ ECs and had an accuracy of 99.3% by leave-one-out (LOO) cross-validation. The KNN algorithm was then applied to the small molecule-exposed ECs to identify small molecules that sufficiently corrected the network gene expression such that treated $N1^{+/-}$ ECs were classified as WT. Hierarchical clustering was applied using a complete agglomeration method to identify small molecules that promoted $N1^{+/-}$ ECs to cluster with WT ECs and separately from DMSO-exposed $N1^{+/-}$ ECs. Promising small molecules identified by the two aforementioned methods were applied to $N1^{+/-}$ ECs in duplicate or triplicate with controls of DMSO-exposed WT or $N1^{+/-}$ ECs (n=4 each) and analyzed by targeted RNA-seq as described above. The previously-trained KNN algorithm was applied to the validation samples and compounds that sufficiently corrected the network gene expression such that one or more replicates of treated $N1^{+/-}$ ECs classified as WT were selected for further analysis.

Results

Having mapped the key regulatory nodes within the network dysregulated by N1 haploinsufficiency, small molecules were identified that corrected the network back to the normal state. A K-nearest neighbors (KNN) algorithm was trained to classify the network gene expression by targeted RNA-seq as WT or $N1^{+/-}$ based on isogenic ECs of each genotype exposed to DMSO. The KNN algorithm classified ECs as either WT or $N1^{+/-}$ with 99.3% accuracy by leave-one-out (LOO) cross-validation. The single $N1^{+/-}$ EC replicate that was misclassified as WT appeared near the boundary of the two classes when mapped onto two principle components (FIG. 1*i*).

The trained KNN algorithm was then applied to $N1^{+/-}$ ECs exposed to one of 1595 small molecules, with the vast majority remaining classified as $N1^{+/-}$, but eleven molecules sufficiently corrected the network gene expression such that the treated $N1^{+/-}$ ECs were classified as WT (FIGS. 1C and 10A-C). These network-correcting molecules were Cytochalasin; Fmoc-leu; GSK837149A; RO-4929097; Alprostadil; Norfloxacin; YC-1; CB_1954; L-741,626; Naloxone benzoylhydrazone; and Tulobuterol_hydrochloride.

Increased cell migration and proliferation were hypothesized to contribute to valve thickening and calcification in CAVD (cardiac aortic valve disease), and concordantly, two additional network-correcting molecules were anti-proliferative, including CB1954 and cytochalasin. The network-correcting molecules also included two vasodilating compounds, prostaglandin Ei (alprostadil) and beta-adrenoreceptor agonist tulobuterol hydrochloride.

To enhance the diversity of algorithms used to select initial candidates, hierarchical clustering was applied using a complete agglomeration method to identify additional small molecules that promoted N1-haploinsufficient ECs to cluster with WT ECs (FIGS. 1D, 5A-B, 6A-B, 7A-B, 8A-B, and 10A-C). Among the compounds identified were multiple additional vasodilators including beta-adrenoreceptor-modulating molecules alprenolol and amiodarone, alpha-adrenoreceptor antagonist phentolamine mesylate, and acetylcholine receptor agonist carbachol. This method also identified potentially anti-inflammatory molecules BWB70C and cyclooxygenase inhibitor piroxicam. Additional candidates included potentially anti-atherogenic TG003 and potentially anti-osteogenic XCT790.

Of the candidates identified by the aforementioned complete or single linkage methods, nine compounds sufficiently corrected the network gene expression such that one or more replicates of treated $N1^{+/-}$ ECs were classified as WT by the KNN algorithm in validation trials. When plotted on two principle components, N1-haploinsufficient ECs treated with the validated molecules localized more closely to WT ECs than those treated with molecules that did not validate. The validated molecules were Cytochalasin; Fmoc-leu; GSK837149A; RO-4929097; CB_1954; Biperiden_hydrochloride; Putrescine dihydrochloride, TG003, and XCT790.

Example 3

Network-Correcting Molecules Restored Pathways Governing Arterial Thrombosis and Angiogenesis

Materials and Methods

Whole Transcriptome RNA-Seq and Analysis Pipeline

ECs were lysed and RNA was isolated using the Qiagen RNeasy Micro purification kit. RNA-seq libraries were constructed using the Clontech SMRTer Stranded RNA-seq Library Prep Kit for Illumina per kit protocol. Libraries were analyzed by Agilent Bioanalyzer, normalized to equivalent concentration, pooled, gel purified, and sequenced 75 bp paired-end on an Illumina NextSeq instrument with 10% PhiX.

Sequencing quality was assessed with FASTQC (located on the web by placing "www." in front of "bioinformatics.babraham.ac.uk/projects/fastqc/"). Reads were aligned to the hg19 (*Homo sapiens* assembly February 2009) transcriptome and genome using the Spliced Transcripts Alignment to a Reference (STAR) Aligner (Dobin et al., *Bioinformatics.* 2012; 29:15-21) and differential expression was analyzed using Cuffdiff (Trapnell et al., *Nat Biotechnol.* 2012; 31:46-53). HOPACH was used for clustering with the correlation metric (van der Laan and Pollard; located on the web by placing "www." in front of "bioconductor.org/packages/devel/bioc/manuals/hopach/man/hopach.pdf". GO analyses were completed using GO-Elite and ToppGene (Chen et al., *Nucleic Acids Research.* 2009; 37:W305-W311; Zambon et al., *Bioinformatics.* 2012; 28:2209-2210). Network diagrams were generated using NetworkX (Hagberg et al., SciPy. 2008) based on network connections inferred from mRNA-seq gene expression of isogenic $N1^{+/-}$ compared to WT ECs with colors based on whole transcriptome RNA-seq gene expression of DMSO- vs small molecule-treated WT and $N1^{+/-}$ ECs.

Results

Figure 2A:
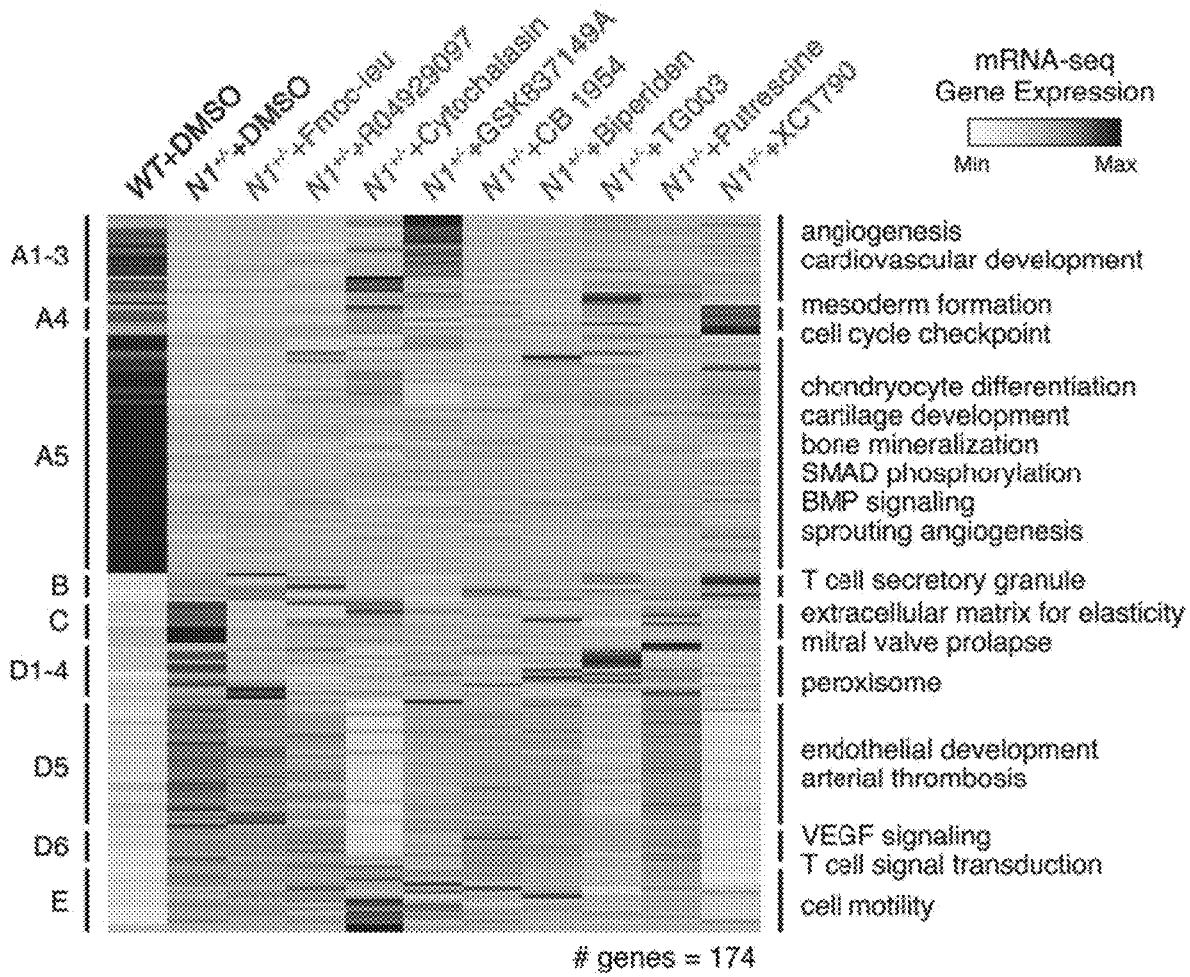
FIG. 2A depicts the effect of network-correcting molecules on genes dysregulated in $N1^{+/-}$ ECs (from whole transcriptome RNA-seq). Gene ontology (GO) pathways enriched in each gene cluster are indicated to the right.
Figure 2B:
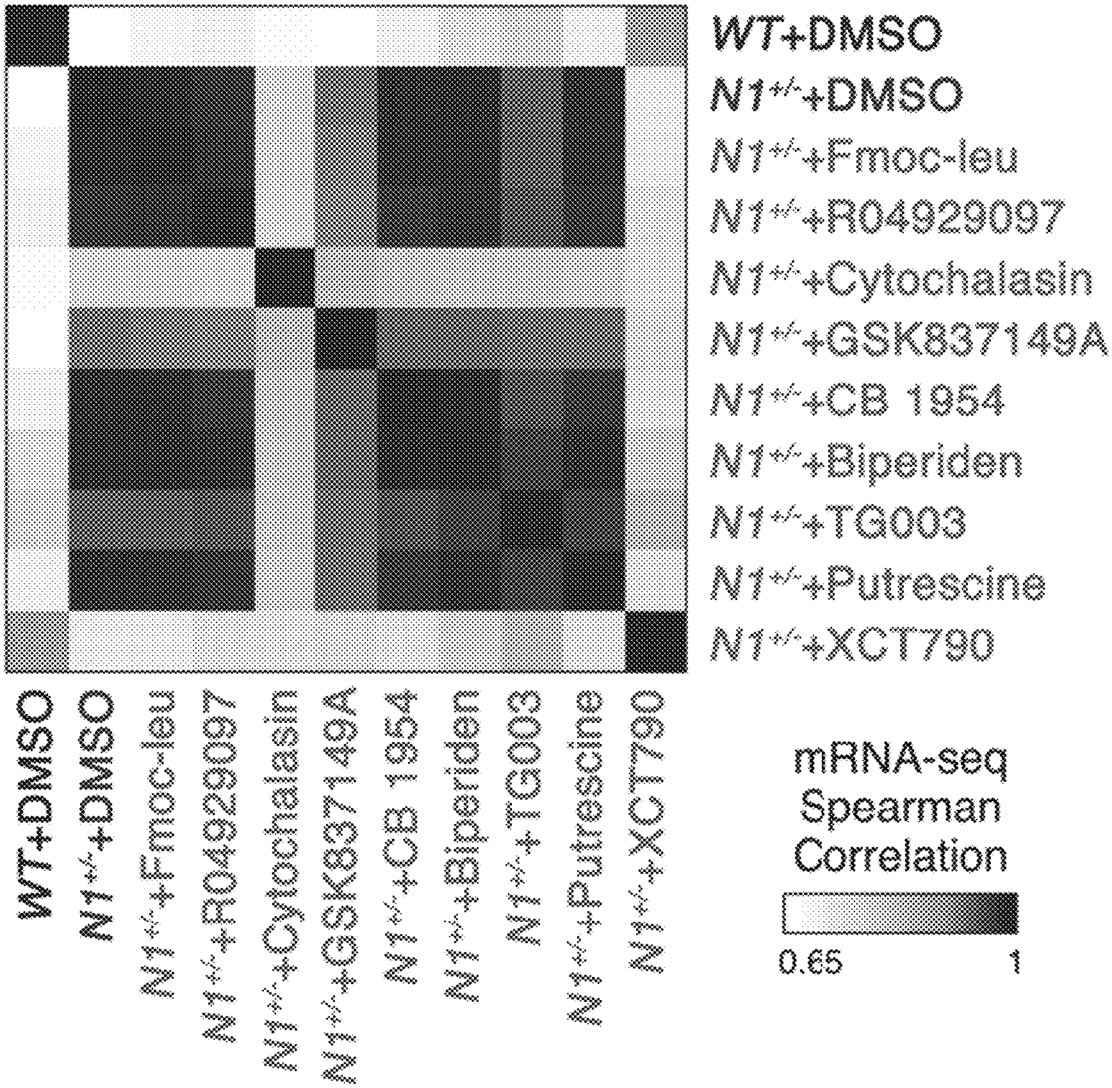
FIG. 2B depicts correlation of gene expression in WT ECs with gene expression in $N1^{+/-}$ ECs exposed to DMSO or network-correcting molecules (from whole transcriptome RNA-seq).

Whole transcriptome RNA-seq was performed to determine the effect of the identified network-correcting small molecules on the transcriptional landscape as a whole (FIG. 2A). Overall, XCT790 was the most effective at repressing genes aberrantly activated in N1-haploinsufficient ECs, including those genes involved in extracellular matrix for elasticity, cell motility, arterial thrombosis, T cell signaling, and peroxisomes. TG003 was also broadly effective at repressing these genes, albeit to a lesser degree, with less effect specifically on peroxisome-related genes. Cytochalasin was effective at downregulating arterial thrombosis and T cell signal genes, but worsened the dysregulation of cell motility genes. XCT790, TG003, and cytochalasin had the strongest repressive effect on cadherin-11, repression of which prevents CAVD in $N1^{+/-}$ mice exposed to high fat diet (FIG. 9A). XCT790 also effectively restored the transcription of mesoderm and cell cycle checkpoint genes, and GSK837149A restored transcription of a complementary group of genes involved in angiogenesis and cardiovascular development. As a single agent, XCT790 was most effective at restoring both aberrantly activated and repressed genes, and XCT790-treated ECs correlated most strongly with the transcriptional profile of WT ECs (FIG. 2B).

Figure 2C:
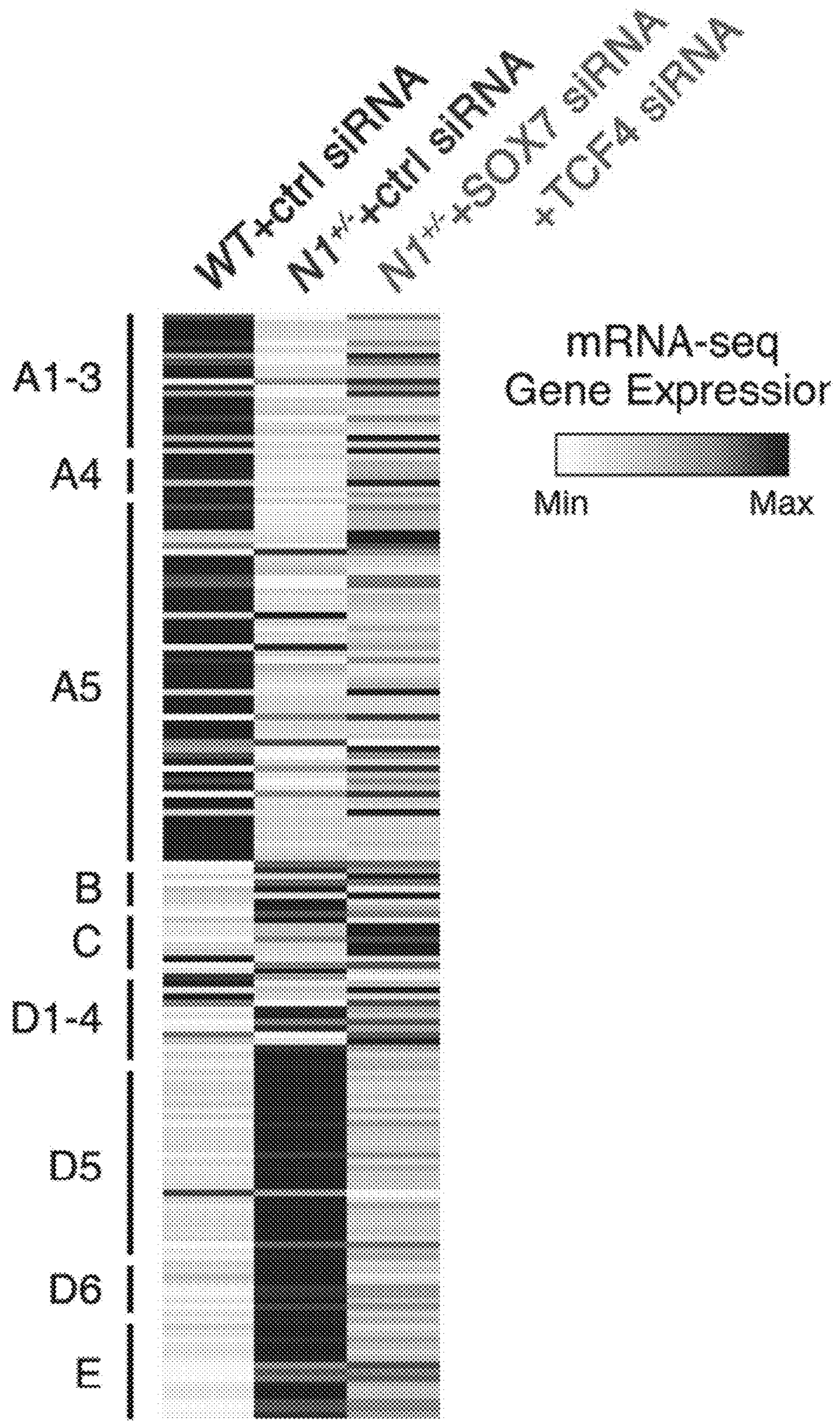
FIG. 2C depicts correlation of N1-dependent gene expression by siRNA repression of SOX7 and TCF4 regulatory nodes, which are upregulated by N1 haploinsufficiency (from whole transcriptome RNA-seq).
Figure 2D:
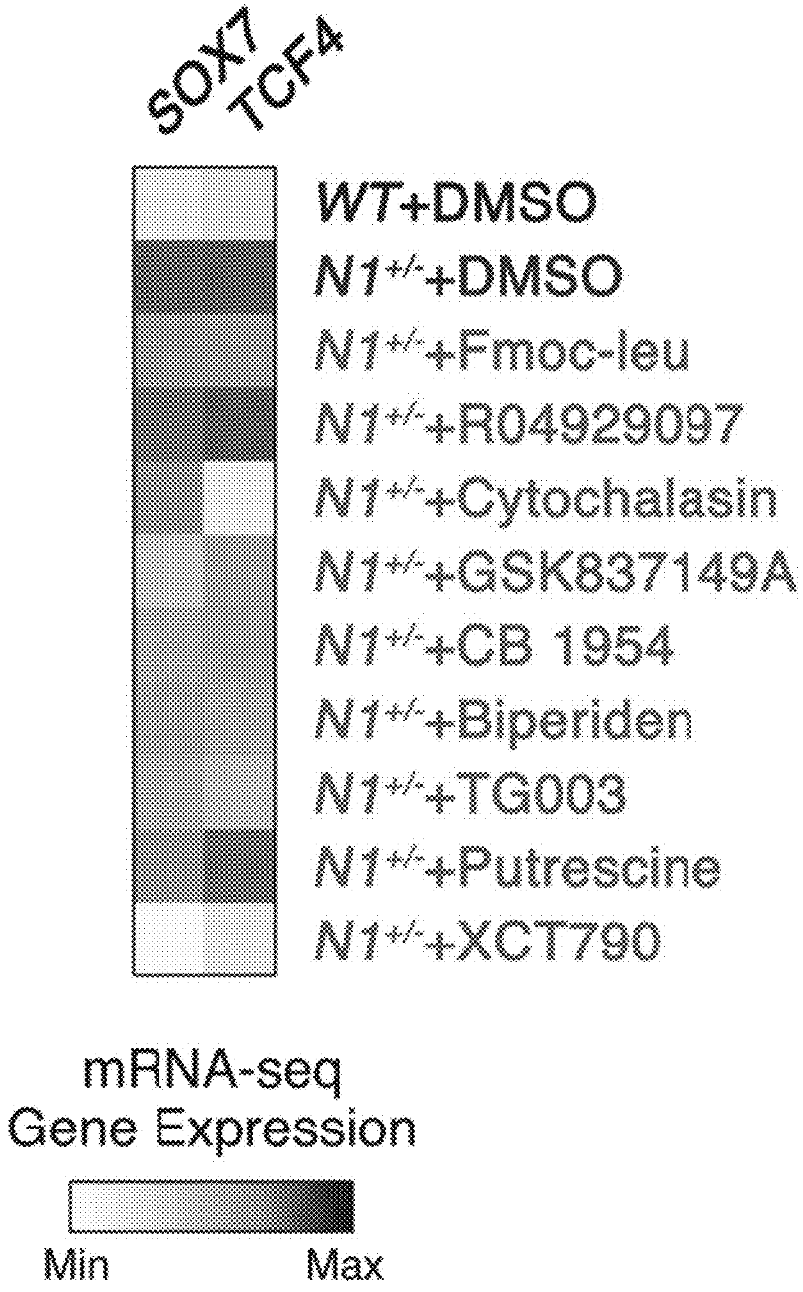
FIG. 2D depicts the repression of SOX7 and TCF4 regulatory nodes by network-correcting molecules (from whole transcriptome RNA-seq).
Figure 2E:
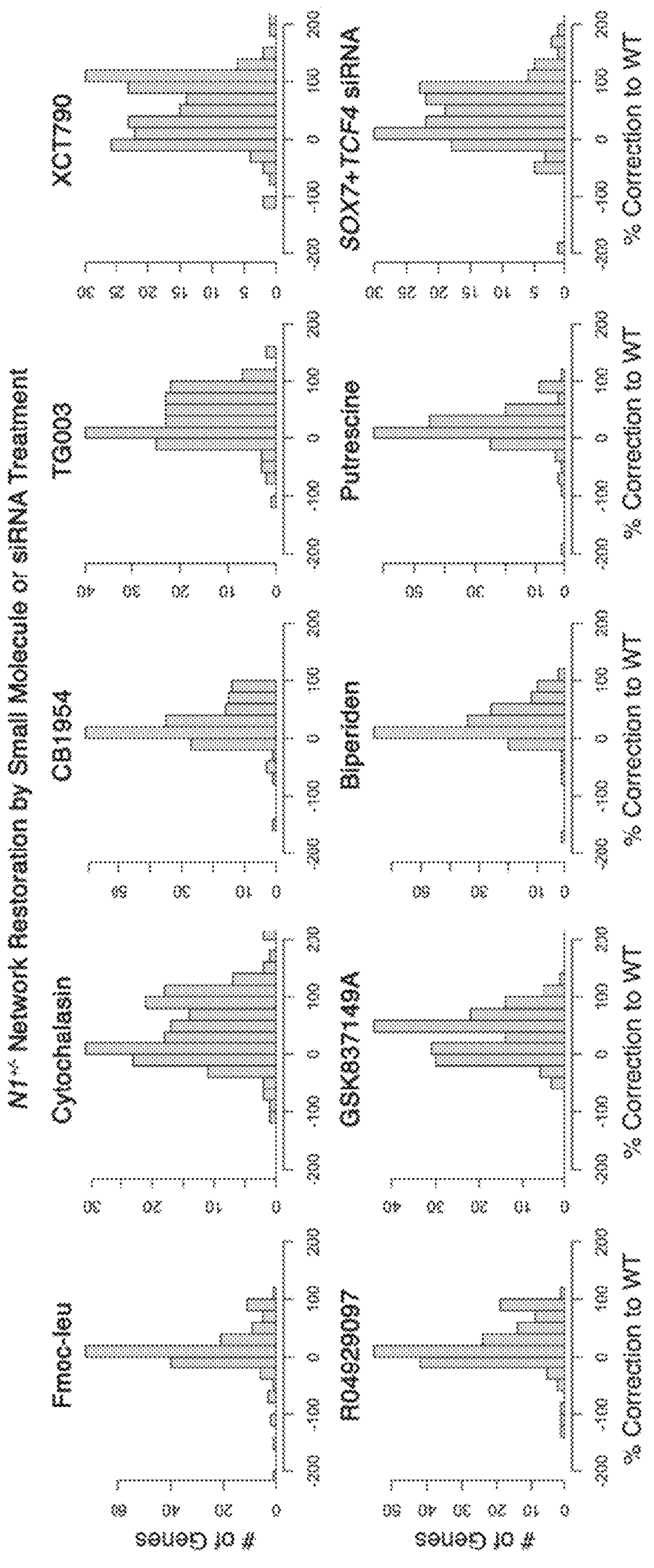
FIG. 2E depicts the extent of N1-dependent network restoration in $N1^{+/-}$ ECs treated with network-correcting molecules or siRNA targeting SOX7 and TCF4 (from whole transcriptome RNA-seq). Positive values indicate correction towards or past WT expression level. Negative values indicate worsened dysregulation.

Given SOX7 and TCF4's predicted role as central regulatory nodes within the network dysregulated by N1 haploinsufficiency, correction of these nodes was predicted to have a broad restorative effect on the network as a whole. Indeed, siRNA directly targeting these nodes broadly corrected both upregulated and downregulated genes in N1-haploinsufficient ECs back towards their normal state (FIGS. 2C and 9B). Concordantly, the compound with the strongest restorative effect on these regulatory nodes, XCT790, drove N1-haploinsufficient ECs to correlate most strongly with WT ECs and corrected the greatest number of genes to the greatest degree from the compounds identified in the network-based screen (FIG. 2B, D-E). Thus, treatment that corrected the expression of central regulatory nodes SOX7 and TCF4 was the most effective at restoring the network as a whole.

Figure 3A:
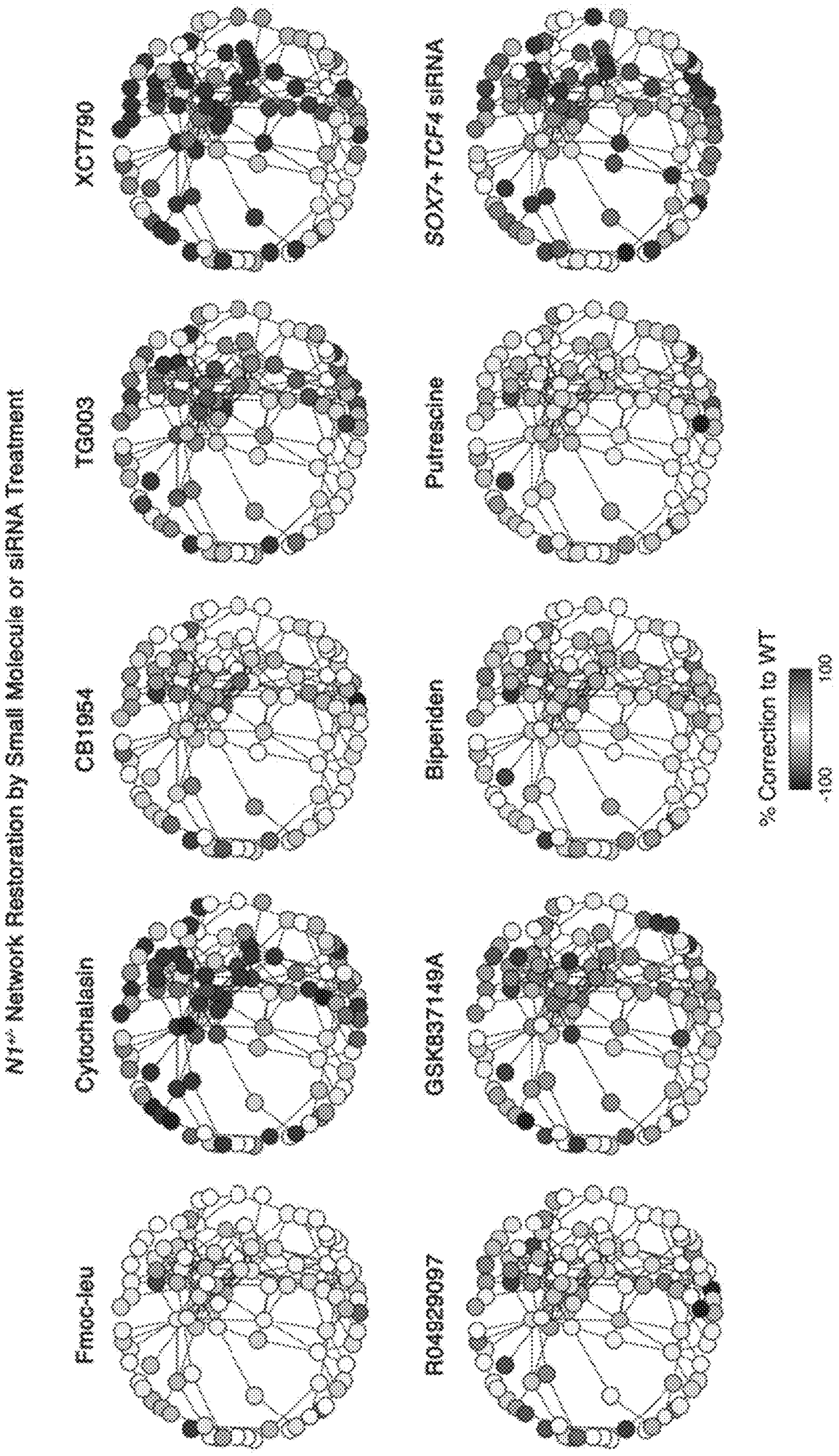
FIG. 3A depicts the percent correction of nodes within the N1-dependent network to WT expression levels in $N1^{+/-}$ ECs treated with network-correcting molecules or siRNA targeting SOX7 and TCF4.

Determining the region of the network impacted by each small molecule was hypothesized to inform the selection of molecule combinations to further restore the network to the normal state. When mapping the effects of each small molecule as well as the combination of siRNA targeting SOX7 and TCF4, XCT790 had the strongest restorative effect on central regions of the network and most closely mimicked the effects of direct siRNA targeting of key nodes SOX7 and TCF4 (FIG. 3A). TG003 also had a strong restorative effect but closely overlapped with the genes affected by XCT790. Conversely, GSK837149A restored more complementary genes to XCT790 including inflammatory regulator CEACAM1 and JNK signaling factor NRK. The complementary network-correcting effects of XCT790 and GSK837149A suggest they may be even more effective in combination.

Example 4

Network-Correcting Molecules Reduced Cardiac Valve Stenosis In Vivo

Materials and Methods

In Vivo Small Molecule Treatment, Echocardiography, and Staining of Calcification Protocols were reviewed/approved by UCSF Institutional Animal Care and Use Committee, San Francisco, CA. $N1^{+/-}$ and $mTR^{het}$ C57Bl6 mice (purchased from Jackson Labs: #002797 and #004132, respectively) were used to generate double mutant animals. Breedings were performed as previously described (Theodoris et al., The Journal of Clinical Investigation. 2017; 127:1683) to generate $N1^{+/-}/mTR^{8}$ mice. Mice were treated with XCT790 (5 mg/kg/day), TG003 (0.3 mg/kg/day or 2 mg/kg/day, results pooled for analysis), Fmoc-leu (0.6 mg/kg/day), GSK837149A (4.5 mg/kg/day), biperiden (10 mg/kg/day), CB1954 (15 mg/kg/day), putrescine (0.26 mg/kg/day), naloxone (25 mg/kg/day), all by intraperitoneal injection, and RO4929097 (60 mg/kg/day) by oral gavage, or equivalent volume of solvent (DMSO or saline) for four weeks starting at the fourth postnatal week.

Echocardiography was performed under isofluorane anesthesia with standard measurement techniques using the Vevo 770 Imaging System (VisualSonics) equipped with an RMV-707B transducer with central frequency of 30 MHz. Peak blood flow velocity through AVs and PVs was obtained by pulsed wave Doppler in the modified parasternal long and short axis views. The average of three cardiac cycles was used for each measurement.

Hearts were fixed by perfusion fixation under anesthesia using isofluorane by ventricular KCl injection followed by PBS wash and fixation with 4% paraformaldehyde. Hearts were then incubated in 10% formalin overnight. The cardiac apex was cut parallel to the aortic root, and the heart tissue was then paraffin processed using standard protocols and embedded with the cut surface down. The resulting paraffin block was trimmed and angled to obtain a full three-leaflet view of the aortic root. The root was serially sectioned at 5 m intervals from the base of the aortic sinus and mounted on slides. The slides were then deparaffinized, and calcification was stained with 2% Alizarin Red (pH 4.1-4.3) as previously described (Theodoris et al., *The Journal of Clinical Investigation.* 2017; 127:1683).

Figure 3B:
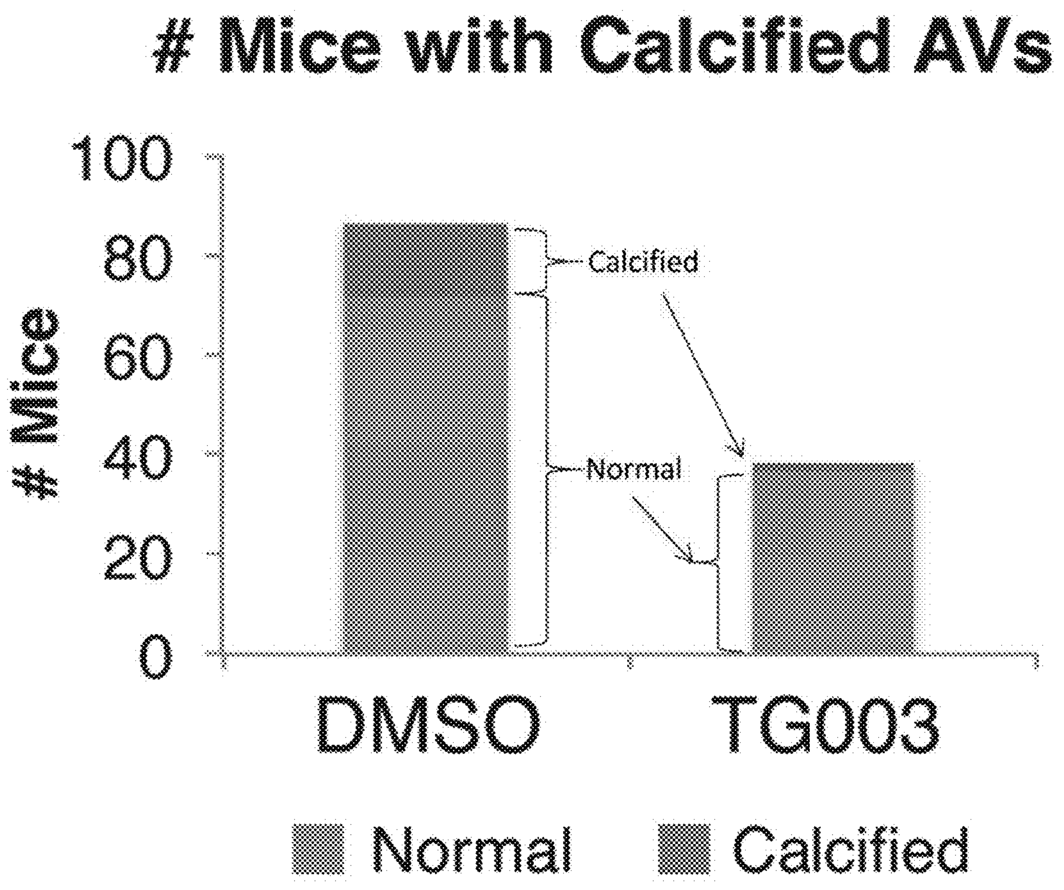
FIG. 3B depicts the number of $N1^{+/-}/mTR^{G2}$ mice with calcified AVs by Alizarin red staining after treatment with TG003 (2 of 38) or DMSO (14 of 86) (p=0.09, $X^2$ test).
Figure 3C:
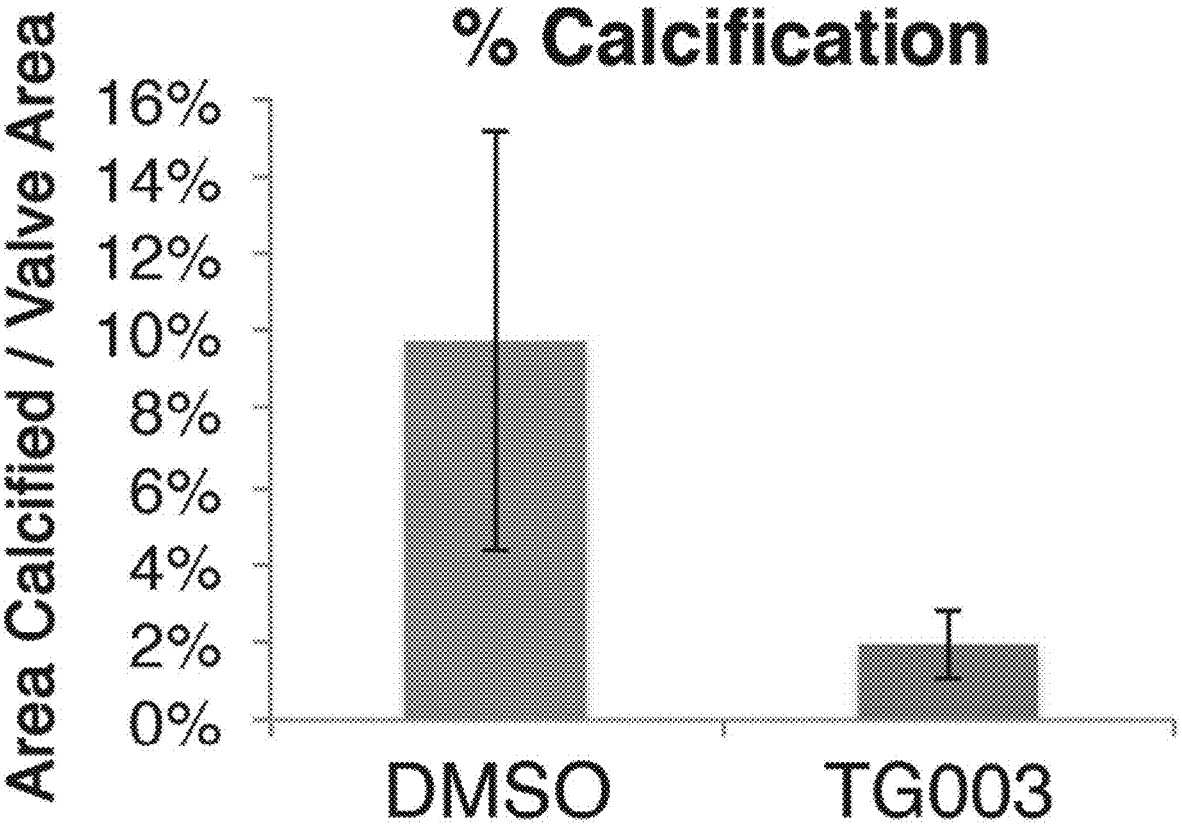
FIG. 3C depicts the percentage of the AV calcified by Alizarin red staining in $N1^{+/-}$ $mTR^{G2}$ mice treated with TG003 (n=2) or DMSO (n=14) (p=0.09, one-sided t-test). Error bars represent standard error.
Figure 3D:
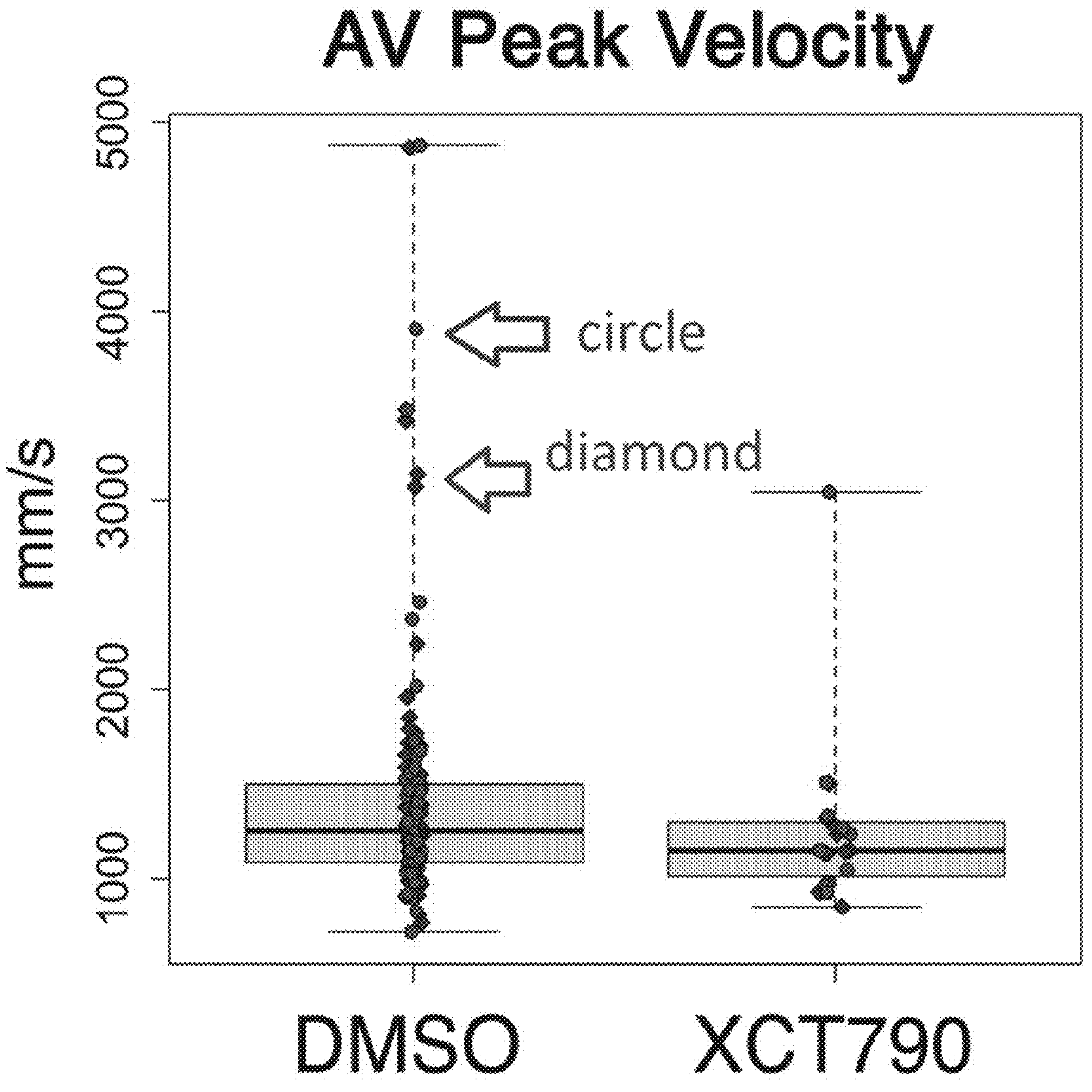
FIG. 3D depicts AV peak velocity by echocardiography in $N1^{+/-}/mTR^{G2}$ mice treated with XCT790 (n=17) or DMSO (n=86) (p=0.17, one-sided t-test). Boxes represent the interquartile range, whiskers represent the range, and the solid horizontal line represents the median. Circular dots represent females and diamonds represent males.
Figure 3E:
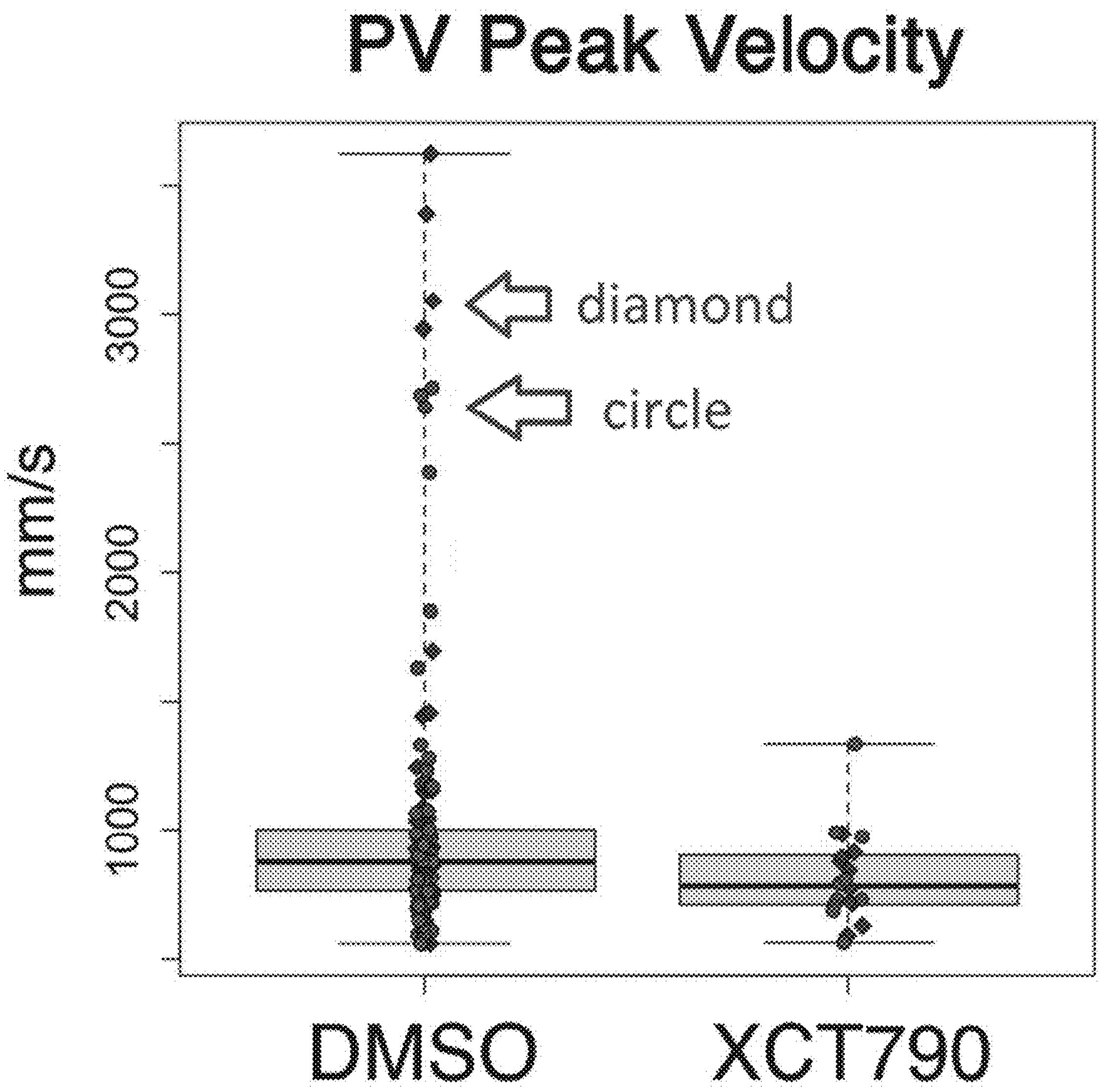
FIG. 3E depicts PV peak velocity by echocardiography in $N1^{+/-}/mTR^{G2}$ mice treated with XCT790 (n=17) or DMSO (n=86) (p=0.001, one-sided t-test). Boxes represent the interquartile range, whiskers represent the range, and the solid horizontal line represents the median. Circular dots represent females and diamonds represent males.

Results $N1^{+/-}$ mice with shortened telomeres develop age-dependent AV and pulmonary valve (PV) stenosis, mimicking the range of human disease caused by N1 haploinsufficiency (Theodoris et al., *The Journal of Clinical Investigation.* 2017; 127:1683). To determine whether the identified network-correcting molecules were sufficient to prevent cardiac valve disease caused by N1 haploinsufficiency in vivo, $N1^{+/-}$ mice with shortened telomeres (generation 2 (G2) mice lacking telomerase activity due to mutations in the telomerase RNA component Terc (mTR)) were treated with either XCT790 or TG003 for four weeks starting at the fourth postnatal week. Compared to DMSO-treated mice, TG003 reduced the number of mice that developed calcification by 68% (p=0.09) and the extent of calcification by 80% (p=0.09) by Alizarin red staining (FIGS. 3B-C), though did not significantly impact AV or PV stenosis by echocardiography (FIGS. 9C-D). XCT790, which most effectively restored the network in vitro, was sufficient to prevent PV stenosis in vivo by echocardiography (p=0.022) and showed a trend of reducing AV stenosis by echocardiography (p=0.068) (FIG. 3D-E). Compared to DMSO, XCT790 also reduced the number of mice that developed calcification by 64%, and the single XCT790-treated mouse that developed calcification had 99% less calcification than the average DMSO-treated mouse, though these effects did not meet statistical significance (FIGS. 9E-F). Overall, XCT790 significantly prevented PV stenosis, and both XCT790 and TG003 showed a trend of reducing AV calcification in NJ $mTR^{G2}$ mice. The network-based drug screen thus effectively identified network-correcting molecules promising for preventing cardiac valve disease in vivo.

Additional compounds, Fmoc-leu, GSK837149A, biperiden, CB1954, putrescine, naloxone, and RO4929097, were tested in vivo (see above methods for Example 4) in a small initial cohort with results as shown in FIGS. 11A-15B.

Based on the small number of initial mice tested, there is insufficient statistical power to conclude statistical significance thus far.

REFERENCES

1. Theodoris C V, Li M, White M P, Liu L, He D, Pollard K S, Bruneau B G, Srivastava D. Human Disease Modeling Reveals Integrated Transcriptional and Epigenetic Mechanisms of NOTCH1 Haploinsufficiency. *Cell.* 2015; 160:1072-1086.
2. White M P, Rufaihah A J, Liu L, Ghebremariam Y T, Ivey K N, Cooke J P, Srivastava D. Limited Gene Expression Variation in Human Embryonic Stem Cell and Induced Pluripotent Stem Cell Derived Endothelial Cells. *Stem Cells.* 2012; 31:92-103.
3. Margolin A A, Nemenman I, Basso K, Wiggins C, Stolovitzky G, Dalla Favera R, Califano A. ARACNE: an algorithm for the reconstruction of gene regulatory networks in a mammalian cellular context. *BMC Bioinformatics.* 2006; 7 Suppl 1:S7.
4. Hagberg A A, Schult D A, Swart P J. Exploring Network Structure, Dynamics, and Function using NetworkX. SciPy. 2008;
5. Dobin A, Davis C A, Schlesinger F, Drenkow J, Zaleski C, Jha S, Batut P, Chaisson M, Gingeras T R. STAR: ultrafast universal RNA-seq aligner. *Bioinformatics.* 2012; 29:15-21.
6. Trapnell C, Hendrickson D G, Sauvageau M, Goff L, Rinn J L, Pachter L. Differential analysis of gene regulation at transcript resolution with RNA-seq. *Nat Biotechnol.* 2012; 31:46-53.
7. van der Laan M J, Pollard K S. A new algorithm for hybrid hierarchical clustering with visualization and the bootstrap [Internet].
8. Chen J, Bardes E E, Aronow B J, Jegga A G. ToppGene Suite for gene list enrichment analysis and candidate gene prioritization. *Nucleic Acids Research.* 2009; 37:W305-W311.
9. Zambon A C, Gaj S, Ho I, Hanspers K, Vranizan K, Evelo C T, Conklin B R, Pico A R, Salomonis N. G O-Elite: a flexible solution for pathway and ontology over-representation. *Bioinformatics.* 2012; 28:2209-2210.
10. Theodoris C V, Mourkioti F, Huang Y, Ranade S, Liu L, Blau H M, Srivastava D. Long telomeres protect against age-dependent cardiac disease caused by NOTCH1 haploinsufficiency. *The Journal of Clinical Investigation.* 2017; 127:1683.
11. Mercer T R, Gerhardt D J, Dinger M E, Crawford J, Trapnell C, Jeddeloh J A, Mattick J S, Rinn J L. Targeted RNA sequencing reveals the deep complexity of the human transcriptome. *Nat Biotechnol.* 2011; 30:99-104.
12. Thomas M Blomquist ELCJLLJYLMSALJLMLL-SKMJCW. Targeted RNA-Sequencing with Competitive Multiplex-PCR Amplicon Libraries. *PLoS ONE.* 2013; 8:e79120.
13. Garg V, Muth A N, Ransom J F, Schluterman M K, Barnes R, King I N, Grossfeld P D, Srivastava D. Mutations in NOTCH1 cause aortic valve disease. *Nature.* 2005; 437:270-274.
14. Mohamed S A, Aherrahrou Z, Liptau H, Erasmi A W, Hagemann C, Wrobel S, Borzym K, Schunkert H, Sievers H H, Erdmann J. Novel missense mutations (p.T596M and p.P1797H) in NOTCH1 in patients with bicuspid aortic valve. *Biochemical and Biophysical Research Communications.* 2006; 345:1460-1465.
15. L S Coles PDFOMAVMFS. Cold shock domain proteins repress transcription from the GM-CSF promoter. *Nucleic Acids Research.* 1996; 24:2311.
16. Schneider J G, Yang Z, Chakravarthy M V, Lodhi I J, Wei X, Turk J, Semenkovich C F. Macrophage Fatty-acid Synthase Deficiency Decreases Diet-induced Atherosclerosis. *J Biol Chem.* 2010; 285:23398-23409.
17. Li A C, Brown K K, Silvestre M J, Willson T M, Palinski W, Glass C K. Peroxisome proliferator-activated receptor γ ligands inhibit development of atherosclerosis in LDL receptor-deficient mice. *J Clin Invest.* 2000; 106:523-531.
18. Cheang W S, Fang X, Tian X Y. Pleiotropic Effects of Peroxisome Proliferator-Activated Receptor ^|^gamma; and ^|^delta; in Vascular Diseases. *Circ J.* 2013; 77:2664-2671.
19. Liu S-L, Li Y—H, Shi G-Y, Chen Y—H, Huang C—W, Hong J-S, Wu H-L. A novel inhibitory effect of naloxone on macrophage activation and atherosclerosis formation in mice. *J Am Coll Cardiol.* 2006; 48:1871-1879.
20. Tsou C Y, Chen C Y, Zhao J F, Su K H, Lee H T, Lin S J, Shyue S K, Hsiao S H, Lee T S. Activation of soluble guanylyl cyclase prevents foam cell formation and atherosclerosis. *Acta Physiol.* 2013; 210:799-810.
21. Mahler G J, Farrar E J, Butcher J T. Inflammatory Cytokines Promote Mesenchymal Transformation in Embryonic and Adult Valve Endothelial Cells. *Arteriosclerosis, Thrombosis, and Vascular Biology.* 2012; 33:121-130.
22. Fedorov O, Huber K, Eisenreich A, Filippakopoulos P, King O, Bullock A N, Szklarczyk D, Jensen L J, Fabbro D, Trappe J, Rauch U, Bracher F, Knapp S. Specific CLK Inhibitors from a Novel Chemotype for Regulation of Alternative Splicing. *Chemistry & Biology.* 2011; 18:67-76.
23. Clark C R, Bowler M A, Snider J C, Merryman W D. Targeting Cadherin-11 Prevents Notch1-Mediated Calcific Aortic Valve Disease. *Circulation.* 2017; 135:2448-2450.
24. Gray-Owen S D, Blumberg R S. CEACAM1: contact-dependent control of immunity. *Nat Rev Immunol.* 2006; 6:433-446.
25. Nakano K, Yamauchi J, Nakagawa K, Itoh H, Kitamura N. NESK, a Member of the Germinal Center Kinase Family That Activates the c-Jun N-terminal Kinase Pathway and Is Expressed during the Late Stages of Embryogenesis. *J Biol Chem.* 2000; 275:20533-20539.
26. Foffa I, Ait Ali L, Panesi P, Mariani M, Festa P, Botto N, Vecoli C, Andreassi M G. Sequencing of NOTCH1, GATA5, TGFBR1 and TGFBR2 genes in familial cases of bicuspid aortic valve. *BMC Med Genet.* 2013; 14:44.
27. Hadji F, Boulanger M-C, Guay S—P, Gaudreault N, Amellah S, Mkannez G, Bouchareb R, Marchand J T, Nsaibia M J, Guauque-Olarte S, Pibarot P, Bouchard L, Bossé Y, Mathieu P. Altered DNA Methylation of Long Noncoding RNA H19 in Calcific Aortic Valve Disease Promotes Mineralization by Silencing NOTCH1. *Circulation.* 2016; 134:1848-1862.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating cardiac valve disease, the method comprising:

administering to a subject in need thereof a therapeutically effective amount, in a range of about 30 mg/kg body weight to about 500 mg/kg body weight combined of XCT-790, (2E-3-(4-{[2,4-bis(trifluoromethyl) benzyl]oxy}-3-methoxyphenyl)-2-cyano-N-[5-(trifluoromethyl)-1,3,4-thiadiazol-2-yl]acrylamide) and TG-003 (((Z)-1-(3-ethyl-5-methoxy-2,3-dihydrobenzothiazol-2-ylidene)propan-2-one)).

2. The method according to claim 1, wherein the cardiac valve disease is a calcific aortic valve disease.

3. A method of treating cardiac valve disease by administering to a subject in need thereof a therapeutically effective amount of XCT-790 ((2E-3-(4-{[2,4-bis(trifluoromethyl)benzyl]oxy}-3-methoxyphenyl)-2-cyano-N-[5-(trifluoromethyl)-1,3,4-thiadiazol-2-yl]acrylamide)) or TG-003 (((Z)-1-(3-ethyl-5-methoxy-2,3-dihydrobenzothiazol-2-ylidene)propan-2-one)).

4. The method according to claim 3, wherein the cardiac valve disease is a calcific aortic valve disease.

* * * * *